(12) United States Patent
Englehardt et al.

(10) Patent No.: US 8,241,622 B2
(45) Date of Patent: Aug. 14, 2012

(54) ADENO-ASSOCIATED VIRUS VECTORS WITH INTRAVECTOR HETEROLOGOUS TERMINAL PALINDROMIC SEQUENCES

(75) Inventors: John F. Englehardt, Iowa City, IA (US); Ziying Yan, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 797 days.

(21) Appl. No.: 10/837,029

(22) Filed: Apr. 30, 2004

(65) Prior Publication Data
US 2004/0248301 A1 Dec. 9, 2004

Related U.S. Application Data

(63) Continuation-in-part of application No. 10/194,421, filed on Jul. 12, 2002, now abandoned.

(60) Provisional application No. 60/305,204, filed on Jul. 13, 2001.

(51) Int. Cl.
*C12N 15/00* (2006.01)
*C12N 15/63* (2006.01)
*C12N 15/86* (2006.01)
*C12N 5/10* (2006.01)
*C12N 15/797* (2006.01)

(52) U.S. Cl. ...... 424/93.2; 424/93.6; 435/325; 435/455; 435/320.1; 435/69.1

(58) Field of Classification Search .......... None
See application file for complete search history.

(56) References Cited

U.S. PATENT DOCUMENTS

| | | | |
|---|---|---|---|
| 5,604,090 A | 2/1997 | Alexander et al. |
| 5,691,176 A | 11/1997 | Lebkowski et al. |
| 5,801,030 A | 9/1998 | McVey et al. |
| 5,834,182 A | 11/1998 | Alexander et al. |
| 5,843,742 A | 12/1998 | Natsoulis et al. |
| 5,853,716 A | 12/1998 | Tattersall et al. |
| 5,869,305 A | 2/1999 | Samulski et al. |
| 5,916,803 A | 6/1999 | Sedlacek et al. |
| 5,990,137 A | 11/1999 | Ternansky et al. |
| 6,083,702 A | 7/2000 | Mitchell et al. |
| 6,083,713 A | 7/2000 | Manly et al. |
| 6,110,744 A | 8/2000 | Fang et al. |
| 6,153,436 A | 11/2000 | Hermonat et al. |
| 6,156,303 A | 12/2000 | Russell et al. |
| 6,200,560 B1 | 3/2001 | Couto et al. |
| 6,221,349 B1 | 4/2001 | Couto et al. |
| 6,270,996 B1 | 8/2001 | Wilson et al. |
| 6,287,569 B1 | 9/2001 | Kipps et al. |
| 6,329,181 B1 | 12/2001 | Xiao et al. |
| 6,358,524 B1 | 3/2002 | Sedlacek et al. |
| 6,436,392 B1 | 8/2002 | Engelhardt et al. |
| 6,468,771 B1 | 10/2002 | Einerhand et al. |
| 6,485,950 B1 | 11/2002 | Kumar et al. |
| 6,491,907 B1 | 12/2002 | Rabinowitz et al. |
| 6,521,225 B1 | 2/2003 | Srivastava et al. |
| 6,544,786 B1 | 4/2003 | Xiao et al. |
| 6,596,535 B1 | 7/2003 | Carter |
| 6,602,667 B1 | 8/2003 | Walker et al. |
| 6,630,344 B1 | 10/2003 | Fang et al. |
| 6,642,051 B1 | 11/2003 | Lynch et al. |
| 6,670,365 B1 | 12/2003 | Gallemi et al. |
| 6,855,549 B1 | 2/2005 | McCray, Jr. et al. |
| 6,897,045 B2 | 5/2005 | Engelhardt et al. |
| 7,067,659 B2 | 6/2006 | Stamler et al. |
| 7,125,717 B2 | 10/2006 | Carter |
| 7,129,374 B2 | 10/2006 | Weissbach et al. |
| 7,749,491 B2 | 7/2010 | Engelhardt et al. |
| 7,803,622 B2 | 9/2010 | Engelhardt et al. |
| 2001/0051611 A1 | 12/2001 | Srivastava et al. |
| 2002/0045264 A1 | 4/2002 | During et al. |
| 2002/0076754 A1 | 6/2002 | Sun et al. |
| 2002/0095135 A1 | 7/2002 | Meeker et al. |
| 2002/0131956 A1 | 9/2002 | Walsh et al. |
| 2002/0137017 A1 | 9/2002 | Aronheim |
| 2002/0197237 A1 | 12/2002 | Engelhardt et al. |
| 2003/0103939 A1 | 6/2003 | Engelhardt et al. |
| 2003/0108920 A1 | 6/2003 | Zhang et al. |
| 2003/0148506 A1 | 8/2003 | Kotin |
| 2003/0166284 A1 | 9/2003 | Srivastava et al. |
| 2004/0029106 A1 | 2/2004 | Samulski et al. |
| 2004/0235947 A1 | 11/2004 | Paquin et al. |
| 2007/0110724 A1 | 5/2007 | Samulski et al. |
| 2008/0166758 A1 | 7/2008 | Engelhardt et al. |
| 2008/0226600 A1 | 9/2008 | Engelhardt et al. |
| 2009/0265796 A1 | 10/2009 | Engelhardt et al. |

FOREIGN PATENT DOCUMENTS

| | | |
|---|---|---|
| CA | 2328447 | 4/2007 |
| WO | WO-94/13788 A1 | 6/1994 |
| WO | WO-95/07351 A1 | 3/1995 |
| WO | WO-95/15384 A1 | 6/1995 |
| WO | WO-97/22250 A1 | 6/1997 |
| WO | WO-97122250 A1 | 6/1997 |
| WO | WO-98/09657 A2 | 3/1998 |
| WO | WO-98/09657 A2 | 3/1998 |
| WO | WO-99/18227 A1 | 4/1999 |
| WO | WO-99/18227 A1 | 4/1999 |

(Continued)

OTHER PUBLICATIONS

"International Search Report for Corresponding PCT Application No. PCT/US2005/015315", (Feb. 2, 2007), 7 pgs.
"DNA Vector-Based siRNA", http://www.genscriplcom/rnai_intro.html, (observed Mar. 9, 2004), 3 pgs.
Afione, S. A., et al., "In Vivo Model of Adeno-Associated Virus Vector Persistence and Rescue", *Journal of Virology*, 70(5), (May 1996), 3235-3241.
Ali, R. R., et al., "Gene Transfer into the Mouse Retina Mediated by an Adeno-Associated Viral Vector", *Human Molecular Genetics*, 5(5). (1996), 591-594.
Bartlett, J. S., et al., "Infectious Entry Pathway of Adeno-Associated Virus and Adeno-Associated Virus Vectors", *Journal of Virology*, 74(6), (Mar. 2000), 2777-2785.

(Continued)

*Primary Examiner* — Maria Marvich
(74) *Attorney, Agent, or Firm* — Schwegman, Lundberg & Woessner, P.A.

(57) ABSTRACT

The invention provides recombinant AAV vectors, at least one of which has heterologous terminal palindromic sequences, and methods of using those vectors.

58 Claims, 37 Drawing Sheets

FOREIGN PATENT DOCUMENTS

| | | |
|---|---|---|
| WO | WO-99/32647 A1 | 7/1999 |
| WO | WO-99132647 A1 | 7/1999 |
| WO | WO-99/60146 A1 | 11/1999 |
| WO | WO-99/60146 A1 | 11/1999 |
| WO | WO-99/61601 A2 | 12/1999 |
| WO | WO-99/61601 A2 | 12/1999 |
| WO | WO-00/47220 A1 | 8/2000 |
| WO | WO-00/47220 A1 | 8/2000 |
| WO | WO-00/65038 A2 | 11/2000 |
| WO | WO-00/65038 A2 | 11/2000 |
| WO | WO-0075365 A2 | 12/2000 |
| WO | WO-01/68888 A2 | 9/2001 |
| WO | WO-01/68888 A2 | 9/2001 |
| WO | WO-01/83692 A2 | 11/2001 |
| WO | WO-01/83692 A2 | 11/2001 |
| WO | WO-01/92551 A2 | 12/2001 |
| WO | WO-01/92551 A2 | 12/2001 |
| WO | WO-02/12525 A2 | 2/2002 |
| WO | WO-02/12525 A2 | 2/2002 |
| WO | WO-02/14526 A2 | 2/2002 |
| WO | WO-02/14526 A2 | 2/2002 |
| WO | WO-03/006616 A2 | 1/2003 |
| WO | WO-03/006990 A1 | 1/2003 |
| WO | WO-03/042361 A2 | 5/2003 |
| WO | WO-03/042361 A2 | 5/2003 |
| WO | WO-03/104392 A2 | 12/2003 |
| WO | WO-03/104392 A2 | 12/2003 |
| WO | WO-2004/064844 A1 | 8/2004 |
| WO | WO-2005111220 A3 | 11/2005 |
| WO | WO-2005/119251 A2 | 12/2005 |
| WO | WO-2006/009975 A1 | 1/2006 |
| WO | WO-2007079141 C2 | 7/2007 |
| WO | WO-2007127464 A3 | 11/2007 |

OTHER PUBLICATIONS

Bennett, J., et al., "Real-Time, Noninvasive In Vivo Assessment of Adeno-Associated Virus-Mediated Retinal Transduction", *Investigative Ophthalmology & Visual Science*, 38(13), (Dec. 1997), 2857-2863.

Bohenzky, R. A., et al., "Sequence and Symmetry Requirements Wihtin the Internal Palindromic Sequences of the Adeno-Associated Virus Terminal Repeat", *Virology*, 166, (1988), 316-327.

Brister, J.R., et al., "Rep-Mediated Nicking of the Adeno-Associated Virus Origin Requires Two Biochemical Activities, DNA Helicase Activity and Transesterification", *Journal of Virology*, 73(11), (1999), 9325-9336.

Carter, P. J., et al., "Adeno-Associated Viral Vectors as Gene Delivery Vehicles (Review)", *International Journal of Molecular Medicine*, 6(1), 17-27.

Carter, B. J., et al., "Chapter 11—AAV DNA Replication, Integration, and Genetics", *In: Handbook of Parvoviruses*, vol. 1., Tijssen, P., Editor, CRC Press, Inc., Baco Raton, FL, (1992), 169-226.

Chiorini, J. A., et al., "Cloning and characterization of Adeno-Associated Virus Type 5", *Journal of Virology*, 73(2), (1999), 1039-1319.

Chiorini, J. A. et al., "Detemination of Adeno-Associated Virus Rep68 and Rep 78 Binding Sites by Random Sequence Oligonucleotide Selection", *Journal of Virology*, 69(11), (1995), 7334-7338.

Chiorini, J. A., et al., "Sequnce Requirements for Stable Binding and Function of Rep68 on the Adeno-Associated Virus Type 2 Inverted Terminal Repeats", *Journal of Virology*, 68(11), (1994),7448-7457.

Dietrich, C., et al., "p53-Dependent Cell Cycle Arrest Induced by N-acetyl-L-leuciny1-L leuciny-L-norleucinal in Platelet-Derived Growth Factor-Stimulated human fibroblasts", *Proc. Natl Acad. Sci. USA*, 93(20), (1996), 10815-10819.

Duan, D, et al., "Circular Intermediates of Recombinant Adeno-Associated Virus Have Defined Structural Characterists Resposible for Long-Term Episomal Persistence in Muscule Tissue", *Journal of Virology*, 72(11), (1998),8568-8577.

Duan, D., "Consequences of DNA-Dependent Protein Kinase Catalytic Subunit Deficiency on Recombinant Adeno-Associated Virus Genome Circularization and Heterodimerization in Muscle Tissue", *Journal of Virology*, 77(8), (2003),4751-4759.

Duan, D., et al., "Endosomal Processing Limits Gene Transfer to Polarized Airway Epithelia by Adeno-Associated Virus", *Journal of Clinical Investigation*, 105, (Jun. 2000), 1573-1587.

Duan, D., "Expanding AAV Packaging Capacity With *Trans-* splicing or Overlapping Vectors: A Quantitative Comparison", *Molecular Therapy*, 4(4), (2001), 383-391.

"Response to "Polarity Influences the Efficiency of Recombinant Adenoassociated Virus Infection in Differentiated Airway Epithelia"", *Human Gene Therapy*, 10, (1999), 1553-1557 Whiteway et al.

Englehardt, J., et al., "Adeno-Associated Virus Vectors and Uses Thereof", U.S. Appl. No. 09/684,665, filed Oct. 6, 2000, 141 pgs.

Fisher-Adams, G. , et al., "Integration of Adeno-Associated Virus Vectors in CD34+Human Hematopoietic Progenitor Cells After Transduction", *Blood*, 88 (2), (Jul. 15, 1996), 492-504.

Flotte, T. R., et al., "Adeno-Associated Virus Vector Gene Expression Occurs in Nondividing Cells in the Absence of Vector DNA Integration", *American Journal of Respiratory Cell and Molecular Biology*, 11, (1994),pp. 517-521.

Giraud, C., et al., "Recombinant Junctions Formed by Site-Specific Integration of Adeno-Associated Virus into an Episome", *Journal of Virology*, 69 (11), (Nov. 1995), 6917-6924.

Grimm, D., "From Virus Evolution to Vector Revolution: Use of Naturally Occurring Serotypes of Adeno-Associated Virus (AAV) as Novel Vectors for Human Gene Therapy", *Current Gene Therapy*, 3, (2003), 281-304.

Hagstrom, J. N., et al., "Improved Muscle-Derived Expression of Human Coagulation Factor IX From a Skeletal Actin/CMV Hybrid Enhancer/Promoter", *Blood*95(8), (2000), 2536-2542.

Hasegawa, S. , et al., "Microtubule Involvement in the Intracellular Dynamics for Gene Transfection Mediated by Cationic Lipsomes", *Gene Therapy*, vol. 8, (2001),1669-1673.

Higgins, D. G., "CLUSTAL: a Package for Performing Multiple Sequence Alignment on a Microcomputer.", *Gene*, 73(1), (Dec. 15, 1998), 237-244.

Kessler, P D., et al., "Gene Delivery to Skeletal Muscle Results in Sustained Expression and Systemic Delivery of a Therapeutic Protein", *Proc. Natl. Acad. Sci. USA*, 93(24), (Nov. 26, 1996), 14082-14087.

Lefebvre, R. B., et al., "Conformation Takes Precedence Over Sequence in Adeno-Associated Virus DNA Replication", *Molecular and Cellular Biology*, 4(7), (1984), 1416-1419.

Linden, R. M., et al., "The Recombinant Signals for Adeno-Associated Virus Site-Specific Integration", *Proc. Natl. Acad. USA*, 93, (Jul. 1996), 7966-7972.

McCarty, D. M., et al., "Identification of Linear DNA Sequences That Specifically Bind the Adeno-Associated Virus Rep Protein", *Journal of Virology*, 68(8), (1994), 4988-4997.

McCarty, D. M. et al., "Interaction of the Adeno-Associated Virus Rep Protein With a Sequence Within the A Palindrome of the Viral Terminal Repeat", *Journal of Virology*, 68(9), (1994), 4998-5006.

McLaughlin, S. K., et al., "Adeno-Associated Virus General Transduction Vectors: Analysis of Proviral Structures", *Journal of Virology*, 62 (6), (Jun. 1988), 1963-1973.

Musatov, S. A., et al., "Induction of Circular Episomes During Rescue and Replication of Adeno-Associated Virus Latency", *Virology*, 275, (2000), 411-432.

Nakai, H., et al., "Helper-Independent and AAV-ITR-Independent Chromosomal Integration of Double-Stranded Linear DNA Vectors in Mice", *Molecular Therapy*, 7(1), (2003), 101-111.

Nakai, H., et al., "Increasing the Size of rAAV-Mediated Expression Cassettes in vivo by Intermolecular Joining of Two Complementary Vectors",*Nature Biotechnology*, 18, (2000), 527-532.

Nakai, H., et al., "Recruitment of Single-Stranded Recombinant Adeno-Associated Virus Vector Genomes and Intermolecular Recombinant Are Responsible for Stable Transduction of Liver In Vivo", *Journal of Virology*, 74(20), (2000), 9451-9463.

Ponnazhagan, S., et al., "Lack of Site-Specific Integration of the Recombinant Adeno-Associated Virus 2 Genomes in Human Cells", *Human Gene Therapy*, 8, (Feb. 10, 1997), 257-284.

Qing, K., et al., "Adeno-Associated Virus Type 2-Mediated Gene Transfer: Correlation of Tyrosine Phoshorylation of the Cellular Single-Stranded D Sequence-Binding Protein with Transgene Expression in Human Cells In Vitro and Murine Tissues In Vivo", *Journal of Virology*, 72 (2), (Feb. 1998), 1593-1599.

Qing, K. , et al., "Human Fibroblast Growth Factor Receptor 1 is a Co-Receptor for Infection by Adeno-Associated Virus 2", *Nature Medicine*, 5(1), (Jan. 1999), 71-77.

Qing, K., "Role of Tyrosine Phosphorylation of a Cellular Protein in Adeno-Associated Virus 2-Mediated Transgene Expression", *Proc. Natl. Acad. Sci. USA*, 94, (Sep. 1997), 10879-10884.

Ryan, J. H., et al., "Sequence Requirements for Binding of Rep68 to the Adeno-Associated Virus Terminal Repeats", *Journal of Virology*, 70(3), (1996), 1542-1553.

Snyder, R. O., et al., "Persistent and Therapeutic Concentrations of Human Factor IX in Mice After Hepatic Gene Transfer of Recombinant AAV Vectors", *Nature Genetics*, 16, (Jul. 1997), 270-276.

Srivastava, C. H., et al., "Construction of a Recombinant Human Parvovirus B19: Adeno-Associated Virus 2 (AAV-B19 Hybrid Virus)", *Proc. Natl. Acad. Sci. USA*, 86(20), (1989), 8078-8082.

Summerford, C., et al., "Membrane-Associated Heparan Sulfate Proteoglycan Is a Receptor for Adeno-Associated Virus Type 2 Virions", *Journal of Virology*, 72(2), (Feb. 1998), 1438-1445.

Teramoto, S., "Factors Influencing Adeno-Associated Virus-Mediated Gene Transfer to Human Cystic Fibrosis Airway Epithelial Cells: Comparison With Adenovirus Vectors", *Journal Virology*, 72(11), (Nov. 1998), 8904-8912.

Wagner, J. A., et al., "A Phase I/II Study of tgAAV-CF for the Treatment of Chronic Sinusitis in Patients With Cystic Fibrosis", *Human Gene Therapy*,9(6), (1998), 889-909.

Walsh, C. E., et al., "Phenotypic Correction of Fanconi Anemia in Human Hematopoietic Cells with a Recombinant Adeno-associated Virus Vector", *The Journal of Clinial Investigation*, 94(4), (Oct. 1994), 1440-1448.

Westfall, T. D., et al., "The Ecto-ATPhase Inhibitor ARL 67156 Enhances Parasympathetic Neurotransmission in the Guinea-Pig Urinary Bladder", *European Journal of Pharmacology*, 329, (1997),169-173.

Wu, P. et al., "Adeno-Associated Virus Vector-Mediated Transgene Integration into Neurons and Other Nondividing Cell Targets", *Journal of Virology*, 72 (7), (Jul. 1998), pp. 5919-5926.

Xiao, Xiao , et al., "Efficient Long-Term Gene Transfer into Muscle Tissue of Immunocomponet Mice by Adeno-Associated Virus Vector", *Journal of Virology*, 70(11), (Nov. 1996), 8098-8108.

Yan, Z., "Recombinant AAV-Mediated Gene Delivery Using Dual Vector Heterdimerization", *In: Methods in Enzmology* vol. 346: *Gene Therapy Methods*, Phillips, M. I., Editor, Academic Press, San Diego, CA, (2002), 334-357.

Yan, Z., et al., "Ubiquitination of Both Adeno-Associated Virus Type 2 and 5 Capsid Proteins Affects the Transduction Efficiency of Recombinant Vectors", *Journal of Virology*, 76(5), (2002), 2043-2053.

Bohenzky, R. A., et al., "Sequence and Symmetry Requirements Within the Internal Palindromic Sequences of the Adeno-Associated Virus Terminal Repeat", *Virology*, 166, (1988), 316-327.

Bok, D., "Gene Therapy of Retinal Dystrophies: Achievements, Challenges and Prospects", *Novartis Foundation Symposium 255— Retinal Dystrophies: Functional Genomics to Gene Therapy*, John Wiley & Sons, Ltd.,(2004),4-16; 177-178.

Brister, J. R., et al., "Rep-Mediated Nicking of the Adeno-Associated Virus Orgin Requires Two Biochemical Activities, DNA Helicase Activity and Transesterification", *Journal of Virology*, 73(11), (1999), 9325-9336.

Carter, P. J., et al., "Adeno-Associated Viral Vectors as Gene Delivery Vehicles (Review)", *International Journal of Molecular Medicine*, 6(1), 17-27 (2000).

Chao, H., et al., "Several Log Increase in Therapeutic Transgene Delivery by Distinct Adeno-Associated Viral Serotype Vectors", *Molecular Therapy*, 2(6), (2000), 619-623.

Chiorini, J. A., et al., "Cloning and Characterization of Adeno-Associated Virus Type 5 ", *Journal of Virology*, 73(2), (1999), 1309-1319.

Chiorini, J. A., et al., "Determination of Adeno-Associated Virus Rep68 and Rep78 Binding Sites by Random Sequence Oligonucleotide Selection", *Journal of Virology*, 69(11), (1995), 7334-7338.

Chiorini, J. A., et al., "Sequence Requirements for Stable Binding and Function of Rep68 on the Adeno-Associated Virus Type 2 Inverted Terminal Repeats", *Journal of Virology*, 68(11), (1994),7448-7457.

Rendahl, K. G., et al., "Regulation of Gene Expression in vivo Following Transduction by Two Seperate rAAv Vectors", *Nature Biotechnology*, 16, (1998), 757-761.

Almond, J.B., et al., "The proteasome: a novel traget for cancer chemotherapy", *Leukemia*, 16, (2002), 443-443.

Fürst, R., et al., "Atrial Natriuretic Peptide Induces Mitogen-Activated Protein Kinase Phosphatase-1 in Human Endothelial Cells Via Rac1 and NAD(P) H Oxidase/Nox2-Activation", *Circulation Research*, vol. 96, (1), (2005), 43-53.

Gao, H., et al., "Critical Role of microglial NADPH Oxidase in Rotenone-induced degeneration of Dopaminergic Neurons", *Journal of Neuoscience*; 23(15), (Jul. 16, 2003), 6181-687.

Gao, H., et al., "Critical role of microglial NADPH oxidase-derived free radicals in the in vitro MPTP Model of Parkinson's disease", *The FASEB Journal*, 17(13), (2003), 1954-1956.

Touyz, R. M., et al.,"Expression of a Functionally Active Gp91phox-Containing Neutrophil-type NAD(P) H Oxidase in Smooth Muscle Cells from Human Resistance Arteries: Regulation by Angiotensin II", *Circulation Research*, vol. 90, (11), (Jun. 14, 2002), 1205-1213.

Van Den Worm, E., et al., "Effects of methoxylation of apocynin and analogs on the inhibition of reactive oxygen species production by stimulated human neutophils", *Euro. Jour. of pharm.*;433(2-3), (Dec. 21, 2001), 225-230.

Wu, D. et al., "NADPH-Oxidase in a transgenic mouse model of familial amyotrophic lateral sclerosis", (Abstract Only), Program No. 528.12. Abstract Viewer/Itinerary Planner, (2003), 1 pg.

Wu, D., et al., "The inflammatory NADPH oxidase enzyme modulates neuron degeneration in amyotrophic lateral sclerosis", *Proceedings of Natl. Acad. Sci. USA*; 103(32), (Aug. 8, 2006), 12132-12137.

Rendahl, K. G., et al., "Regulation of Gene Expression in vivo Following Transduction by Two Seperate eAAv Vectors", *Nature Biotechnology*, 16, (1998), 757-761.

Denby, L., et al., "Adeno-associated virus (AAV)-7 and -8 poorly transduce vascular endothelial cells and are sensitive to proteasomal degradation.", *Gene Ther.*, 12(20), (Oct. 2005), 1534-8.

Jennings, K., et al., "Proteasome inhibition enhances AAV-mediated transgene expression in human synoviocytes in vitro and in vivo", *Mol Ther.*, 11(4), (Apr. 2005), 600-7.

Johnson, J. S., et al., "Enhancement of Adeno-Associated Virus Infection by Mobilizing Capsids into and Out of the Nucleolus", *Journal of Virology*, 83(6), (2009), 2632-2644.

Kiyomiya, K-I, et al., "Proteasome is a Carrier to Translocate Doxorubicin From Cytoplasm into Nucleus", *Life Sciences*, 62(20), (1998), 1853-1860.

Abe, Y, et al., "Cytotoxic mechanisms by M239V presenilin 2, a little-analyzed Alzheimer's disease-causative mutant", J. Neurosci Res. 77(4), Abstract Only, (Aug 2004), 583-95.

Alavijeh, Mohammad S, et al., "Drug Metabolism and Pharmacokinetics, the Blood-Brain Barrier, and Central Nervous Systems Drug Discovery", The Journal of the American Societ for Experimental NeuroTherapeutics vol. 2, (Oct. 2005), 554-571.

Gao, H. M, et al., "Novel anti-inflammatory therapy for Parkinson's disease.", Trends Pharmacol Sci., 24(8), (Aug. 2003), 395-401 pgs.

Gao, Hui-Ming, et al., "Distinct Role for Microglia in Rotenone-Induced Degeneration of Dopaminergic Neurons", Journal of Neuroscience 22(3), (Feb. 1, 2002), 782-790.

Hashimoto, Y, et al., "Amino- and carboxyl-terminal mutants of presenilin 1 cause neuronal cell death through distinct toxic mechanisms: Study of 27 different presenilin 1 mutants", J Neurosci Res. 75(3), Abstract Only, (Feb. 2004), 417-28.

He, Y, et al., "Minocycline inhibits microglial activation and protects nigral cells after 6-hydroxydopamine injection into mouse striatum", Brain Res. 909(1-2), Abstract Only, (Aug. 2001), 187-93.

Li, M., et al., "Macrophage colony stimulatory factor and interferon-gama trigger distinct mechanisms for augmentation of beta-amyloid-induced microglia-mediated neurotoxicity", J. Neurochem 91(3), Abstract Only, (Nov. 2004), 1 pg.

Niikura, T, et al., "Characterization of V6421-AbetaPP-induced cytoxicity in primary neurons", J. Neruosci Res. 77(1), Abstract Only, (Jul. 2004), 54-62.

Pardridge, William M, "Blood-Brain Barrier Drug Targeting: The Future of Brain Drug Development", Molecular Interventions 3(2), (Mar. 2003), 90-105.

Wu, Du Chu, et al., "Blockade of Microglial Activation Is Neuroprotective in the 1-Methyl-4-Phenyl-1,2,3,6-Tetrahydropyridine Mouse Model of Parkison Disease", Journal of Neuroscience, (Mar. 1, 2002), 1763-1771.

"DNA Vector-Based siRNA", http://www.genscript.com/rnai_intro.html, (observed Mar. 9, 2004), 3 pgs.

Afione, S. A., et al., "In Vivo Model of Adeno-Associated Virus Vector Persistence and Rescue", Journal of Virolo, 70(5), (May 1996), 3235-3241.

Ali, R. R., et al., "Gene Transfer into the Mouse Retina Mediated by an Adeno-Associated Viral Vector", Human Molecular Genetics, 5(5), (1996), 591-594.

Bartlett, J. S., et al., "Infectious Entry and Adeno-Associated Virus and Adeno-Associated Virus Vectors", Journal of Virology, 74(6), (Mar. 2000), 2777-2785.

Bennett, J., et al., "Real-Time, Noninvasive In Vivo Assessment of Adeno-Associated Virus-Mediated Retinal Transduction", Investigative Ophthalmolgy & Visual Science, 38(13) (Dec. 1997), 2857-2863.

Berns, K. I., et al., "Biology of Adeno-Associated Virus", In: Current Topics in Microbiology and Immunology, 218, (1996), 1-23.

Berns, K. I., "Parvovirus Replication", Microbiological Reviews, 54(3), (Sep. 1990), 316-329.

Bohenzky, R. A., et al., "Interactions Between the Termini of Adeno-Associated Virus DNA", Journal of Molecular Biology, 206, (1989), 91-100.

Bohenzky, R. A., et al., "Replication of Adeno-Associated Virus Genomes With Chimeric Termini", ICN/UCLA Symposium—Viral DNA Replication, (1987), 20 pgs.

Bohenzky, R. A., et al., "Sequence and Symmetry Requirements Wihtin the Internal Palindromic Sequences of the Adeno-Associated Virus Terminal Repeat", Virology, 166 (1988), 316-327.

Bok, D., "Gene Therapy of Retinal Dystrophies: Achievements, Challenges and Prospects", Novartis Foundation Symposium 255—Retinal Dystrophies: Functional Genomics to Gene Therapy, John Wiley & Sons, Ltd.,(2004), 4-16; 177-178.

Brister, J. R., et al., "Rep-Mediated Nicking of the Adeno-Associated Virus Origin Requires Two Biochemical Activities, DNA Helicase Activity and Transesterification", Journal of Virology, 73(11), (1999), 9325-9336.

Carter, P. J., et al., "Adeno-Associated Viral Vectors as Gene Delivery Vehicles (Review)", International Journal of Molecular Medicine, 6(1), 17-27, 2000.

Carter, B. J., et al., "Chapter 11—AAV DNA Replication, Integration, and Genetics", In: Handbook of Parvoviruses, vol. 1., Tijssen, P., Editor, CRC Press, Inc., Boca Raton, FL, (1992), 169-226.

Chao, H., et al., "Several Log Increase in Therapeutic Delivery by Distinct Adeno-Associated Viral Serotype Vectors", Molecular Therapy, 2(6), (2000), 619-623.

Chiorini, J. A., et al., "Cloning and Characterization of Adeno-Associated Virus Type 5", Journal of Virology, 73(2), (1999), 1309-1319.

Chiorini, J. A., et al., "Determination of Adeno-Associated Virus Rep68 and Rep78 Binding Sites by Random Sequence Oligonucleotide Selection",Journal of Virology, 69(11), (1995), 7334-7338.

Chiorini, J. A., et al., "Sequence Requirements for Stable Binding and Function of Rep68 on the Adeno-Associated Virus Type 2 Inverted Terminal Repeats", Journal of Virology, 68(11), (1994), 7448-7457.

Clark, K. R., et al., "Recombinant Adeno-Associated Viral Vectors Mediate Long-Term Transgene Expression in Muscle", Human Gene Therapy, 8, (Apr. 10, 1997), 659-669.

Conrad, C. K., et al., "Safety of Single-Dose Administration of an Adeno-Associated Virus (AAV)-CFTR Vector in the Primate Lung", Gene Therapy, 3(8), (Aug. 1996), 658-668.

Dietrich, C., et al., "p53-Dependent Cell Cycle Arrest Induced by N-acetyl-L-leucinyl-L-leucinyl-L-norleucinal in Platelet-Derived Growth Factor-Stimulated human fibroblasts", Proc. Natl Acad. Sci. USA, 93(20), (1996), 10815-10819.

Duan, D., "A New Dual-Vector Approach to Enhance Recombinant Adeno-Associated Virus-Mediated Gene Expression Through Intermolecular cis Activation", Nature Medicine, 6(5), (2000), 595-598.

Duan, D, et al., "Circular Intermediates of Recombinant Adeno-Associated Virus Have Defined Structural Characteristics Responsible for Long-Term Episomal Persistence in Muscle Tissue", Journal of Virology, 72(11) (1998),8568-8577.

Duan, D., "Consequences of DNA-Dependent Protein Kinase Catalytic Subunit Deficiency on Recombinant Adeno-Associated Virus Genome Cirularization and Heterodimerization in Muscle Tissue", Journal of Virology, 77(8), (2003) 4751-4759.

Duan, D., et al., "Dynamin is Required for Recombinant Adeno-Associated Virus Type 2 Infection", Journal of Virology, 73(12), (Dec. 1999), 10371-10376.

Duan, D., et al., "Endosomal Processing Limits Gene Transfer to Polarized Airway Epithelia by Adeno-Associated Virus", Journal of Clinical Investigation, 105 (Jun. 2000), 1573-1587.

Duan, D., "Expanding AAV Packaging Capacity With Trans-splicing or Overlapping Vectors: A Quantitative Comparison", Molecular Therapy, 4(4), (2001), 383-391.

Duan, D. , "Formation of Adeno-Associated Virus Circular Genomes is Differentially Regulated by Adenovirus E4 ORF6 and E2a Gene Expression", Journal of Virology, 73(1), (Jan. 1999), 161-169.

Duan, D., "Polarity Influences the Efficiency of Recombinant Adenoassociated Virus Infection in Differentiated Airway Epithelia", Human Gene Therapy, 9, (Dec. 10, 1998),2761-2776.

Duan, D , et al., "Response to "Polarity Influences the Efficiency of Recombinant Adenoassociated Virus Infection in Differentiated Airway Epithelia"", Human Gene Therapy, 10, (1999), 1553-1557.

Duan, D., et al., "Structural Analysis of Adeno-Associated Virus Transduction Circular Intermediates", Virology, 261(1), (Aug. 1999), 8-14.

Duan, D., et al., "Structural and Functional Heterogeneity of Integrated Recombinant AAV Genomes", Virus Research, 48(1), (Jan. 1997), 41-56.

Englehardt, J., et al., "Adeno-Associated Virus Vectors and Uses Thereof", U.S. Appl. No. 09/684,554, filed Oct. 6, 2000, 141 pgs.

Englehardt, J., et al., "Compounds and Methods to Enhance rAAV Transduction", U.S. Appl. No. 09/689,136, filed Oct. 12, 2000, 138 pgs.

Fisher, K., et al., "Recombinant Adeno-Associated Virus for Muscle Directed Gene Therapy", Nature Medicine, 3(3), (Mar. 1997), 306-312.

Fisher, K J., et al., "Transduction With Recombinant Adeno-Associated Virus for Gene Therapy is Limited by Leading-Strand Synthesis", Journal of Virology, 70(1), (Jan. 1996), 520-532.

Fisher-Adams, G., et al., "Integration of Adeno-Associated Virus Vectors in CD34+Human Hematopoietic Progenitor Cells After Transduction", Blood, 88(2), (Jul. 15, 1996), 492-504.

Flotte, T., et al., "A Phase I Study of an Adeno-Associated Virus-CFTR Gene Vector in Adult CF Patients With Mild Lung Disease", Human Gene Therapy, 7(9), (1996), 1145-1159.

Flotte, T. R., et al., "Adeno-Associated Virus Vector Gene Expression Occurs in Nondividing Cells in the Absence of Vector DNA Integration", American Journal of Respiratory Cell and Molecular Biology, 11, (1994), pp. 517-521.

Giraud, C., et al., "Recombinant Junctions Formed by Site-Specific Integration of Adeno-Associated Virus into an Episome", Journal of Virology, 69(11), (Nov. 1995), 6917-6924.

Grimm, D., et al., "From Virus Evolution to Vector Revolution: Use of Naturally Occurring Serotypes of Adeno-Associated Virus (AAV) as Novel Vectors for Human Gene Therapy", Current Gene Therapy, 3, (2003), 281-304.

Hagstrom, J. N., et al., "Improved Muscle-Derived Expression of Human Coagulation Factor IX From a Skeletal Actin/CMV Hybrid Enhancer/Promoter", Blood, 95(8), 2000, 2536-2542.

Halbert, C. L., "Transduction by Adeno-Associated Virus Vectors in the Rabbit Airway: Efficiency, Persistence, and Readministration", Journal of Virology, 71(8), (Aug. 1997), 5932-5941.

Hasegawa, S., et al., "Microtubule Involvement in the Intracellular Dynamics for Gene Transfection Mediated by Cationic Liposomes",Gene Therapy, vol. 8, (2001),1669-1673.

Herzog, R. W., et al., "Stable Gene Transfer and Expression of Human Blood Coagulation Factor IX After Intramuscular Injection of Recombinant Adeno-Associated Virus", Proc. Natl. Acad. Sci. USA, 94(11), (May 27, 1997), 5804-5809.

Higgins, D. G., "Clustal: a Package for Performing Multiple Sequence Alignment on a Microcomputer.", *Gene*, 73(1), (Dec. 15, 1988), 237-244.

Higgins, D. G., "Fast and Sensitive Multiple Sequence Alignments on a Microcomputer.", *Comput Appl Biosci.*, 5(2), (Apr. 1989), 151-153.

Kaplan, Johanne M., et al., "Potentiation of gene transfer to the mouse lung by complexes of adenvirus vector and polycations improves therapeutic potential", *Human Gene Therapy*, 9(10), (Jul. 1, 1998),1469-1479.

Kaplitt, M. G., et al., "Long-Term Gene Expression and Phenotypic Correction Using Adeno-Associated Virus Vectors in the Mammalian Brain", *Nature Genetics*, 8, (Oct. 1994), 148-154.

Kay, M. A., et al., "Evidence for Gene Transfer and Expression of Factor IX in Haemophilia B Patients Treated With an AAV Vector", *Nature Genetics*, 24, (2000), 257-261.

Kearns, W. G., et al., "Recombinant Adeno-Associated Virus (AAV-CFTR) Vectors do not Integrate in a Site-Specific Fashion in an Immortalized Epithelial Cell Line", *Gene Therapy*, 3, (1996), 748-755.

Kessler, P D., et al., "Gene Delivery to Skeletal Muscle Results in Sustained Expression and Systemic Delivery of a Therapeutic Protein", *Proc. Natl. Acad. Sci. USA*, 93(24), Nov. 26, 1996, 14082-14087.

Kotin, R. M., et al., "Characterization of a Preferred Site on Human Chromosome 19q for Integration of Adeno-Associated Virus DNA by Non-Homologous Recombination", *The EMBO Journal*, 11(13), (1992), 5071-5078.

Lefebvre, R. B.,et al., "Conformation Takes Precedence Over Sequence in Adeno-Associated Virus DNA Replication", *Molecular and Cellular Biology*, 4(7), (1984), 1416-1419.

Liang, E., et al., "Oligonucleotide Delivery: a Cellular Prospective", *Pharmazie*, 54(8), (Aug. 1999), 559-566.

Linden, R. M., et al., "Site-Specific Integration by Adeno-Associated Virus", *Proc. Natl. Acad. USA*, 93, (Oct. 1994), 11288-11294.

Linden, R. M., et al., "The Recombinant Signals of Adeno-Associated Virus Site-Specific Integration", *Proc. Natl. Acad. Sci. USA*, 93, (Jul. 1996), 7966-7972.

McCarty, D. M., et al., "Identification of Linear DNA Specifically That Specifically Bind the Adeno-Associated Virus Rep Protein", *Journal of Virology*, 68(8), (1994), 4988-4997.

McCarty, D. M., et al., "Interaction of the Adeno-Associated Virus Rep Protein With a Sequence Within the A Palindrome of the Viral Terminal Report", *Journal of Virology*, 68(9), (1994), 4998-5006.

McLaughlin, S.K., et al., "Adeno-Associated Virus General Transduction Vectors: Analysis of Proviral Structures", *Juornal of Virology*, 62(6), (Jun. 1988), 1963-1973.

Musatov, S. A., et al., "Induction of Circular Episomes During Rescue and Replication of Adeno-Associated Virus in Experimental Models of Virus Latency", *Virology*, 275, (2000), 411-432.

Muzyczka, N., "Use of Adeno-Associated Virus as a General Transduction Vector for Mammalian Cells", *In: Current Topics in Microbiology and Immunology*, 158, (1992), 97-129.

Nakai, H., et al., "Helper-Independent and AAV-ITR-Independent Chromosomal Integration of Double-Stranded Linear DNA Vectors in Mice", *Molecular Therepy*, 7(1), (2003), 101-111.

Nakai, H., et al., "Increasing the Size of rAAV-Mediated Expression Cassettes in vivo by Intermolecular Joining of Two Complementary Vectors", *Nature Biotechnology*, 18, (2000), 527-532.

Nakai, H., et al., "Recruitment of Single-Stranded Recombinant Adeno-Associated Virus Vector Genomes and Intermolecular Recombination Are Responsible for Stable Transduction of Liver In Vivo", *Journal of Virology*, 74(20), (2000), 9451-9463.

Ponnazhagan, S., et al., "Lack of Site-Specific Integration of the Recombinant Adeno-Associated Virus 2 Genomes in Human Cells", *Human Gene Therapy*, 8, (Feb. 10, 1997), 275-284.

Puttaraju, M. , et al., "Spliceosome-Mediated RNA trans-splicing as a Tool for Gene Therapy", *Nature Biotechnology*, 17 (3), (Mar. 1999), 246-252.

Qing, K., et al., "Adeno-Associated Virus Type 2-Mediated Gene Transfer: Correlation of Tyrosine Phosphorylation of the Cellular Single-Stranded D Sequence-Binding Protein with Transgene Expression in Human Cells In Vitro and Murine Tissues In Vivo", *Journal of Virology*, 72(2), (Feb. 1998), 1593-1599.

Qing, K., et al., "Human Fibroblast Growth Factor Receptor 1 is a Co-Receptor for Infection by Adeno-Associated Virus 2", *Nature Medicine*, 5(1), (Jan. 1999), 71-77.

Qing, K., "Role of Tyrosine Phosphorylation of a Cellular Protein in Adeno-Associated Virus 2-Mediated Transgene Expression", *Proc. Natl. Acad. Sci. USA*, 94, (Sep. 1997), 10879-10884.

Ramage, A. D., et al., "Improved EBV-Based Shuttle Vector System: Dicistronic mRNA Couples the Synthesis of the Epstein-Barr Nuclear Antigen-1 Protein to Neomycin Resistance", *Gene*, 197(102), (1997), 83-89.

Reich, S. J., et al., "Efficient Trans-Splicing in the Retina Expands the Utility of Adeno-Associated Virus as a Vector for Gene Therapy", *Human Gene Therapy*, 14, (2003), 37-44.

Ryan, J. H., et al., "Sequence Requirements of Binding for Rep68 to the Adeno-Associated Virus Terminal Repeats", *Journal of Virology*, 70(3), (1996), 1542-1553.

Samulski, R. J., et al., "A Recombinant Plasmid from Which an Infectious Adeno-Associated Virus Genome Can Be Excised In Vitro and Its Use to Study Viral Replication", *Journal of Virology*, 61(10), (Oct. 1987),3096-3101.

Samulski, R. J., "Adeno-Associated Virus: Integration at a Specific Chromosomal Locus", *Current Opinion in Genetics & Development*, 3(1), (1993), 74-80.

Samulski, R. J., et al., "Helper-Free Stocks of Recombinant Adeno-Associated Viruses: Normal Integration Does Not Require Viral Gene Expression", *Journal of Virology*, 63 (9), (Sep. 1989), 3822-3828.

Sanlioglu, S., "Loss of ATM Function Enhances Recombinant Adeno-Associated Virus Transduction and Integration Through Pathways Similar to UV Irradiation", *Virology*, 268, (2000) ,68-78.

Schnepp, B. C., et al., "Genetic Fate of Recombinant Adeno-Associated Virus Vector Genomes in Muscle", *Journal of Virology*, 77(6), (2003),3495-3504.

Snyder, R. O., et al., "Features of the Adeno-Associated Virus Origin Involved in Substrate Recognition by the Viral Rep Protein", *Journal of Virology*, 67(10), (1993), 6096-6104.

Snyder, R. O., et al., "Persistent and Therapeutic Concentrations of Human Factor IX in Mice After Hepatic Gene Transfer of Recombinant AAV Vectors", *Nature Genetics*, 16 (Jul. 1997), 270-276.

Srivastava, C. H. et al., "Construction of a Recombinant Human Parvovirus B19: Adeno-Associated Virus 2 (AAV) DNA Inverted Terminal Repeats are Functional in an AAV-B19 Hybrid Virus", *Proc. Natl. Acad. Sci. USA*, 86(20), (1989), 8078-8082.

Summerford, C., et al., "αVβ5 Integrin: a Co-Receptor for Adeno-Associated Virus Type 2 Infection", *Nature Medicine*, 5 (1), (Jan. 1999), 78-82.

Summerford, C., et al., "Membrane-Associated Heparan Sulfate Proteoglycan Is a Receptor for Adeno-Associated Virus Type 2 Virions", *Journal of Virology*, 72(2), (Feb. 1998), 1438-1445.

Teramoto, S., "Factors Influencing Adeno-Associated Virus-Mediated Gene Transfer to Human Cystic Fibrosis Airway Epithelial Cells: Comparison With Adenovirus Vectors", *Journal of Virology*, 72(11), (Nov. 1998), 8904-8912.

Wagner, J. A., et al., "A Phase I/II Study of tgAAV-CF for the Treatment of Chronic Sinusitis in Patients With Cystic Fibrosis", *Human Gene Threrapy*, 9(6), (1998), 889-909.

Wagner, J. A., et al., "Safety and Biological Efficacy of an Adeno-Associated Virus Vector-Cystic Fibrosis Transmembrane Regulator (AAV-CFTR) in the Cystic Fibrosis Maxillary Sinus", *The Laryngoscope*, 109(2, Part 1), (1999), 266-274.

Walsh, C. E., et al., "Phenotypic Correction of Fanconi Anemia in Human Hematopoietic Cells with a Recombinant Adeno-associated Virus Vector", *The Journal of Clinical Investigation*, 94(4) (Oct. 1994), 1440-1448.

Weitzman, M. D., et al., "Adeno-Associated Virus (AAV) Rep Proteins Mediate Complex Formation Between AAV DNA and its Integration Site in Human DNA", *Proc. Nat. Acad. Sci. USA*, 91(13), (1994), 5808-5812.

Westfall, T. D., et al., "The Ecto-ATPase Inhibitor ARL 67156 Enhances Parasympathetic Neurotransmission in the Guinea-Pig Urinary Bladder", *European Journal of Pharmacology*, 329, (1997),169-173.

Wu, P. et al., "Adeno-Associated Virus Vector-Mediated Transgene Integration into Neurons and Other Nondividing Cell Targets", *Journal of Virology*, 72(7), (Jul. 1998),pp. 5919-5926.

Xiao, W., et al., "Adeno-Associated Virus as a Vector for Liver-Directed Gene Therapy", *Journal of Virology*, 72(12), (1998), 10222-10226.

Xiao, Xiao, et al., "Efficient Long-Term Gene Transfer Into Muscle Tissue of Immunocomponent Mice by Adeno-Associated Virology", *Journal of Virology*, 70(11), (Nov. 1996), 8098-8108.

Yan, Z., et al., "A New Class of Hybrid Adeno-Associated Viral Vectors With Non-Homologous ITRs Improves Directional Recombination and Dual-Vector Reconstitution of Large Transgenes", *Molecular Therapy*, 9(Suppl. 1), (2004), S5-S6.

Yan, Z., "Recombinant AAV-Mediated Gene Delivery Using Dual Vector Heterodimerizatiion", *In: Methods in Enxmology, vol. 346: Gene Therapy Methods*, Phillips, M.I., Editor, Academic Press, San Diego, CA,(2002), 334-357.

Yan, Z , et al., "Trans-splicing Vectors Expand the Utility of Adeno-Associated Virus for Gene Therapy", *Proc Natl Acad Sci U S A*, 97(12), (Jun. 6, 2000), 6716-6721.

Yan, Z., et al., "Ubiquitination of Both Adeno-Associated Virus Type 2 and 5 Capsid Proteins Affects the Transduction Efficiency of Recombinant Vectors", *Journal of Virology*, 76(5) 2002 , 2043-2053.

Yang, J. , et al., "Concatamerization of Adeno-Associated Virus Circular Genomes Occurs Through Intermolecular Recombination", *Journal of Virology*, 73(11), (Nov. 1999), 9468-9477.

Zhang, L. N., "Dual Therapeutic Utility of Proteasome Modulating Agents for Pharmaco-Gene Therapy of the Cystic Fibrosis Airway", *Molecular Therapy*, 10(6), (2004), 990-1002.

Lee, K., et al., "Shuttle PCR-based Cloning of the Infectious Adeno-Associated Virus Type 5 Genome", *Journal of Virological Methods*, 111(2), (Aug. 2003), 75-84.

Muramatsu, S., et al., "Nucleotide Sequencing and Generation of an Infectious Clone of Adeno-Associated Virus-3", *Virology*, 221(1), (1996), 208-217.

Xiao, X., et al., "A Novel 165-Base-Pair Terminal Repeat Sequence Is the Sole cis Requirement for the Adeno-Associated Virus Life Cycle", *Journal of Virology*, 71(2), (Feb. 1997), 941-948.

Yan, Z., et al., "Inverted Terminal Repeat Sequences Are Important for Intermolecular Recombination and Circularization of Adeno-Associated Virus Genomes", *Journal of Virology*, 79(1), (Jan. 2005), 364-379.

```
            10          20         30         40
AAV2   1 TTGGCCACTC CCTC------ -TCTGCGCGC TCGCTCGCTC
AAV5   1 CTCTCCCCCC TGTCGCGTTC GCTCGCTCGC TGGCTCGTTT
            50          60         70         80
AAV2  41 ACTGAGGCCG GGCGACCAAA GGTCGCCCGA CGCCCGGGCT
AAV5  41 GGGGGGGTGG CAGCTCAAAG AGCTGCCAGA CGACGGCCCT
            90         100        110        120
AAV2  81 TTGCCCG--- -------GGC GGCCTCAGTG AGCGAGCGAG
AAV5  81 CTGGCCGTCG CCCCCCCAAA CGAGCCAGCG AGCGAGCGAA
           130         140        150        160
AAV2 121 CGCGCAGAGA GGGAGTG-GC CA-ACTCCAT CACTAGGGGT
AAV5 121 CGCGACAGGG GGGAGAGTGC CACACTC--T CAAGCAAGGG
           170
AAV2 161 TCCT
AAV5 161 GGTTTTGT
```

FIG. 7A

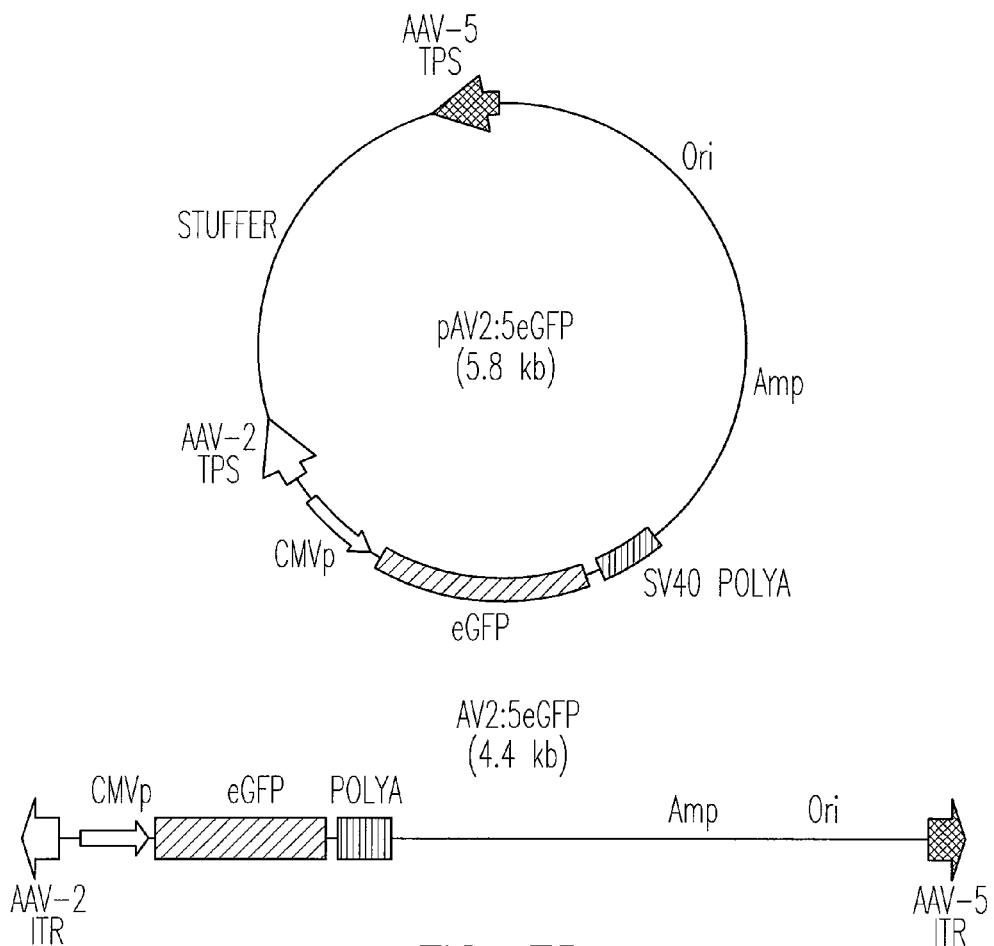

FIG. 7B

```
                1
tctagaAAGGCCTAGGCAGGTGTGGTAA
      GCGGACCAGGCAGGCAGACCCC
      GGCGCGCTATGCGCGCCGGATC
      TCCCCACAAAGTGGGGAGAGGT
      CTGCCTGCCTGGTCCGCTTACCA
      CACCTGCCTAGGCCTTctcgag
```

```
                1
TTGGCCACTCCCTCTCTGCGCGCTC
GCTCGCTCACTGAGGCCGGGCGAC
CAAAGGTCGCCCGACGCCCGGGCT
TTGCCCGGGCGGCCTCAGTGAGCG
AGCGAGCGCGCAGAGAGGGAGTGG
CCAACTCCATCACTAGGGGTTCCT
   ↑
   125                    145
```

```
              10         20         30         40
PSEUDO TPS  1 AAGGCCTAGG CAGGTGTGGT AAGCGGACCA GGCAGGCAGA
AAV2 ITR    1 TTGGCC-ACT CCCTCTCTGC GCGCTCGCTC GCTCACTGAG 50         60         70         80
PSEUDO TPS 41 CCCCGGCGCG CTATGCGCGC CGGATCTCCC CACAAAGTGG
AAV2 ITR   41 GCCGGGCGAC CAAAGGTCGC CCGACGCCCG GGCTTTGCCC 90        100        110        120
PSEUDO TPS 81 GGAGAGGTCT GCCTGCCTGG TCCGCTTACC ACACCTGCCT
AAV2 ITR   81 GGGCGGCCTC AGTGAGCGAG CGAGCGCGCA GAGAGGGAGT 130        140        150
PSEUDO TPS 121 AGGCCTT
AAV2 ITR   121 -GGCCAACTC CATCACTAGG GGTTCCT
                   ↑
```

FIG. 13C

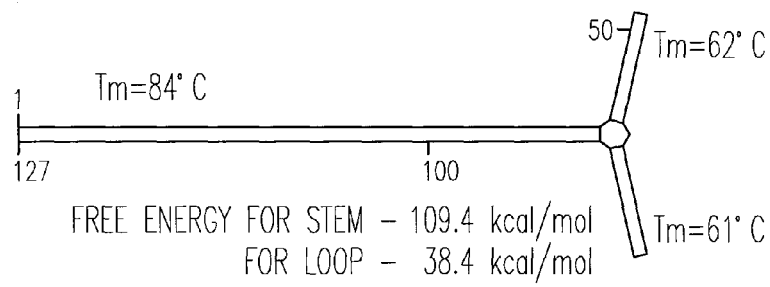

FIG. 13D

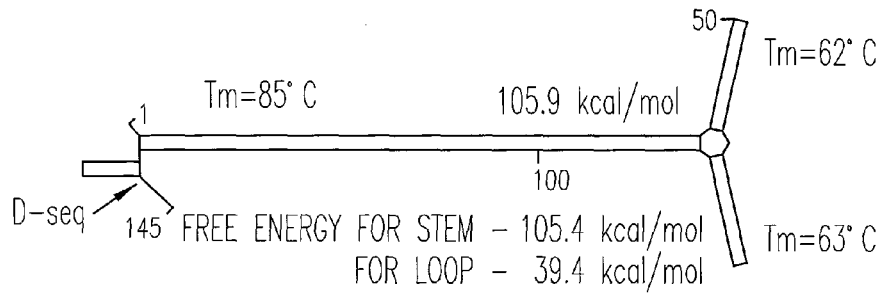

FIG. 13E

AV.P:2-donor +AV.2:P-acpt

AV2:P-donr +AV.P:2-acpt

AV.P:2-donor +AV.2:P-acpt

AV2:P-donr +AV.P:2-acpt

FIG. 15B

AAV-2 TPS

Pseudo TPS

AAV-5 TPS

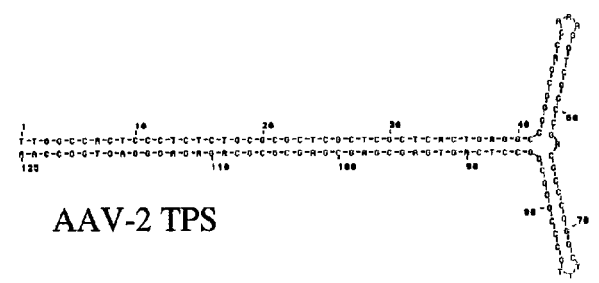
AAV-2 TPS
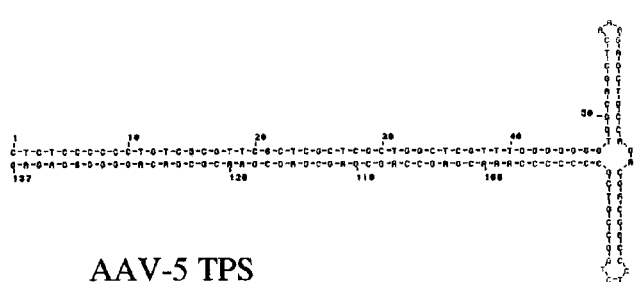
AAV-5 TPS
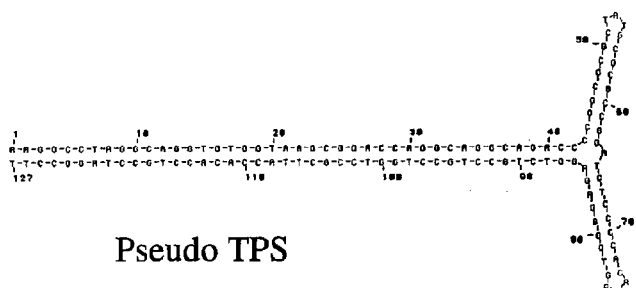
Pseudo TPS
FIG. 16G
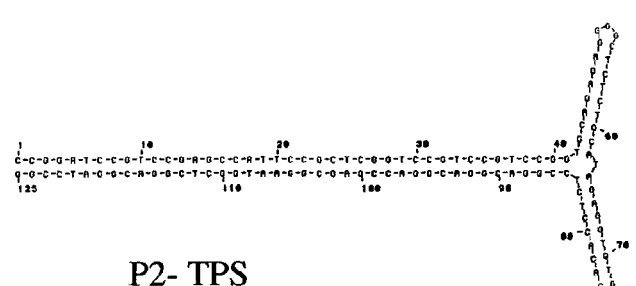
P2- TPS
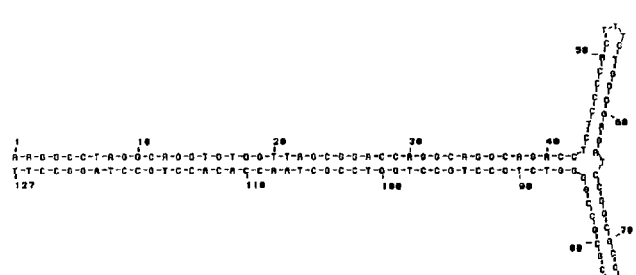
P3- TPS

| TPS | FULL SEQ | | A-A' stem | | B-B'-C'-C LOOP | | B ARM ONLY | | C ARM ONLY | |
|---|---|---|---|---|---|---|---|---|---|---|
| | SECONDARY STRUCTURE FREE ENERGY | G-C% | Tm | G-C% | Tm | G-C% | Tm | G-C% | Tm | G-C% | Tm |
| AAV-2 | -161.5kcal/mol | 72% | 89°C | 68% | 84°C | 88% | 83°C | 77% | 62°C | 77% | 61°C |
| PSEUDO | -162.2kcal/mol | 66% | 87°C | 63% | 85°C | 71% | 79°C | 83% | 62°C | 62% | 61°C |
| P2 | -145.5kcal/mol | 69% | 88°C | 64% | 86°C | 62% | 75°C | 64% | 60°C | 64% | 60°C |
| P3 | -162.2kcal/mol | 66% | 87°C | 63% | 85°C | 71% | 79°C | 59% | 59°C | 77% | 70°C |
| N1 | -133.5kcal/mol | 53% | 81°C | 38% | 72°C | 88% | 83°C | 77% | 62°C | 77% | 61°C |
| N2 | -118.5kcal/mol | 45% | 78°C | 38% | 72°C | 58% | 74°C | 59% | 59°C | 59% | 59°C |

FIG. 17

ADENO-ASSOCIATED VIRUS VECTORS WITH INTRAVECTOR HETEROLOGOUS TERMINAL PALINDROMIC SEQUENCES

CROSS-REFERENCE TO RELATED APPLICATIONS

This application is a continuation in part of U.S. application Ser. No. 10/194,421, filed Jul. 12, 2002, now abandoned which claims the benefit of the filing date of U.S. application Ser. No. 60/305,204, filed Jul. 13, 2001, under 35 U.S.C. §119(e), the disclosures of which are incorporated by reference herein in their entirety.

STATEMENT OF GOVERNMENT RIGHTS

This invention was made, at least in part, with a grant from the Government of the United States of America (grants HL58340 and DK54759 from the National Institutes of Health). The Government may have certain rights in the invention.

BACKGROUND OF THE INVENTION

Adeno-associated virus (AAV) is a single-stranded DNA parvovirus with a helper-dependent life cycle that replicates in the presence of helper viruses such as adenovirus or herpes virus (Berns et al., 1996; Carter et al., 2000). The type 2 AAV (AAV-2) DNA genome is 4681 nucleotides long and includes an identical 5' and 3' copy of a 145 nucleotide long inverted terminal repeat (ITR) and a unique sequence of 4391 nucleotides that contains two main open reading frames for the rep and cap genes (Srivastava et al., 1983; Smuda et al., 1991). This unique region contains three transcription promoters $p_5$, $p_{19}$, and $p_{40}$ that are used to express the rep and cap genes. The ITRs contain palindromic sequences capable of forming a secondary stem loop structure and are required in cis to provide functional origins of replication (ori). In addition, AAV ITRS also provide sequences necessary for encapsidation, integration, and rescue of the rAAV from either host cell chromosomes or recombinant plasmids. AAV ITR sequences function in two distinct aspects. First, as described above, ITR sequences are required for AAV production, assembly and packaging. Secondly, AAV ITRs function in the persistence and expression of a linked transgene in a host cell.

In a productive AAV infection in the presence of a helper such as adenovirus, the infecting parental AAV single strand genome is converted to a parental duplex replicating form (RF) by a self-priming mechanism as a result of the ability the ability of the ITR to form a hairpin structure (Muzyczka, 1992; Carter et al., 1989). The parental RF molecule is then amplified to form a large pool of progeny RF molecules in a process that requires both helper functions and the AAV rep gene products, Rep78 and Rep68. AAV RF genomes are a mixture of head-to-head or tail-to-tail multimers or concatamers, and are precursors to progeny single strand (SS) DNA genomes that are packaged into pre-formed empty AAV capsids. Rep52 and Rep40 interact with the pre-formed capsid to provide a DNA helicase function for DNA packaging (Myers et al., 1980; King et al., 2001).

The kinetics of AAV replication and assembly has been investigated. In human HeLa or 293 cells simultaneously infected with AAV and adenovirus, there are three phases of the growth cycle. In the first 8 to 10 hours, the cell becomes permissive for AAV replication as a result of expression of a subset of adenovirus genes including E1, E2A, E4 and the VA RNA. During this period, the infecting AAV genome is converted to the initial parental duplex RF DNA by self-priming from the terminal base-paired 3' hydroxyl group provided by the ITR, which can form a self-paired hairpin. This initial generation of a duplex genome also provides a template for transcription and expression of AAV proteins. In a second phase, from about 10 to 20 hours after infection, the bulk of the AAV rep and cap proteins are synthesized, and there is a large amplification of monomeric and concatameric duplex AAV RF genomes to a constant level. During the third phase of AAV growth, between 16 to 30 hours, single strand progeny molecules are synthesized by a strand-displacement replication mechanism and packaged into pre-formed capsids followed by accumulation of mature, infectious AAV particles (Redemann et al., 1998; Carter et al., 1989). Rep68 and Rep78 bind to the ITR and are site-specific, strand-specific endonucleases that cleave the hairpin in an RF molecule at the site that is the 5' terminus of the mature strand. In addition, these proteins contain an ATP-binding site which is important for enzymatic activity but not for binding to the ITR. Further, Rep78 and 68 have both DNA and RNA helicase activity. Rep proteins also regulate transcription (Muzyczka; 1992; Carter et al., 1992; Flotte et al., 1995; Hallek et al., 1998; Flotte et al., 1996). Rep78 is a negative auto-regulator of the p5 promoter, i.e., of its own synthesis, but is an activator of the p40 promoter to enhance capsid protein production. Rep52 and Rep40 do not bind to the ITR but provide a helicase in assembly of mature particles. Also, the smaller rep proteins are anti-repressors and block the negative auto-regulation of p5 by Rep78. rAAV vectors which contain only the 5' and 3' ITR sequences flanked by the transgene of interest are replicated analogous to wild-type AAV except rep and cap functions are provided to the permissive cell in trans.

In the absence of selective pressure, recombinant AAV (rAAV) vectors generally persist as episomal genomes. A number of studies have now shown that rAAV vectors can persist for extended periods of time when administered in vivo and that the predominant form of the persisting vector genomes appears to be multimeric structures which are head-to-tail concatamers that are circular. How these head-to-tail multimers are formed is unknown but it cannot involve the normal AAV replication process because that requires rep protein and gives only head-to-head or tail-to-tail concatamers. Whether the circular concatemers are integration intermediates, as has been suggested for AAV integration, is also unknown. However, available evidence indicates that the majority of these head-to-tail concatamers are episomal and that integrated copies of vector in organs such as liver or muscle are very rare (Flotte et al., 1993; Afione et al., 1996; Kaplitt et al., 1994; Xiao et al., 1996; Kessler et al., 1996; Koerberl et al., 1997; Ponnazhagan et al., 1997; Zadori et al., 2001; Fisher et al., 1997; Herzog et al., 1997; Snyder et al., 1997; Miao et al., 1998; Duan et al., 1998; Duan et al., 1999; Vincent-Lacaze et al., 1999; McKeon et al., 1996; Nakai et al., 2001; Schnepp et al., 2003.)

rAAV-based vector systems have attracted great attention for human gene therapy for more than 10 years. Although rAAV vectors have now been generated from eight different serotypes (Chao et al., 2000; Grimm et al., 2003), rAAV-2 has been most extensively studied as a gene transfer vector, and has been used in clinical trials for cystic fibrosis (Flotte et al., 1996; Wagner et al., 1999; Wagner et al., 1998) and hemophilia B (Hagstrom et al., 2000; Kay et al., 2000). Over the last decade, knowledge of the molecular virology of AAV has expanded significantly. Insights into various aspects of receptor interactions, intercellular trafficking, and genome conversion have led to improvements in the design and performance of rAAV vector systems. For example, studies evaluating the molecular mechanisms of rAAV-2 genome conversion have uncovered unique mechanisms of latent viral genome persistence that involve linear and/or circular concatamerization (Duan et al., 1998; Yang et al., 1999). Studies evaluating the molecular mechanisms of rAAV genome concatamerization have demonstrated that this process occurs through intermolecular joining of two independent viral genomes as opposed to self-priming replication (Yang et al., 1999). This important discovery has lead to development of dual vector heterodimerization approaches to deliver transgene cassettes that exceed the 4.7 kb packaging limitation of rAAV vectors. This innovative approach utilizes two independent vectors to deliver separately encoded transgene exons to the same cell, which vectors are capable of reconstituting a transgene product by trans-splicing across heterodimer genomes formed by intermolecular recombination (Yan et al., 2002). Such an approach has effectively doubled the capacity of a single AAV vector and has been successfully tested with reporter genes in muscle (Duan et al., 2000; Sun et al., 2000; Yan et al., 2000), liver (Nakai et al., 2003), eyes (Reich et al., 2003), and lung. These studies have paved the way for applications of dual trans-splicing vectors for diseases such as cystic fibrosis, Duchenne muscular dystrophy, and hemophilia A, all of which require the delivery of large cDNA expression cassettes which approach or exceed the packaging capacity of a single rAAV vector.

Despite the promising prospects of dual rAAV vector approaches, the level of gene expression from the current system remains substantially lower than delivery of a transgene encoded within a single vector. Several factors currently limit the efficiency of dual vector heterodimerization approaches. First, the multiplicity of infection must be high enough such that both delivered vectors infect the same cell. Second, in the context of dual vector trans-splicing approaches, the generation of a functional transgene is directionally dependent on the joining of two viral genomes in the correct orientation. For dual vectors containing two minigene exons in the same orientation, only heterodimers formed by a tail to head (T-H) recombination event are capable of yielding an active reconstituted transgene product via trans-splicing. While approaches aimed at increasing the ratio of T-H oriented heterodimers and larger concatamers could conceivably improve the efficiency of dual vector trans-splicing delivery of transgene products, the mechanisms responsible for intermolecular recombination of rAAV genomes remain poorly understood. Previous studies in muscle have suggested that monomer circular viral genome intermediates with double-D structure may be precursors to the formation of episomally stable concatamers (Duan et al., 1998; Yan et al., 2000). In these studies, intermolecular recombination appeared to occur between monomer circular genomes in a time-dependent manner leading to high molecular weight circular concatamers. In contrast, studies in liver with rAAV and linear AAV-like genomes have suggested that concatamerization may be independent of the ITR and primarily involve linear intermolecular end-end ligation (Nakai et al., 2003; Nakai et al., 2000). A clear delineation of these two mechanisms as well as potential tissue-specific differences in the molecular structure of concatamers may be important to improve the efficiency of rAAV dual vector approaches.

What is needed is a method to increase the efficiency of rAAV vectors in general as well as rAAV dual vector technologies.

SUMMARY OF THE INVENTION

The present invention provides a set of rAAV vectors having terminal palindromic sequences (TPSs) flanking a sequence of interest which vectors, when introduced to a host cell, host cell lysate, or host result in an increase in the formation of head-to-tail (or tail-to-head) concatamers, e.g., within the nucleus of a cell, due to directional intervector homology between at least one TPS in each of the vectors. Unlike rAAV vectors known in the art which have intravector homologous 5' and 3' TPSs, the present invention provides for at least one of the vectors in a set to include a rAAV vector which contains heterologous 5' and 3' TPSs (referred to herein as an intravector heterologous TPS AAV vector) flanking a nucleic acid segment of interest. As used herein, a "terminal palindromic sequence" or "TPS" is a palindromic sequence (PS) which is present at the 5' or 3' end of an AAV vector, that is capable of forming a secondary structure, optionally a stem or stem-loop structure found in native AAV TPSs, and, when present in a viral genome, does not substantially inhibit the packaging or replication of that genome, and/or provirus rescue, i.e., an intravector heterologous TPS rAAV vector is capable of being packaged and replicated in the presence of appropriate viral and/or cellular proteins. For example, intravector heterologous TPSs have less than 80%, including less than 70%, 60%, 50%, 40%, 30%, 20%, 10%, or 5%, or no, nucleic acid sequence identity to each other, and in one embodiment, at least one TPS in a vector has less than 80%, including less than 70%, 60%, 50%, 40%, 30%, 20%, 10%, or 5%, or no, nucleic acid sequence identity to sequences in native AAV TPSs which form a secondary structure. It is within the skill of the art to determine the nucleic acid and amino acid sequence identity or homology of a polynucleotide or polypeptide sequence relative to a reference sequence. As used herein, "directional intervector homology" refers to an orientation of the nucleic acid sequence of a 5' TPS or 3' TPS of one vector of a set of two or more vectors, with a 3' TPS or 5' TPS, respectively, of a second vector of the set, wherein the 5' TPS or 3' TPS of the first vector and the 3' TPS or 5' TPS of the second vector are homologous, i.e., the homologous TPSs are in a head-to-tail or tail-to-head orientation. Optionally, the 5' TPS of the first vector and the 3' TPS of the second vector are homologous and the 3' TPS of the first vector and the 5' TPS of the second vector are homologous.

Thus, at least one of the rAAV vectors in a set has heterologous TPSs, and at least one TPS in one vector in a set is homologous to one TPS in another vector of the set, i.e., there is intervector TPS homology. Homologous PSs are PSs which have sufficient sequence homology so that when present in a single vector in a cell, cell extract or host, they undergo intramolecular recombination at an increased efficiency relative to intravector heterologous PSs, e.g., homologous PSs have at least 80% or more, e.g., 85%, 90%, 95% and up to 100%, nucleic acid sequence identity to each other, thereby facilitating recombination between those PSs. Homologous PSs may be used to refer to homology of the PS in ITRs found in native AAV ITR serotypes or the PS of other parvoviruses.

A PS useful in the present vectors thus includes a native PS (i.e., a sequence found in nature) such as the PS in the ITR of AAV or another parvovirus such as human B19 parvovirus, canine parvovirus or minute virus of mouse, a PS found in viruses other than AAV, such as a PS from adenovirus or poxvirus such as vaccinia virus, as well as a synthetic sequence (i.e., one not found in nature) referred to herein as a pseudo PS, and modified forms thereof, e.g., a PS with an insertion of a sequence having or encoding an activity, for instance, a promoter, enhancer, integration site for an integrase, e.g., sites for Cre or Flp recombinase, an open reading frame for a gene product, or combinations thereof. Accordingly, a "pseudo PS" is a palindomic DNA sequence, including an imperfect palindromic sequence, which shares less than 80% including less than 70%, 60%, 50%, 40%, 30%, 20%, 10%, or 5%, or no, nucleic acid sequence identity to sequences in native AAV TPSs which form a secondary structure.

In one embodiment, a rAAV vector with heterologous TPSs (a "first" rAAV vector) flanking a nucleic acid segment of interest, when introduced with one or more rAAV vectors which have directional intervector homology with either the 5' and/or 3' TPS of the first rAAV vector as well as a different nucleic acid sequence of interest to a cell, cell lysate or host, results in an increase in the formation of head-to-tail concatamers and the directional orientation of the nucleic acid segments of interest, i.e., in the same 5' to 3' orientation. Thus, the introduction of a set of vectors of the present invention containing directional TPSs to a host cell, host cell lysate, or host produces an increase in the ratio, number, persistence, and/or transcriptional activity of head-to-tail concatamers, relative to a single vector set containing homologous TPSs or a single vector set containing heterologous TPSs which, when introduced to a host cell, host cell lysate or host results in a mixture of head-to-head, tail-to-tail and head-to-tail concatamers. An increase in head-to-tail concatamer formation can yield an increase or persistence of expression of the nucleic acid segment(s) of interest in a host cell, host cell lysate, or a host which contains the vectors of the present invention.

Therefore, as a result of the reduced or lack of 5'-3' TPS sequence identity in intravector heterologous TPS rAAV vectors, in a cell or extract thereof, the intravector heterologous TPS rAAV vector has a reduced efficiency of forming circular monomers via intramolecular recombination relative to a corresponding rAAV vector with homologous TPSs. For instance, vectors with intravector heterologous TPSs, when present in a cell, have a reduced capacity, e.g., at least a 10-fold, 20-fold, 50-fold, 60-fold or more reduced capacity, to form circular genomes relative to a vector with corresponding intravector homologous TPSs, e.g., a vector in which the 5' and 3' TPSs have sequence identity.

Accordingly, the present invention provides a rAAV vector which includes a 5' TPS and a 3' TPS which flank a nucleic acid segment of interest which may include regulatory elements, at least one AAV genome encapsidation signal such as a native AAV D-sequence and/or optionally a heterologous (e.g., non-AAV) sequence or structure which interacts with the appropriate Rep proteins to wind the single strand rAAV genome into a preformed rAAV capsid (encapsidation function), e.g., a P1 sequence (see WO 00/65038), and at least one site, conformation, or secondary structure which functions as an AAV ITR terminal resolution site ("trs") sequence, and can be recognized by an AAV Rep protein, and can be cleaved by Rep to yield AAV genomes which can be packaged efficiently into a viral capsid, and wherein, for an intravevctor heterologous TPS vector, the 5' TPS and 3' TPS within the rAAV vector are not symmetrical, i.e., they do not have 100% sequence complementarity. Thus, for example, a vector with a 5' TPS from an AAV-2 genome (which lacks a D-sequence for the comparison) and a 3' TPS from an AAV-5 genome (which lacks a D-sequence for the comparison) is a vector with heterologous TPSs. One of ordinary skill in the art will appreciate that the encapsidation and terminal resolution sites are required within the TPS sequence for production of infectious viral progeny and may be deleted from a gene therapy rAAV vector delivered to a host cell if alternate methods of cleaving and encapsidating vectors are provided in trans.

When utilized in dual vector approaches as described in U.S. Pat. No. 6,436,392 and WO 01/25465, an intravector heterologous TPS rAAV vector may be employed with one or more other rAAV vectors to transfer nucleic acid segments of interest, e.g., genetic elements such as transgenes, to cells. In one embodiment, rAAV vectors of the invention are constructed with directional intervector homology, e.g., the 3' TPS of a first rAAV vector is homologous to the 5' TPS of a second rAAV vector (which optionally is an intravector heterologous TPS vector) such that the nucleic acid segment between the 5' and 3' TPSs of each vector become linked in a 5'-3' orientation to the TPSs after introduction to a cell, cell lysate or host, wherein at least one of the vectors is an intravector heterologous TPS AAV vector. Alternatively, the nucleic acid segments flanked by the TPSs in two vectors with intervector TPS homology may both be in antisense orientation to the TPS. In one embodiment, one of the rAAV vectors in the set is an intravector homologous TPS AAV vector. In one embodiment, more than two rAAV vectors are employed in the set, at least one of which is an intravector heterologous TPS AAV vector and at least two of which have intervector TPS homology such that the nucleic acid segments between the TPSs in the vectors become directionally oriented (5'-3' or 3'-5') once those vectors are present in a cell or cell extract due to intermolecular recombination.

Thus, intravector TPS heterology in two or more appropriately selected rAAV vectors of a set, e.g., a first AAV vector is an intravector heterologous TPS AAV vector and a second rAAV vector, which optionally is an intravector heterologous TPS vector, has one TPS that is homologous to one of the TPSs in the first rAAV vector, can increase the yield of head-to-tail concatamers (a chimeric DNA molecule), e.g., linear concatamers, via directional intermolecular recombination. For example, a first intravector heterologous TPS rAAV vector having a 5' TPS (sequence 1) linked to a first nucleic acid segment of interest, e.g., genetic regulatory sequences, or an open reading frame or a portion thereof, and a 3' TPS (sequence 2), and a second intravector heterologous TPS rAAV vector having a second 5' TPS (sequence 2) linked to a second nucleic acid segment of interest linked to a second 3' TPS (sequence 1), after introduction to a cell, may undergo directional homologous recombination, as has been described in the art but may also occur by other mechanisms such as strand fill in after homologous TPSs anneal, yielding a chimeric DNA molecule including sequences from each vector in the following orientation: 5' sequence 1 linked to the first nucleic acid segment linked to at least a portion of sequence 2 linked to the second nucleic acid segment linked to sequence 1 which optionally at least portion of is linked to the first nucleic acid segment linked to at least a portion of sequence 2 linked to the second nucleic acid segment linked to sequence 13'. Similarly, three (or more) different intravector heterologous TPS AAV vectors may be employed. For example, a first intravector heterologous TPS rAAV vector having a 5' TPS (sequence 1) linked to a first nucleic acid segment of interest, e.g., genetic regulatory sequences, or an open reading frame or a portion thereof, and a 3' TPS (sequence 2), a second intravector heterologous TPS rAAV vector having a second 5' TPS (sequence 2) linked to a second nucleic acid segment of interest linked to a second 3' TPS (sequence 3), a third intravector heterologous TPS rAAV vector having a third 5' TPS (sequence 3) linked to a third nucleic acid segment of interest linked to a third 3' TPS (sequence 1), after introduction to a cell, may undergo directional intermolecular recombination, yielding a chimeric DNA molecule including sequences from each vector in the following orientation: 5' sequence 1 linked to the first nucleic acid segment linked to at least a portion of sequence 2 linked to the second nucleic acid segment linked to at least a portion of sequence 3 linked to the third nucleic acid segment which is optionally linked to at least portion of sequence 1 linked to the first nucleic acid segment linked to at least a portion of sequence 2 linked to the second nucleic acid segment linked to at least a portion of sequence 3 linked to the third nucleic acid segment linked to sequence 13'. Thus, as has been described in the art, recombination between TPSs in AAV vectors may result in insertions and/or deletions in or near the recombination site.

As described herein, mechanisms by which TPS sequences mediate intermolecular recombination of AAV genomes were evaluated with the goal of engineering more efficient vectors capable of reconstituting large transgenes delivered by a dual vector trans-splicing approach or reducing the formation of single circle AAV genomes (circular monomers). To this end, a novel intravector heterologous TPS AAV vector characterized by an AAV-2 TPS and an AAV-5 TPS at either end of the viral genome was generated. This intravector heterologous TPS genome was efficiently packaged into either AAV-2 or AAV-5 capsids to generate infectious virions. Intravector heterologous AV2:5 TPS viruses had a significantly reduced capacity to form circular intermediates in infected cells, as compared to intravector homologous AV2:2 TPS vectors and intravector homologous AV5:5 TPS vectors, despite their similar capacity to express an encoded EGFP transgene.

To examine whether the divergent TPS sequences contained within intravector heterologous AV2:5 TPS vectors could direct intermolecular concatamerization in a head-to-tail fashion, two intravector heterologous TPS trans-splicing vectors (AV5:2 LacZdonor and AV2:5 LacZacceptor) were generated, where each delivered one exon of a β-galactosidase minigene flanked by donor or acceptor splice sequences. These intravector heterologous TPS trans-splicing AAV vectors were compared to intravector homologous TPS trans-splicing AAV vector sets (AV5:5 and AV2:2) for their efficiency to reconstitute β-galactosidase gene expression. Results from this comparison demonstrated that intravector heterologous TPS dual vector sets had a significantly enhanced trans-splicing efficiency (6 to 10 fold, depending on the capsid serotype) as compared to intravector homologous TPS AAV vectors. Molecular studies of viral genome structure suggested that intravector heterologous TPS AAV vectors provide more efficient directional concatamerization (also referred to in the art as recombination) due to an increased abundance of linear form genomes. Without wishing to be bound by theory, circular concatamerzation of rAAV genomes in a host cell, or host extract has been described in the art to occur via intervector homologous recombination. For vectors which have intravector homologous TPSs, that event can yield head-to-head, head-to-tail or tail-to-tail structures. The rAAVs of the present invention containing intravector heterologous TPSs and intervector homologous TPSs undergo directional concatamerization or directional recombination such that intervector homology directs the orientation of the recombination event with respect to the 5' to 3' orientation of the nucleic acid segments in different vectors. These studies accordingly provide direct evidence for the importance of TPS sequences in directing intermolecular and intramolecular homologous recombination of AAV genomes. Moreover, the use of intravector heterologous TPS AAV vector genomes provides new strategies to manipulate viral genome conversion products and direct intermolecular recombination events, e.g., ones for efficient dual AAV vector reconstitution of transgenes. Further, the use of intravector heterologous TPS rAAV vectors may result in an increased efficiency of expression of the encoded gene product, e.g., by 2-fold, 3-fold, 6-fold, 10-fold, 20-fold or more, relative to one or more corresponding intravector homologous TPS rAAV vectors.

An intravector heterologous TPS AAV vector optionally has a similar capacity (efficiency) to transduce cells as a native rAAV vector i.e., a single vector with homologous TPSs, and can be used as a gene transfer vector, e.g., to deliver an intact nucleic acid expression cassette, which vector may have altered, e.g., enhanced genome stability and/or transcriptional activity due to altered vector genome structure in a cell, for instance due to an increase in linear forms, even in the absence of another AAV vector with a 5' TPS that is homologous to the 3' TPS in the intravector heterologous TPS AAV vector, or the absence of another AAV vector with a 3' TPS that is homologous to the 5' TPS in the intravector heterologous TPS vector. However, unlike rAAV vectors which are capable of forming circular intermediates in infected cells, i.e., those with intravector homologous TPSs, the transduction of cells by an intravector heterologous TPS AAV results in an increase of the abundance of linear form genomes. Moreover, the transduction biology of the intravector heterologous TPS rAAV vectors may differ from that of homologous TPS rAAV vectors in the following characteristics: rates of genome conversion or turn-over, episomal persistence and chromosomal integration in the transduced cells. These differences imply that the intravector heterologous TPS rAAV vector might be a more efficient transgene vehicle to transduce some special tissue or organ such as liver, in which it was reported that rAAV preferred to persist as linear concatamers, or integrate into the chromosome. Additionally, the ability to alter the complete sequence in the TPS in intravector heterologous TPS vectors allows the incorporation of functional elements in the TPS. Such elements could also be placed directionally at either end of the transgene genome. Functional elements could include those which affect expression of transgenes (i.e., regulatory elements including promoters), those which affect integration (i.e., sequences which target the action of functionally expressed integrase proteins), or sequences which are sites of action of endogenous or recombinantly expressed proteins which drive recombination between viral genomes to enhance directional recombination (i.e., CRE, transposons, and the like). Accordingly, one method of altering viral genome structure is through modification of TPSs responsible for directing genome conversion to transcriptionally active states. The same modifications may also enhance dual vector approaches by directing recombinational events.

Therefore, the invention provides a set of at least two rAAV or a composition comprising at least two rAAV. A first rAAV includes a first recombinant DNA molecule comprising linked: a first DNA segment comprising a first 5' TPS; a second DNA segment comprising a nucleic acid segment of interest, i.e., a segment not derived from AAV, for example, a segment which does not encode an AAV protein or portion thereof; and a third DNA segment comprising a first 3' TPS. The set or composition also includes a second rAAV which includes a second recombinant DNA molecule comprising linked: a first DNA segment comprising a second 5' TPS; a second nucleic acid segment of interest which is different than the nucleic acid segment of interest in the first rAAV vector; and a third DNA segment comprising a second 3' TPS. At least one of the vectors is an intravector heterologous TPS AAV vector and at least the 3' TPS in one vector is homologous to the 5' TPS in the other vector. Optionally, both vectors are intravector heterologous TPS AAV vectors. In one embodiment, a first rAAV includes a first recombinant DNA molecule comprising linked: a first DNA segment comprising a 5' AAV TPS; a second DNA segment comprising a nucleic acid segment of interest and a third AAV segment comprising a 3' TPS, wherein the 5' AAV TPS and 3' TPS in the first are heterologous TPSs, i.e., the rAAV is an intravector heterologous TPS AAV. The set or composition also includes a second rAAV which includes a second recombinant DNA molecule comprising linked: a first DNA segment comprising a 5' TPS; a second DNA segment comprising a nucleic acid segment of interest which is different than the nucleic acid segment of interest in the first recombinant DNA molecule; and a third DNA segment comprising a 3' AAV TPS, wherein the 5' TPS and 3' TPS in the second AAV are optionally heterologous TPSs, and wherein the 3' TPS of the first recombinant DNA molecule is homologous to the 5' TPS of the second recombinant molecule. In yet another embodiment, a first rAAV includes a first recombinant DNA molecule comprising linked: a first DNA segment comprising a 5' TPS; a second DNA segment comprising a nucleic acid segment of interest; and a third DNA segment comprising a 3' AAV TPS, wherein the 5' TPS and 3' AAV TPS in the first rAAV are heterologous TPSs. The set or composition also includes a second rAAV which includes a second recombinant DNA molecule comprising linked: a first DNA segment comprising a 5' AAV TPS; a second nucleic acid segment of interest which is different than the nucleic acid segment of interest in first recombinant DNA molecule; and a third DNA segment comprising a 3' TPS, wherein the 5' AAV TPS and 3' TPS in the second rAAV are heterologous TPSs, and wherein the 3' AAV TPS of the first rAAV is homologous to the 5' AAV TPS of the second rAAV. At least one of the second nucleic acid segments encodes a functional gene product, i.e., one with a detectable activity or one capable of having an activity when present in an appropriate cell, tissue or organism, or the two second DNA segments together encode a functional gene product. Within the scope of the invention is the inclusion of more than one open reading frame in a vector of the invention, a open reading frame and a portion of another open reading frame in an individual vector, or set of vectors, and/or one or more transcriptional regulatory elements in an individual vector, or set of vectors. A set or composition including two or more rAAV vectors, or each individual rAAV vector separately, may be delivered to a host cell, e.g., via infection, liposomes, as a plasmid or a virosome, so as to result in a host cell in which at least two homologous TPSs in two different rAAV vectors have undergone intermolecular recombination to generate a chimeric DNA molecule (the product of the intermolecular recombination) that encodes one or more functional gene products. Thus, the vectors may be contacted with a cell simultaneously or sequentially. Moreover, it is envisioned that the amount of each vector in a set of vectors that includes at least two different vectors, that is contacted with a cell may be the same, i.e., a ratio of 1:1, or any other ratio, e.g., 1:1.2, 1:1.5, 1:1.75, 1:2, or more, e.g., 1:3, 1:5, or 1:10, and that one or more of the vectors may be recontacted with the cell (repeat delivery), so long as the desired effect is achieved, e.g., expression or the regulation of expression of at least one nucleic acid segment in one of the vectors.

In one embodiment, one rAAV vector includes a first DNA segment comprising a first 5' TPS linked to a nucleic acid segment of interest comprising a promoter operably linked to a open reading frame linked to a DNA segment comprising a first 3' TPS, wherein the first 5' TPS and first 3' TPS are heterologous TPSs. A second rAAV vector includes a first DNA segment comprising a second 5' TPS linked to a second nucleic acid segment of interest comprising a second promoter operably linked to a second open reading frame linked to a third DNA segment comprising a second 3' TPS, wherein the second 5' TPS and second 3' TPS in the second rAAV are optionally heterologous TPSs, and wherein the first 3' TPS is homologous to the second 5' TPS. In another embodiment, one rAAV vector includes a first DNA segment comprising a first 5' AAV TPS linked to a nucleic acid segment of interest comprising a first promoter operably linked to a first open reading frame linked to a third DNA segment comprising a first 3' TPS, wherein the first 5' TPS and first 3' TPS in the first rAAV are heterologous TPSs. A second rAAV vector includes a first DNA segment comprising a second 5' TPS linked to a second nucleic acid segment of interest comprising a second promoter operably linked to a second open reading frame linked to a third DNA segment comprising a second 3' AAV TPS, wherein the second 5' TPS and second 3' TPS are optionally heterologous TPSs, and wherein the first 3' TPS is homologous to the second 5' TPS. In yet another embodiment, one rAAV vector includes a first DNA segment comprising a first 5' TPS linked to a second DNA segment comprising a first promoter operably linked to a first open reading frame linked to a third DNA segment comprising a first 3' AAV TPS, wherein the first 5' TPS and first 3' TPS are heterologous TPSs. A second rAAV vector includes a first DNA segment comprising a second 5' AAV TPS linked to a second DNA segment comprising a second promoter operably linked to a second open reading frame linked to a third DNA segment comprising a second 3' TPS, wherein the second 5' TPS and second 3' TPS are optionally heterologous TPSs, and wherein the first 3' TPS is homologous to the second 5' TPS. In this embodiment, expression of the two open reading frames may be enhanced in a cell contacted with the two rAAV vectors, as the formation of head-to-tail concatamers reduces transcriptional interference of the two open reading frames. In one embodiment, at least one of the open reading frames encodes a therapeutic gene product or a gene product which together with another gene product provides a therapeutic benefit to a mammal. The vectors may be contacted with a cell simultaneously or sequentially.

In yet another embodiment, one of the open reading frames encodes a catalytic RNA, for instance, one which degrades mRNA for one allele of a gene, e.g., an allele that encodes a defective or deleterious gene product, while the other open reading frame may encode a wild type (functional) gene product. Accordingly, one rAAV vector is employed to knock out gene expression of a mutant gene and, optionally, a second rAAV vector is employed to express the normal functional gene product. Thus, in one embodiment, one rAAV vector comprises a first DNA segment comprising a first 5' TPS linked to a second DNA segment comprising a DNA fragment encoding a catalytic RNA for the RNA corresponding to a mutant gene product, linked to a third DNA segment comprising a first 3' TPS, wherein optionally the first 5' TPS and first 3' TPS are heterologous TPSs. A second rAAV vector comprises a first DNA segment comprising a second 5' TPS linked to a second DNA segment comprising an open reading frame encoding the functional gene product linked to a third DNA segment comprising a second 3' TPS, wherein the second 5' TPS and second 3' TPS are optionally heterologous TPSs, and wherein the first 3' TPS is optionally homologous to the second 5' TPS. The vectors may be contacted with a cell simultaneously or sequentially.

In one embodiment, one rAAV vector comprises a first DNA segment comprising a first 5' TPS linked to a second DNA segment comprising a DNA fragment encoding a catalytic RNA for the RNA corresponding to a mutant gene product, linked to a third DNA segment comprising a first 3' TPS, wherein optionally the first 5' TPS and first 3' TPS are heterologous TPSs. A second rAAV vector comprises a first DNA segment comprising a second 5' TPS linked to a second DNA segment comprising an open reading frame encoding the functional gene product linked to a third DNA segment comprising a second 3' TPS, wherein the second 5' TPS and second 3' TPS are optionally heterologous TPSs, and wherein the first 3' TPS is optionally homologous to the second 5' TPS. In this embodiment, the vectors may be contacted with a cell simultaneously or sequentially.

In another embodiment, one rAAV vector includes a first DNA segment comprising a first 5' TPS linked to a second DNA segment comprising a portion of an open reading frame, e.g., the 5' end of an open reading frame for a selected gene, optionally linked to a transcriptional regulatory element, which portion of the open reading frame is 5' and operably linked to a donor splice site linked to a third DNA segment comprising a first 3' TPS, wherein the first 5' TPS and first 3' TPSs are heterologous TPSs. In one embodiment, the transcriptional regulatory element in a vector is a heterologous promoter, i.e., a non-AAV promoter which is not the endogenous promoter for the gene corresponding to the open reading frame, while in another embodiment the transcriptional regulatory element includes an enhancer and promoter. The second rAAV vector includes a first DNA segment comprising a second 5' TPS linked to a second DNA segment comprising an acceptor splice site that is 5' and operably linked to the remainder of the open reading frame for the selected gene or an open reading frame for a different gene linked to a third DNA segment comprising a second 3' TPS, wherein the second 5' TPS and second 3' TPS are optionally heterologous TPSs, and wherein the first 3' TPS is homologous to the second 5' TPS. In one embodiment, one rAAV vector includes a first DNA segment comprising a first 5' AAV TPS linked to a second DNA segment comprising a portion of an open reading frame, optionally linked to a transcriptional regulatory element, which portion of the open reading frame is operably linked to a donor splice site linked to a third DNA segment comprising a first 3' TPS, wherein the first 5' TPS and first 3' TPS are heterologous TPSs. In one embodiment, the transcriptional regulatory element in a rAAV vector is a heterologous promoter, while in another embodiment the transcriptional regulatory element in a rAAV vector includes a heterologous enhancer and promoter. The second rAAV vector includes a first DNA segment comprising a second 5' TPS linked to a second DNA segment comprising an acceptor splice site that is 5' and operably linked to the remainder of the open reading frame for the selected gene or a heterologous open reading frame, linked to a third DNA segment comprising a second 3' AAV TPS. The second 5' TPS and second 3' TPS are optionally heterologous TPSs, and the first 3' TPS is homologous to the second 5' TPS. In yet another embodiment, one rAAV vector includes a first DNA segment comprising a first 5' TPS linked to a second DNA segment comprising a portion of an open reading frame, optionally linked to a transcriptional regulatory element, which portion of the open reading frame is operably linked to a donor splice site linked to a third DNA segment comprising a first 3' AAV TPS, wherein the first 5' TPS and first 3' TPS are heterologous TPSs. The second rAAV vector includes a first DNA segment comprising a second 5' AAV TPS linked to a second DNA segment comprising an acceptor splice site that is 5' and operably linked to the remainder of the open reading frame for the selected gene or a heterologous open reading frame, linked to a third DNA segment comprising a second 3' TPS. The second 5' TPS and second 3' TPS are heterologous TPSs, and the first 3' TPS is homologous to the second 5' TPS. Thus, after contacting a cell with the two rAAV vectors, directional intermolecular recombination yields head to tail concatamers formed from the two rAAV vectors, which is a transcription unit, and transcription thereof yields a RNA which, when spliced, provides a mRNA for a gene product, e.g., a wild-type gene product or a fusion protein if the two open reading frames are not normally linked in the genome of a wild type (nonrecombinant) cell.

In one embodiment of the invention, the second DNA segment of the first recombinant DNA molecule comprises a portion of an open reading frame, e.g., an exon of a multiexon gene, operably linked to a transcriptional regulatory element, e.g., a promoter and/or enhancer. For example, the promoter may be the endogenous promoter for the gene corresponding to the open reading frame. In another embodiment, the exons in at least two rAAV vectors are from different genes, i.e., together they encode a fusion polypeptide. In one embodiment, more than two intravector heterologous TPS rAAV vectors are employed to transfer a gene, e.g., one vector has a first exon of an open reading frame linked to a promoter, a second vector has one or more downstream exons flanked by appropriate splice sites, and a third vector has the 3' end of the open reading frame flanked by a splice donor gene.

In another embodiment, the first rAAV vector includes a first DNA segment comprising a first 5' TPS linked to a second DNA segment comprising a transcriptional regulatory element linked to a third DNA segment comprising a first 3' TPS, wherein the first 5' TPS and first 3' TPS are heterologous TPSs. A second rAAV vector includes a first DNA segment comprising a second 5' TPS linked to a second DNA segment comprising an open reading frame, optionally linked to the corresponding endogenous or a minimal promoter, linked to a third DNA segment comprising a second 3' TPS, wherein the second 5' TPS and second 3' TPS are optionally heterologous TPSs, and wherein the first 3' TPS is homologous to the second 5' TPS. In one embodiment, the transcriptional regulatory element in the first rAAV vector is a promoter, while in another embodiment the transcriptional regulatory element is an enhancer. In yet another embodiment, the first rAAV vector includes a first DNA segment comprising a first 5' AAV TPS linked to a second DNA segment comprising a transcriptional regulatory element linked to a third DNA segment comprising a first 3' TPS, wherein the first 5' TPS and first 3' TPS are heterologous TPSs. A second rAAV vector includes a first DNA segment comprising a second 5' TPS linked to a second DNA segment comprising an open reading frame, optionally linked to the endogenous or a minimal promoter, linked to a third DNA segment comprising a second 3' AAV TPS, wherein the second 5' TPS and second 3' TPS are optionally heterologous TPSs, and wherein the first 3' TPS is homologous to the second 5' TPS. In yet another embodiment, the first rAAV vector includes a first DNA segment comprising a first 5' TPS linked to a second DNA segment comprising a transcriptional regulatory element linked to a third DNA segment comprising a first 3' AAV TPS, wherein the first 5' TPS and first 3' TPS are heterologous TPSs. A second rAAV vector includes a first DNA segment comprising a second 5 ' AAV TPS linked to a second DNA segment comprising an open reading frame, optionally linked to the endogenous or a minimal promoter, linked to a third DNA segment comprising a second 3' TPS, wherein the second 5' TPS and second 3' TPS are optionally heterologous TPSs, and wherein the first 3' TPS is homologous to the second 5' TPS. In one embodiment, at least one of the vectors, and optionally both vectors do not include one or more splice sites, e.g., neither vector includes a splice donor or splice acceptor site. Hence, after the cell is contacted with the two rAAV vectors and head to tail concatamers are formed, in one embodiment, the enhancer in the first rAAV vector enhances transcription from a promoter in the second (downstream) rAAV vector. In another embodiment, the transcriptional regulatory element in the first rAAV is a promoter, e.g., a constitutive or inducible promoter. Thus, after a cell is contacted with the two rAAV vectors and head-to-tail concatamers are formed, the promoter in the first rAAV vector induces transcription of the open reading frame in the second (downstream) rAAV vector due to the directional orientation of the promoter relative to the open reading frame.

Also provided are host cells contacted with one or more rAAV vectors of the invention or compositions of the invention. Host cells with the scope of the invention include eukaryotic cells, e.g., avian, amphibian, reptilian or mammalian cells, e.g., ovine, bovine, swine, equine, canine, caprine, feline, or human cells, and include eukaryotic brain, retinal, liver, lung, heart, muscle or hematopoietic cells. The host cell is preferably contacted with both of the vectors concurrently, although it is envisioned that the host cell may be contacted with each vector at a different time relative to the contact with the other vector(s), i.e., sequentially. Thus, vectors and compositions of the invention are useful in a method of delivering and/or expressing a nucleic acid product in a host cell, and to prepare host cells having the vector(s). Accordingly, the invention also provides a method to transfer and express a gene product, e.g., a polypeptide, in a host cell using at least two rAAV vectors.

Further provided is a method in which the rAAV vectors of the invention are administered to the cells or tissues of an animal, e.g., via systemic or local administration. The present invention is useful to overcome the current size limitation for transgenes within rAAV vectors, allows for the incorporation of a larger transcriptional regulatory region, e.g., a stronger heterologous promoter or the endogenous promoter, and for increased formation of directed intermolecular recombination events between different rAAV vectors thereby enhancing functional transgene formation.

The implications of directional intermolecular recombination of rAAV genomes to form a single episome, which may be a circular or linear concatamer comprising at least two different rAAV genomes, is particularly relevant for gene therapy with rAAV. First, large regulatory elements and genes beyond the packaging capacity of rAAV can be brought together by co-infecting tissue or cells with two independent vectors. For example, enhancers and/or promoters may be introduced into one vector while DNA comprising an open reading frame for a therapeutic or prophylactic gene of interest, with or without a minimal promoter, is introduced into a second vector. Thus, after co-infection with the two vectors, the transgene cassette size is increased beyond that for a single AAV vector alone, and the DNA comprising the opening reading frame is linked to the enhancer and/or promoter. In another embodiment of the invention, vectors encoding two independent regions of a gene are brought together by intermolecular recombination to form a template for an intact splicing unit.

Accordingly, the use of such vectors may aid in the development of gene therapy systems. For example, therapeutic or prophylactic therapies in which the present vectors are useful include blood disorders (e.g., sickle cell anemia, thalassemias, hemophilias, and Fanconi anemias), neurological disorders, such as Alzheimer's disease and Parkinson's disease, and muscle disorders involving skeletal, cardiac or smooth muscle. In particular, therapeutic genes useful in the vectors of the invention include the α-globin gene, the β-globin gene, the γ-globin gene, the cystic fibrosis transmembrane conductance receptor gene (CFTR), the factor VIII gene, the factor IX gene, the erythropoietin (epo) gene, the Fanconi anemia complementation group, a dystrophin gene, an antisense gene, a low density lipoprotein (LDL) gene, a tyrosine hydroxylase gene (Parkinson's disease), a glucocerebrosidase gene (Gaucher's disease), an arylsulfatase A gene (metachromatic leukodystrophies) or genes encoding other polypeptides or proteins, or other gene products, e.g., catalytic RNAs such as a ribozyme or siRNA.

Further provided is a rAAV vector comprising a 5' TPS and a 3' TPS which flank a nucleic acid segment of interest, wherein at least one of the TPSs is a pseudo PS. In one embodiment, the pseudo PS has at least 50%, e.g., 70%, 80%, 85%, 90%, 95%, or more, up to 100%, nucleic acid sequence identity to SEQ ID NO:3, SEQ ID NO:8, SEQ ID NO:9, or the complement thereof, and optionally has less than 80% including less than 70%, 60%, 50%, 40%, 30%, 20%, 10%, or 5%, or no, nucleic acid sequence identity to SEQ ID NO: 1, SEQ ID NO:2, SEQ ID NO:4, SEQ ID NO:5, SEQ ID NO:6, and/or SEQ ID NO:7, and/or the complement thereof. The vector is capable of being replicated and packaged when present in an appropriate host cell.

BRIEF DESCRIPTION OF THE FIGURES

FIG. 17. Comparison of free energy, G-C %, and $T_m$ for exemplary PS.

DETAILED DESCRIPTION OF THE INVENTION

Definitions

Figure 1:
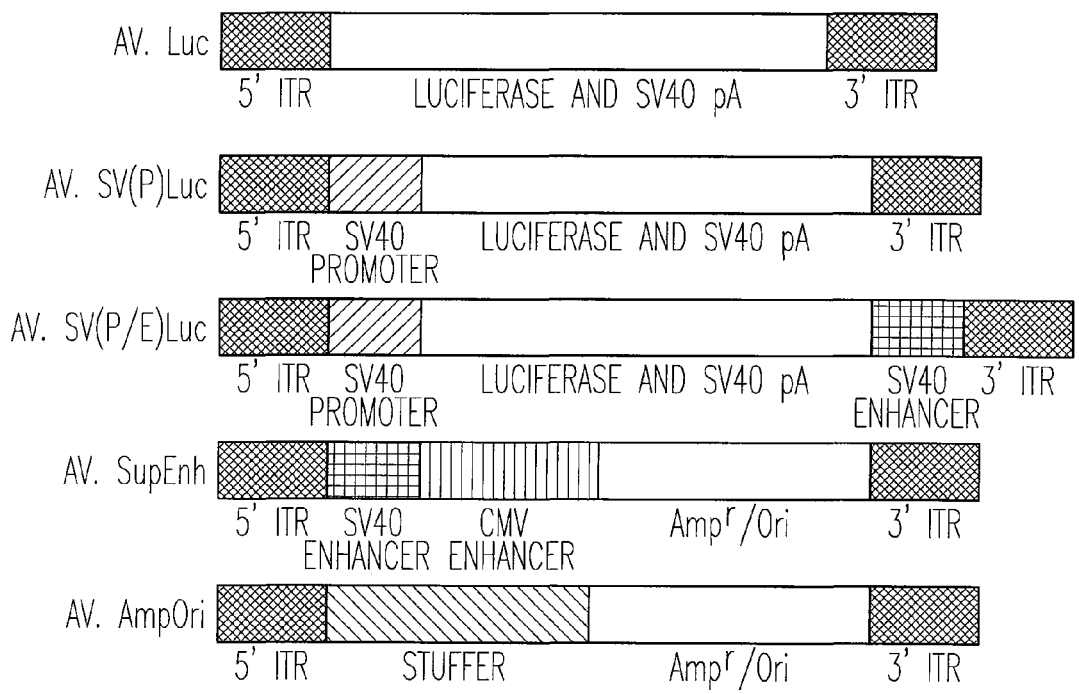
FIG. 1. Schematic representation of rAAV vectors employed for cis-activation.

As used herein, a "terminal palindromic sequence" or "TPS" is a palindromic sequence (PS) which is present at the 5' or 3' end of an AAV vector, that is capable of forming a secondary structure, optionally a stem or stem-loop structure found in native AAV TPSs, and, when present in a viral genome, does not substantially inhibit the packaging or replication of that genome, and/or provirus rescue, i.e., an intravector heterologous TPS rAAV vector is capable of being packaged and replicated in the presence of appropriate viral and/or cellular proteins.

"ITR" as used herein refers to an "inverted terminal repeat" sequence such as the sequence found at both ends of the viral genome of all known AAV serotypes. Within each ITR is a PS, e.g., in AAV-1, AAV-2, AAV-3, AAV-4, and AAV-6 the TPS is about 125 nucleotides (the AAV TPS does not include a D-sequence) and in AAV-5, the TPS is 137 nucleotides, that can fold to form a stable secondary structure, e.g., a hairpin-like stem or stem-loop structure. The ITR (a TPS and a D-sequence) of AAV contains all the necessary cis-elements for AAV replication provirus rescue and encapsidatiuon. For AAV type-1,2,3, 4 and 6, the ITR is 145 nucleotides in length, while for AAV-5, the ITR is 169 nucleotides in length.

A "vector" as used herein refers to a macromolecule or association of macromolecules that comprises or associates with a polynucleotide, and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "nucleic acid segment," "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight serotypes of primate AAVs, AAV-1 to AAV-8. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the TPS serotype. Pseudotyped rAAV are produced using standard techniques described in the art. As used herein, for example, rAAV5 may be used to refer an AAV having both capsid proteins and 5'-3' ITRs from the same serotype or it may refer to an AAV having capsid proteins from serotype 5 and 5'-3' ITRs from a different AAV. serotype, e.g., AAV serotype 2. For each example illustrated herein the description of the vector design and production describes the serotype of the capsid and 5'-3' TPS sequences. The abbreviation "rAAV" refers to recombinant adeno-associated virus, also referred to as a recombinant AAV vector (or "rAAV vector").

"Transduction," "transfection," "transformation" or "transducing" as used herein, are terms referring to a process for the introduction of an exogenous polynucleotide, e.g., a transgene in rAAV vector, into a host cell leading to expression of the polynucleotide, e.g., the transgene in the cell, and includes the use of recombinant virus to introduce the exogenous polynucleotide to the host cell, e.g., viral-mediated transfection is generally referred to as transduction. For example, for AAV the process includes 1) endocytosis of the AAV after it has bound to a cell surface receptor, 2) escape from endosomes or other intracellular compartments in the cytosol of a cell, 3) trafficking of the viral particle or viral genome to the nucleus, 4) uncoating of the virus particles, and generation of expressible double stranded AAV genome forms, including circular intermediates. The rAAV expressible double stranded form may persist as a nuclear episome or optionally may integrate into the host genome. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by hybridization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art.

A "rAAV vector" as used herein refers to an AAV vector comprising a polynucleotide sequence not of AAV origin (i.e., a polynucleotide heterologous to an AAVsequence), typically a sequence of interest for the genetic transformation of a cell referred to herein as a transgene or nucleic acid segment of interest which, when present in a vector, is DNA.

In preferred vector constructs of this invention, the heterologous polynucleotide is flanked by at least one, preferably two TPSs, one of which is linked to a D-sequence. A TPS in a vector of the invention may be a TPS homologous to various AAV TPS serotypes, a TPS from other parvoviruses or other viruses containing palindromic sequences described in the present invention, or may be a synthetic TPS, e.g., one constructed according to the present invention such that the synthetic sequence is one not found in other AAVs serotypes or parvoviruses. The term rAAV vector encompasses both rAAV vector particles and rAAV vector plasmids.

A "set of rAAV vectors", "rAAV vector set", "vector set", or "set" as used herein refers to at least one rAAV vector, or two or more rAAV vectors, wherein at least one of the vectors is an intravector heterologous TPS vector and, if the set has at least two different vectors, the TPS of at least one of the vectors has directional intervector homology with a TPS of a second vector such that when the vectors are introduced to a host cell, host cell lysate, or host, an increase in the formation of head-to-tail (also interchangeably herein referred to as tail-to-head) concatamers results. Vectors of the set may be introduced as individual viral compositions and/or may be combined with another or all the vectors of the set into a single composition. The vectors of the set may introduced at the same time or at different time points. Vectors of a set may be administered at equivalent ratios (i.e., 1:1) or mixed in various ratios.

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

A "rAAV vaccine" as used herein refers to an AAV vector comprising a polynucleotide sequence not of AAV origin herein referred to also as a transgene or nucleic acid segment of interest (i.e., a polynucleotide heterologous to AAV), that encodes a peptide, polypeptide, or protein capable of eliciting an immune response in a host contacted with the vector. Expression of the polynucleotide may result in generation of a neutralizing antibody response and/or a cell mediated response, e.g., a cytotoxic T cell response. In preferred vector constructs of this invention, the heterologous polynucleotide is flanked by at least one, preferably two AAV TPSs.

A "helper virus" for AAV refers to a virus that allows AAV (e.g., wild-type AAV) to be replicated and packaged by a mammalian cell. A variety of such helper viruses for AAV are known in the art, including adenoviruses, herpes viruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

An "infectious" virus or viral particle is one that comprises a polynucleotide component which it is capable of delivering into a cell for which the viral species is trophic. The term does not necessarily imply any replication capacity of the virus.

A "replication-competent" virus (e.g., a replication-competent AAV, sometimes abbreviated as "RCA") refers to a phenotypically wild-type virus that is infectious, and is also capable of being replicated in an infected cell (i.e., in the presence of a helper virus or helper virus functions). In the case of AAV, replication competence generally requires the presence of functional AAV packaging genes. Preferred rAAV vectors as described herein are replication-incompetent in mammalian cells (especially in human cells) by virtue of the lack of one or more AAV packaging genes. Preferably, such rAAV vectors lack any AAV packaging gene sequences in order to minimize the possibility that RCA are generated by recombination between AAV packaging genes and an incoming rAAV vector. Preferred rAAV vector preparations as described herein are those which contain few if any RCA (preferably less than about 1 RCA per $10^2$ rAAV particles, more preferably less than about 1 RCA per $10^4$ rAAV particles, still more preferably less than about 1 RCA per $10^8$ rAAV particles, even more preferably less than about 1 RCA per $10^{12}$ rAAV particles, most preferably no RCA).

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence (TRS) or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

"Packaging" as used herein refers to a series of subcellular events that results in the assembly and encapsidation of a viral vector. Thus, when a suitable vector is introduced into a packaging cell line under appropriate conditions, it can be assembled into a viral particle. Functions associated with packaging of viral vectors are described in the art.

A "terminator" refers to a polynucleotide sequence that tends to diminish or prevent read-through transcription (i.e., it diminishes or prevent transcription originating from one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-nonspecific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "prophylactic gene," "target polynucleotide," "transgene," "gene of interest", "nucleic acid segment of interest" and the like generally refer to a polynucleotide or polynucleotides to be transferred using a vector. In one embodiment, such genes are located within a viral vector thus can be replicated and encapsidated into viral particles. Target polynucleotides can be used in this invention to generate vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules or siRNA molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; (vi) polynucleotides for cancer therapy, such as E1A tumor suppressor genes or p53 tumor suppressor genes for the treatment of various cancers; and (vii) polynucleotides that encode proteins useful as diagnostic or marker tools. To effect expression of an open reading frame in a recipient host cell, it is preferably operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, and the like. The rAAV may also contain a selectable marker. A "gene" refers to a polynucleotide containing at least one open reading frame that is capable of encoding a particular gene product after being transcribed and translated.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV TPS promoters, as well as heterologous (non-AAV) promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Preferably, the genetic element is introduced into a chromosome or mini-chromosome in the cell; but any alteration that changes the phenotype and/or genotype of the cell and its progeny is included in this term.

A cell is said to be "stably" altered, transduced or transformed with a genetic sequence if the sequence is available to perform its function during extended culture of the cell in vitro. In preferred examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof, that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

An "isolated" polynucleotide, e.g., plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred.

A preparation of AAV is said to be "substantially free" of helper virus if the ratio of infectious AAV particles to infectious helper virus particles is at least about $10^2:1$; preferably at least about $10^4:1$, more preferably at least about $10^6:1$; still more preferably at least about $10^8:1$. Preparations are also preferably free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; preferably at least about 10,000 and more preferably at least about 100,000 particles per cell, over the course of the culture period specified.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, 1988; the local homology algorithm of Smith et al., 1981; the homology alignment algorithm of Needleman and Wunsch, 1970; the search-for-similarity-method of Pearson and Lipman, 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., 1988; Higgins et al., 1989; Corpet et al., 1988; Huang et al., 1992; and Pearson et al., 1994. The ALIGN program is based on the algorithm of Myers and Miller, supra. The BLAST programs of Altschul et al., 1990, are based on the algorithm of Karlin and Altschul supra.

Software for performing BLAST analyses is publicly available through the National Center for Biotechnology Information (URL available at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. See URL available at www.ncbi.nlm.nih.gov. Alignment may also be performed manually by inspection.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The practice of the present invention will employ, unless otherwise indicated, conventional techniques of molecular biology, virology, microbiology, recombinant DNA, and immunology, which are within the skill of the art. Such techniques are explained fully in the literature. See, e.g., Sambrook et al., 1989; Gait, 1984; Freshney, 1987; the series *Methods in Enzymology*; Miller and Calos, 1987; Weir et al.; Ausubel et al., 1987; Coligan et al., 1991; Coligan et al., 1995; and Scopes, 1994.

I. rAAV Vectors

Recombinant AAV vectors are potentially powerful tools for human gene therapy, particularly for diseases such as cystic fibrosis and sickle cell anemia. A major advantage of rAAV vectors over other approaches to gene therapy is that they generally do not require ongoing replication of the target cell in order to become stably integrated into the host cell.

rAAV vectors and/or viruses are also potentially powerful for the development of therapeutic or prophylactic vaccines to prevent infection, progression, and/or severity of disease. A major advantage of rAAV vectors for vaccine development is that they are capable of persisting for essentially the lifetime of the cell as a nuclear episome and therefore provide long term expression of the peptide, polypeptide, or protein of immunologic interest. Transgenes of interest include viral gene e.g. the envelope (env) or gag genes of HIV; bacterial genes e.g., streptococcal cell wall proteins; fungi, e.g., cocidomycosis; parasites, e.g., Leischmaniosis, or cancer genes, e.g. p53.

rAAV vectors and/or viruses may also contain one or more detectable markers. A variety of such markers are known, including, by way of illustration, the bacterial beta-galactosidase (lacZ) gene; the human placental alkaline phosphatase (AP) gene and genes encoding various cellular surface markers which have been used as reporter molecules both in vitro and in vivo. The rAAV vectors and/or viruses may also contain one or more selectable markers.

Recombinant AAV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts).

II. Selection and Preparation of AAV Vector

Adeno-associated viruses of any serotype are suitable to prepare rAAV, since the various serotypes are functionally and structurally related, even at the genetic level (see, e.g., Blacklow, 1988; and Rose, 1974). All AAV serotypes apparently exhibit similar replication properties mediated by homologous rep genes; and all generally bear three related capsid proteins such as those expressed in AAV-2. The degree of relatedness is further suggested by heteroduplex analysis which reveals extensive cross-heterologousization between serotypes along the length of the genome; and the presence of analogous self-annealing segments at the termini that correspond to TPSs. The similar infectivity patterns also suggest that the replication functions in each serotype are under similar regulatory control. Among the various AAV serotypes, AAV-2 is most commonly employed.

An AAV vector of the invention typically comprises a polynucleotide that is heterologous to AAV, i.e., a nucleic acid segment of interest. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and are preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the transgene heterologous polynucleotide generally comprises at least one coding region operatively linked to a suitable promoter, and may also comprise, for example, an operatively linked enhancer, ribosome binding site and poly-A signal. The transgene heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or preferably in place of the AAV genomic coding region (i.e., in place of the AAV rep and cap genes), but is generally flanked on either side by AAV TPS regions. This means that an TPS appears both upstream and downstream from the coding sequence, either in direct juxtaposition, preferably (although not necessarily) without any intervening sequence of AAV origin in order to reduce the likelihood of recombination that might regenerate a replication-competent AAV genome. However, a single TPS in conjunction with a D sequence may be sufficient to carry out the functions normally associated with configurations comprising two TPSs (see, for example, WO 94/13788), and vector constructs with only one TPS can thus be employed in the vectors and methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters are preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. An especially preferred sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), preferably linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Given the relative encapsidation size limits of various AAV genomes, insertion of a large heterologous polynucleotide into the genome necessitates removal of a portion of the AAV sequence. Removal of one or more AAV genes is in any case desirable, to reduce the likelihood of generating replication-competent AAV ("RCA"). Accordingly, encoding or promoter sequences for rep, cap, or both, are preferably removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are preferably not flanked by AAV TPSs and preferably do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by heterologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

III. Generating rAAV

To generate recombinant AAV particles useful for such purposes as gene therapy, the packaging cell line is preferably supplied with a recombinant AAV vector comprising AAV TPS regions surrounding one or more polynucleotides of interest (or "target" polynucleotides).

The target polynucleotide is generally operably linked to a promoter, either its own or a heterologous promoter. A large number of suitable promoters are known in the art, the choice of which depends on the desired level of expression of the target polynucleotide (i.e., whether one wants constitutive expression, inducible expression, cell-specific or tissue-specific expression, etc.).

Preferably, the rAAV vector also contains a positive selectable marker in order to allow for selection of cells that have been infected by the rAAV vector. Negative selectable markers can also be included; as a means of selecting against those same cells should that become necessary or desirable. In a preferred embodiment, one can make use of the "bifunctional selectable fusion genes" described by Lupton; see, e.g., PCT/US91/08442 and PCT/US94/05601. Briefly, those constructs involve direct translational fusions between a dominant positive selectable marker and a negative selectable marker. Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

Useful target polynucleotides can be employed in rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as the wild-type p53 tumor suppressor cDNA for replacement of the missing or damaged p53 gene associated with some lung and breast cancers, or the E1A tumor suppressor gene which is capable of inhibiting tumorigenesis and/or metastasis of a variety of different cancers including breast and ovarian cancers.

Since the therapeutic or prophylactic specificity of the resulting recombinant AAV particle is determined by the particular vector or pro-vector introduced, the same basic packaging cell line can be modified for any of these applications. For example, a vector comprising a specific target polynucleotide can be introduced into the packaging cell for production of the AAV vector by any of several possible methods; including, for example, electroporation or transfection of a plasmid comprising an rAAV pro-vector, or infection with an rAAV or helper virus comprising an rAAV vector or pro-vector.

Helper virus can be introduced before, during or after introduction of the rAAV vector. For example, the plasmid can be co-infected into the culture along with the helper virus; and the cells can then be cultured for a sufficient period, typically 2-5 days, in conditions suitable for replication and packaging as known in the art (see references above and examples below). Lysates are prepared, and the recombinant AAV vector particles are purified by techniques known in the art.

In a preferred embodiment, also illustrated in the Examples below, a recombinant AAV vector is itself stably integrated into a mammalian cell to be used for packaging. Such rAAV "producer cells" can then be grown and stored until ready for use. To induce production of rAAV particles from such producer cells, the user need only infect the cells with helper virus and culture the cells under conditions suitable for replication and packaging of AAV (as described below).

Alternatively, one or more of the AAV split-packaging genes or the rAAV vector can be introduced as part of a recombinant helper virus. For example, the E1, E3 and/or the E4 genes of adenovirus can be replaced with one or more split-packaging genes or an rAAV vector. Techniques for facilitating cloning into adenovirus vectors, e.g., into the E1 and/or E3 regions, are known in the art (see, e.g., Bett et al., 1994). Thus, a helper virus such as a recombinant adenovirus, can be used to provide helper virus functions as well as AAV packaging genes and/or an rAAV pro-vector, since (as is known in the art) a number of genes in such a helper virus (e.g., the E3 gene of adenovirus) can be replaced without eliminating helper virus activity. Additional genes can be inserted into such a helper virus by providing any necessary helper virus functions in trans. For example, human 293 cells contain adenoviral genes that can complement adenoviral E1 mutants. Thus, heterologous genes can also be cloned into an adenovirus in which the E1 genes have been deleted, for use in cells that can effectively provide such adenoviral functions in trans. Alternatively, the use of a helper virus can be eliminated by providing all necessary helper virus functions in the packaging cell.

IV. Introduction of Genetic Material into Cells

As is described in the art, and illustrated both herein and in the references cited above, genetic material can be introduced into cells (such as mammalian "producer" cells for the production of viral vectors) using any of a variety of means to transform or transduce such cells. By way of illustration, such techniques include, for example, transfection with bacterial plasmids, infection with viral vectors, electroporation, calcium phosphate precipitation, and introduction using any of a variety of lipid-based compositions (a process often referred to as "lipofection"). Methods and compositions for performing these techniques have been described in the art and are widely available.

Selection of suitably altered cells may be conducted by any technique in the art. For example, the polynucleotide sequences used to alter the cell may be introduced simultaneously with or operably linked to one or more detectable or selectable markers as is known in the art. By way of illustration, one can employ a drug-resistance gene as a selectable marker. Drug-resistant cells can then be picked and grown, and then tested for expression of the desired sequence, i.e., a packaging gene product, or a product of the heterologous polynucleotide, as appropriate. Testing for acquisition, localization and/or maintenance of an introduced polynucleotide can be performed using DNA hybridization-based techniques (such as Southern blotting and other procedures as is known in the art). Testing for expression can be readily performed by Northern analysis of RNA extracted from the genetically altered cells, or by indirect immunofluorescence for the corresponding gene product. Testing and confirmation of packaging capabilities and efficiencies can be obtained by introducing to the cell the remaining functional components of the virus and a helper virus, to test for production of viral particles. Where a cell is inheritably altered with a plurality of polynucleotide constructs, it is generally more convenient (though not essential) to introduce them to the cell separately, and validate each step seriatim. References describing such techniques include those cited herein.

V. Uses of Viral Vectors

Viral vectors can be used for administration to an individual for purposes of gene or vaccine therapy. Suitable diseases for gene or vaccine therapy include but are not limited to those induced by viral, bacterial, or parasitic infections, various malignancies and hyperproliferative conditions, autoimmune conditions, and congenital deficiencies.

Gene or vaccine therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic polynucleotide comprising a sequence capable, for example, of forming a stable complex with either the target gene or RNA transcript (antisense therapy), capable of acting as a ribozyme to cleave the relevant mRNA or capable of acting as a decoy for a product of the target gene.

The introduction of viral vectors by the methods of the present invention may involve use of any number of delivery techniques (both surgical and non-surgical) which are available and well known in the art. Such delivery techniques, for example, include vascular catheterization, cannulization, injection, inhalation, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue such as muscle or lung, any physical or biological method that will introduce the vector to a host animal can be employed. Vector means both a bare recombinant vector and vector DNA packaged into viral coat proteins, as is well known for virus administration. Simply dissolving a virus vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the viral vector as a free acid (DNA contains acidic phosphate groups) or a pharmacologically acceptable salt can be prepared in water suitably mixed with a surfactant such as hydroxypropylcellulose. A dispersion of viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the viral vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Compositions of this invention may be used in vivo as well as ex vivo. In vivo gene therapy comprises administering the vectors of this invention directly to a subject. For instance, the vectors of this invention may be administered to an animal such as a mammal alone or in combination with pharmaceutically acceptable carriers. The relative proportions of active ingredient and carrier are determined by the solubility and chemical nature of the compound, chosen route of administration and standard pharmaceutical practice. The dosage of the present vectors which will be most suitable for prophylaxis or treatment will vary with the form of administration, the particular vector chosen and the physiological characteristics of the particular patient under treatment. Generally, small dosages may be used initially and, if necessary, will be increased by small increments until the optimum effect under the circumstances is reached. The formulations and compositions described herein may also contain other ingredients such as antimicrobial agents, or preservatives, and may also be used in combination with other therapeutic agents.

Pharmaceutical compositions can be supplied as liquid solutions or suspensions, as emulsions, or as solid forms suitable for dissolution or suspension in liquid prior to use. For administration into the respiratory tract, a preferred mode of administration is by aerosol, using a composition that provides either a solid or liquid aerosol when used with an appropriate aerosolubilizer device. Another preferred mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, preferably at least about 80%, more preferably at least about 95%, and even more preferably at least about 99% of the cells of the desired tissue type. As a guide, the number of vector particles present in a single dose given by bronchoscopy will generally be at least about $1 \times 10^8$, and is more typically $5 \times 10^8$, $1 \times 10^{10}$, and on some occasions $1 \times 10^{11}$ particles, including both DNAse-resistant and DNAse-susceptible particles. In terms of DNAse-resistant particles, the dose will generally be between $1 \times 10^6$ and $1 \times 10^{14}$ particles, more generally between about $1 \times 10^8$ and $1 \times 10^{12}$ particles. The treatment can be repeated as often as every two or three weeks, as required, although treatment once in 180 days may be sufficient.

The effectiveness of the genetic alteration can be monitored by several criteria. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic regimen is ultimately the responsibility of the prescribing physician.

The foregoing description provides, inter alia, methods for generating high titer preparations of recombinant viral vectors that are substantially free of helper virus (e.g., adenovirus) and cellular proteins. It is understood that variations may be applied to these methods by those of skill in this art without departing from the spirit of this invention.

The invention will be further described by, but is not limited to, the following examples.

EXAMPLE 1

Enhancement of Recombinant AAV Mediated Gene Expression Through Intermolecular Cis-activation Materials and Methods
Recombinant AAV vectors The pcisAV.Luc proviral plasmid was generated by cloning the 1983 bp NheI/BamHI fragment from pGL3-Basic (Promega), containing the luciferase gene and SV40 late polyA signal, by blunt-end ligation into the blunted XbaI site of pSub201 (Samulski et al., 1987). Similarly, pcisAV.SV(P) Luc was generated using a blunted 2175 bp NheI/BamHI fragment from the pGL3-Promoter (Promega), containing the SV40 promoter, luciferase gene, and SV40 late polyA signal. The pcisAV.SV(P/E)Luc plasmid was generated by blunt-end ligation of a 2427 bp NheI/SalI fragment from pGL3-Control (Promega) into the blunted XbaI site of psub201. This construct contains the SV40 promoter, luciferase gene, SV40 late polyA signal and SV40 enhancer.

The "super-enhancer" vector, pcisAV.SupEnh, was produced using a two-step cloning process. First, a 0.62 kb blunted BglII/PvuI fragment containing the CMV immediate early enhancer from pIRES (Clontech) was subcloned into the blunted BamHI site in pGL3-Control (Promega) to make pGL3-Control-CMVenh. Then a 0.92 kb DNA segment containing both the CMV immediate early enhancer and the SV40 enhancer was released by ClaI/SalI double digestion of pGL3-Control-CMVenh and subsequently inserted into the blunted PstI site of pcisAV.GFP3ori (Duan et al., 1998b). The resulting pcisAV.SupEnh plasmid contains the SV40 enhancer, the CMV immediate early enhancer, the β-lactamase gene, and a bacterial replication origin. The ampicillin resistance gene (β-lactamase) and bacterial original of replication were included in pcisAV.SupEnh to facilitate the subsequent rescue of circular AAV genomes from infected cells in bacteria.

The control vector, pcisAV.AmpOri, was generated by blunt-end ligation of a 1.1 kb SalI digested stuffer sequence from the human glycosylasparaginase cDNA into PstI digested pcisAV.GFP3ori. This plasmid has a structure similar to that of pcisAV.SupEnh, except that it does not contain any enhancer elements. The pcisAV.AmpOri was used as a negative control for non-specific enhancement of transgene expression by intermolecular recombination of two different AAV vectors.

The integrity of the TPS sequences in all the plasmids was confirmed by digestion with restriction enzymes, including SmaI, MscI, and BssHII, which have unique cutting sites within different regions of TPS. All the viral preparations were obtained according to a method described in Duan et al. (1997). The quality of the viral stocks (i.e., contamination with adenovirus and/or wild type AAV) was confirmed as previously described in Duan et al. (1998b). The analyses showed less than 1 recombinant adenovirus and wt AAV infectious particles per $10^{10}$ particles of rAAV. Viral titers were determined by quantitative slot-blot hybridization using either luciferase, CMV enhancer, SV40 enhancer, or ori probes for each of the respective vectors against plasmid copy number standards.

Luciferase Enzyme Assays

Luciferase assays were performed from cell lysates harvested from either in vTPSo-infected human fibroblasts or from in vivo-infected mouse tibialis anterior muscle. Human fibroblasts were infected with virus in 60 mm dishes. These in vTPSo infected cells were harvested at 3 days post-infection by rinsing cells with PBS twice, and then incubating with 1× Report lysis buffer (Promega) (400 µl per 60 mm plate) at room temperature for 15 minutes. Cells were scraped into an eppendorf tube and centrifuged for 30 seconds at 14,000 rpm. Serial dilutions of supernatants were assayed for luciferase activity using reagents from Promega according to the manufacturer's protocols. Luciferase activity was detected in triplicate for each individual sample with a Luminometer (TD-20/20, Turner Designs Instrument, Sunnyvale, Calif.), at the setting of 90.3% sensitivity, 1 second delay, 10 second measurement. Six independent samples were assayed for each experimental condition.

For in vivo assay of luciferase activity, the anterior tibialis muscle of 8 week old C57BL/6 mice was infected with an indicated amount and type of AAV vectors in 30 µl phosphate-buffered saline (PBS). The entire muscle was harvested at 30 days or 90 days post-infection and weighed prior to cell lysate preparation. The muscle tissue was frozen in liquid nitrogen and pulverized by hand grinding with an ice-cold porcelain mortar and pestle. The muscle was further minced and homogenized in 100 μl of 1× Report lysis buffer with a hand-held plastic pestle for 2 minutes (Kontes, Vineland, N.J.). After 15 minutes incubation at room temperature, the crude lysates were spun for 30 seconds at 14,000 rpm, and the supernatants were used for luciferase activity assay as described above. To minimize variability, all experimental samples were analyzed simultaneously using the same batch of luciferase assay reagents and were normalized to the protein content in the lysate.

Results

Co-Administration of a Cis-Activating Vector Increases rAAV Mediated Luciferase Expression in Fibroblasts To test the hypothesis that cis-activation from two independent AAV vectors can occur following intermolecular concatamerization, several rAAV vectors with defined regulator elements and/or the luciferase reporter gene were constructed (FIG. 1). One of these vectors, AV.Luc, contains the luciferase transgene and an SV40 poly A signal but no promoter sequences. AV.SV(P)Luc is similar to AV.Luc except that an SV40 promoter (lacking the enhancer sequence) was inserted in front of the luciferase transgene. AV.SV(P/E)Luc includes both the SV40 promoter and enhancer, driving expression of the luciferase transgene, and was used as a control for maximal expression in the absence of intermolecular recombination with an enhancer containing vector. To evaluate intermolecular cis-activation by enhancer elements, an rAAV super-enhancer vector (AV.SupEnh) was also constructed, which contains SV40 and CMV enhancer regions without promoter or transgene sequences. A negative control vector (AV.AmpOri), which is similar to AV.SupEnh except that the enhancer sequences were replaced by a non-specific stuffer fragment, was also constructed.

Figure 2:
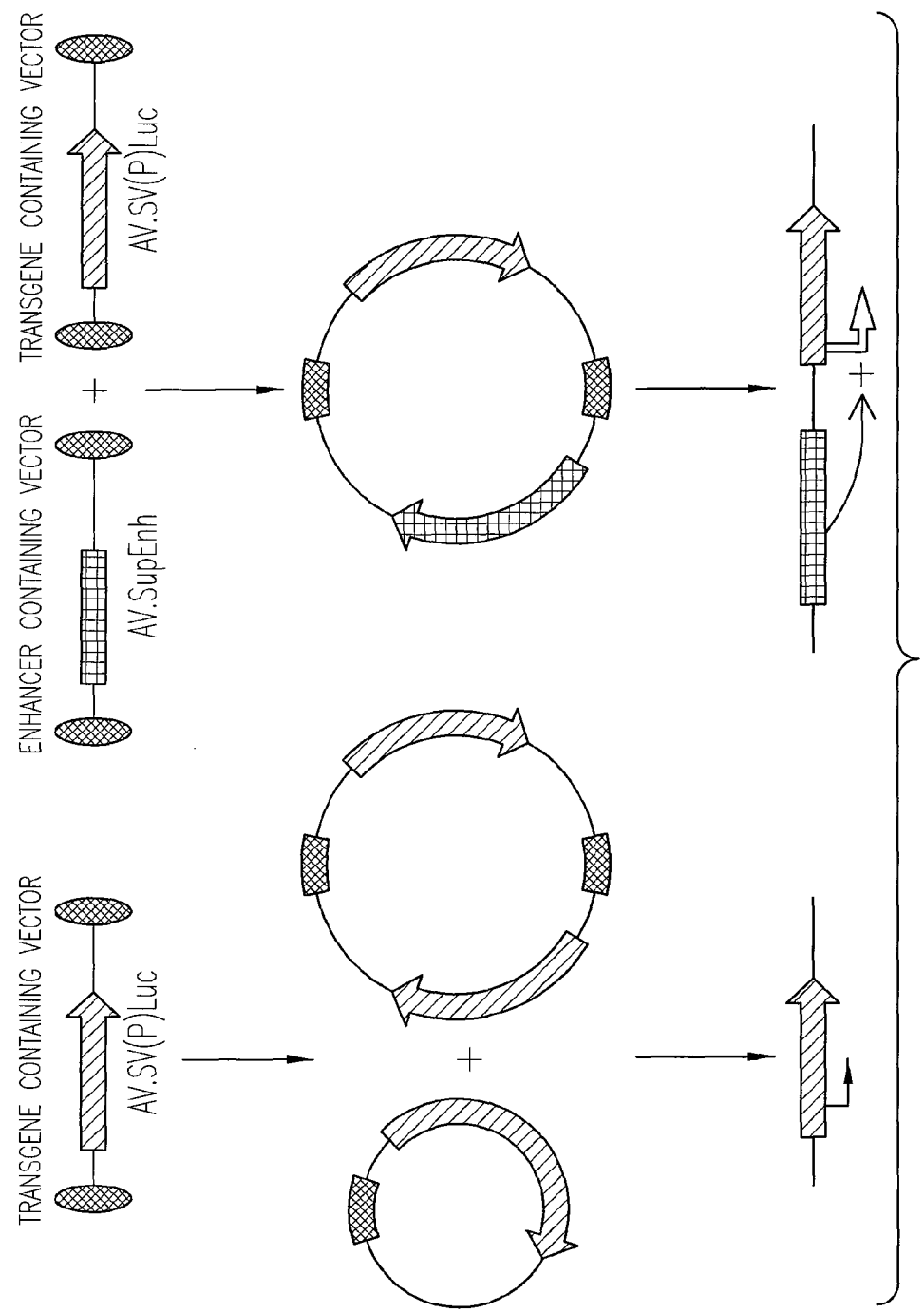
FIG. 2. Strategy for enhancing rAAV gene expression through intermolecular cis-activation. Two independent rAAV viruses, one encoding a transgene with or without a minimal promoter (e.g., AV.SV(P)Luc) and another harboring enhancer sequences (e.g., AV.SupEnh), were used to co-infect the same tissue. Subsequent concatamerization between two rAAV vectors substantially augments expression of the transgene, due to the presence of enhancer elements within the same circularized molecule.

Enhancers are cis-acting DNA sequences that can be recognized by regulatory proteins to stimulate transcription in a context independent manner relative to the promoter and transgene. If cells were co-infected with AV.SV(P)Luc and AV.SupEnh vectors, luciferase transgene expression could be significantly increased from the minimal SV40 promoter only if intermolecular recombination had occurred between the two independent vectors (FIG. 2). However, in accordance with the definition of an enhancer, no activation should occur if the enhancer sequences and the transgene cassette are located in separate circular DNA molecules (Lewin, 1997).

Initial experiments were performed by infecting $1 \times 10^6$ primary human fibroblasts with single vectors [AV.Luc or AV.SV(P)Luc] at a multiplicity of infection (moi) equal to 1000 viral particles/cell. Additional experimental points included co-infection of AV.Luc or AV.SV(P)Luc with either AV.SupEnh or AV.AmpOri at the same moi.

Figure 3:
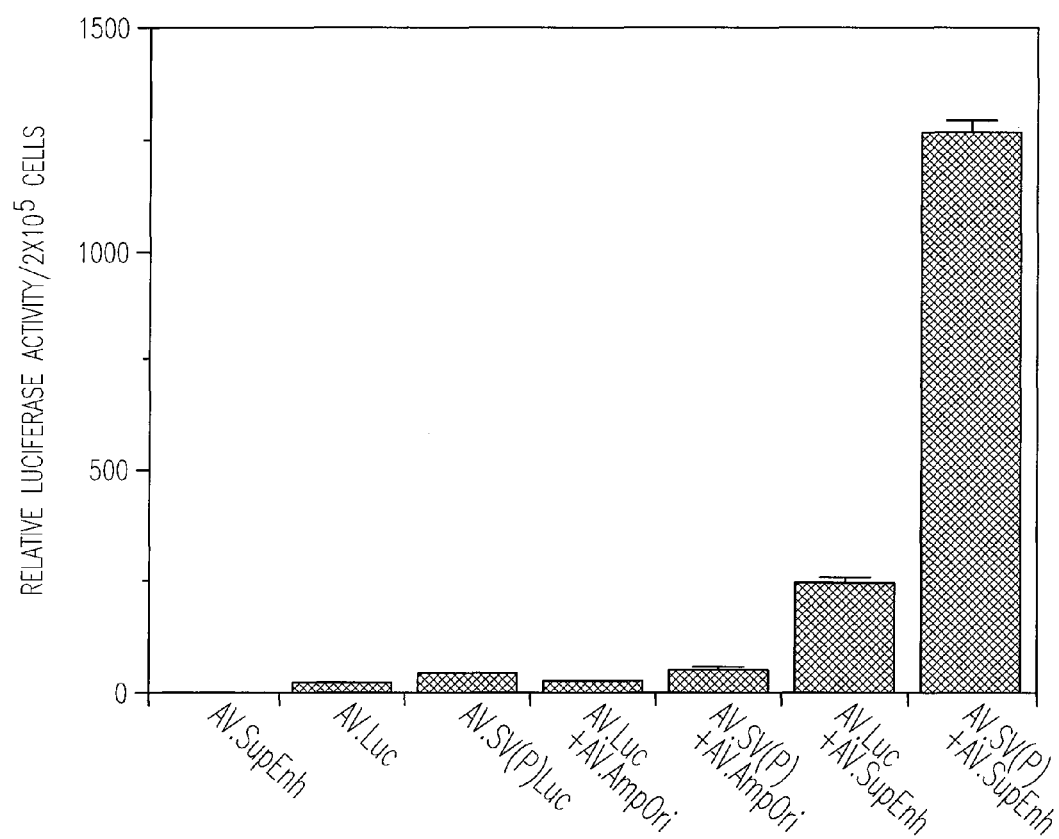
FIG. 3. Intermolecular cis-activation increases rAAV mediated gene transfer in fibroblasts. Human fibroblast cells were infected with the indicated rAAV vector(s) at an moi of 1000 for each individual vector. Luciferase activity was examined at 3 days post-infection. The data represent the mean +/−SEM of 6 independent samples for each experimental condition.

As shown in FIG. 3, infection of fibroblasts with both the promoter-less [AV.Luc] and the minimal promoter [AV.SV(P) Luc] luciferase constructs alone gave only minimal expression at 3 days post-infection. However, co-infection with AV.SupEnh produced 16- and 35-fold inductions in luciferase expression from the AV.Luc and AV.SV(P)Luc vectors, respectively. Thus, cis-activation of a minimal SV40 promoter can occur in the presence of a second AAV vector containing enhancer elements. Unanticipated, however, was the high level of transactivation of the AV.Luc construct, which contains no heterologous promoter sequences. These findings support earlier studies suggesting that TPSs contain a cryptic promoter (Flotte et al., 1993). The specificity of this induction was further demonstrated by the lack of transactivation following co-administration of an alternative control vector, AV.AmpOri, which does not contain enhancer elements.

To confirm that the transactivation observed was due to recombination of two independent AAV virus, Hirt DNA from infected cells was transformed into competent SURE *E. coli* cells. As expected, no bacterial clones were retrieved from cells infected with either AV.Luc or AV.SV(P)Luc alone (neither vector contains amp$^r$ and ori sequences). However, in cells co-infected with AV.SupEnh (which contains amp$^r$ and ori sequences but no luciferase gene), approximately 4% of the rescued clones also contained the luciferase transgene, according to restriction enzyme mapping and Southern blotting analyses. Subsequent transfection of HeLa cells with these rescued, circular concatamer plasmids demonstrated 103+/−6 fold higher luciferase activity from AV.Luc/AV.SupEnh, as compared to AV.Luc/AV.AmpOri recombined AAV genome plasmids. Taken together, these results indicated that intermolecular concatamerization of a reporter rAAV virus with an independent "super-enhancer" AAV vector substantially increased the efficiency of transgene expression in cultured human primary fibroblasts.

Figure 4A:
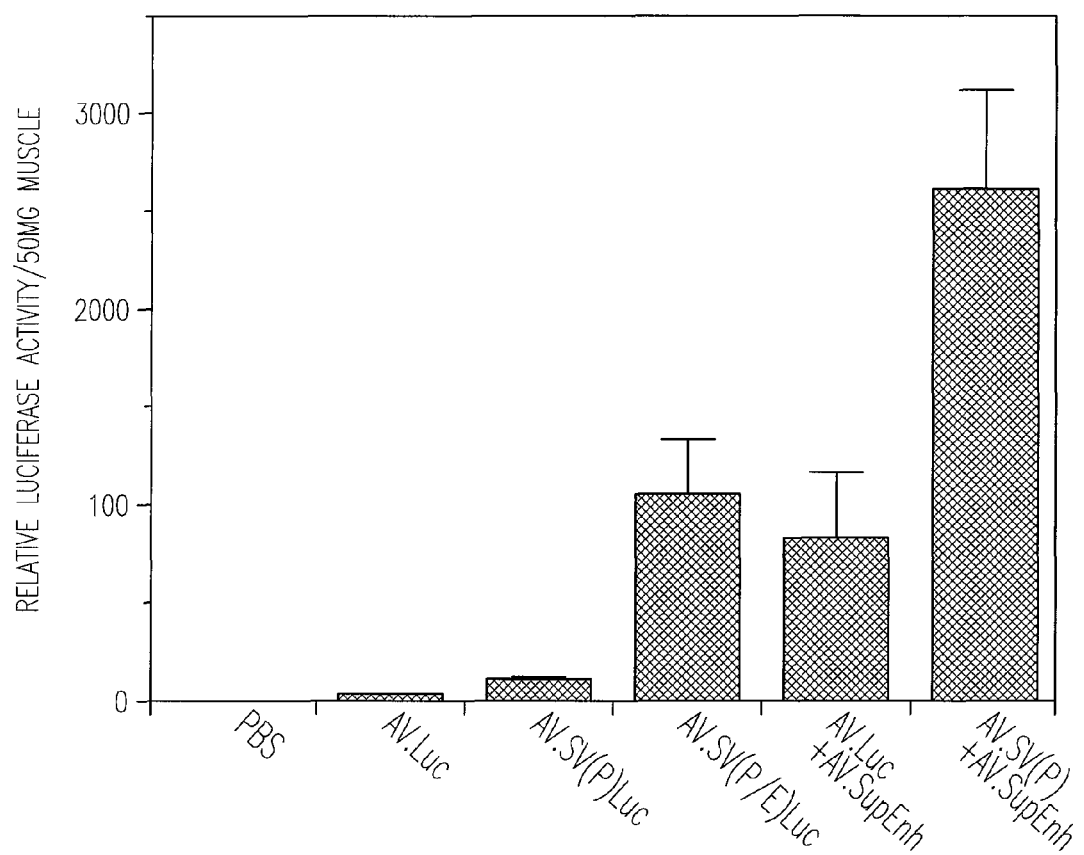
FIG. 4. Intermolecular cis-activation increases rAAV mediated gene transfer to muscle in vivo. Mouse tibialis anterior muscles were infected with the indicated rAAV vector(s) at $2 \times 10^{10}$ particles per viral vector in a total volume of 30 µl PBS. The luciferase activity in rAAV infected or mock infected (PBS) muscles was examined at 30 days (Panel A) and 90 days (Panel B) post-infection. The data represent the mean +/−SEM of 6 independent muscle samples for each experimental condition. Co-administration of the AV.SupEnh vector harboring enhancer elements substantially enhanced rAAV mediated luciferase expression in muscle from both the TPS and the minimal SV40 promoter.
Figure 4B:
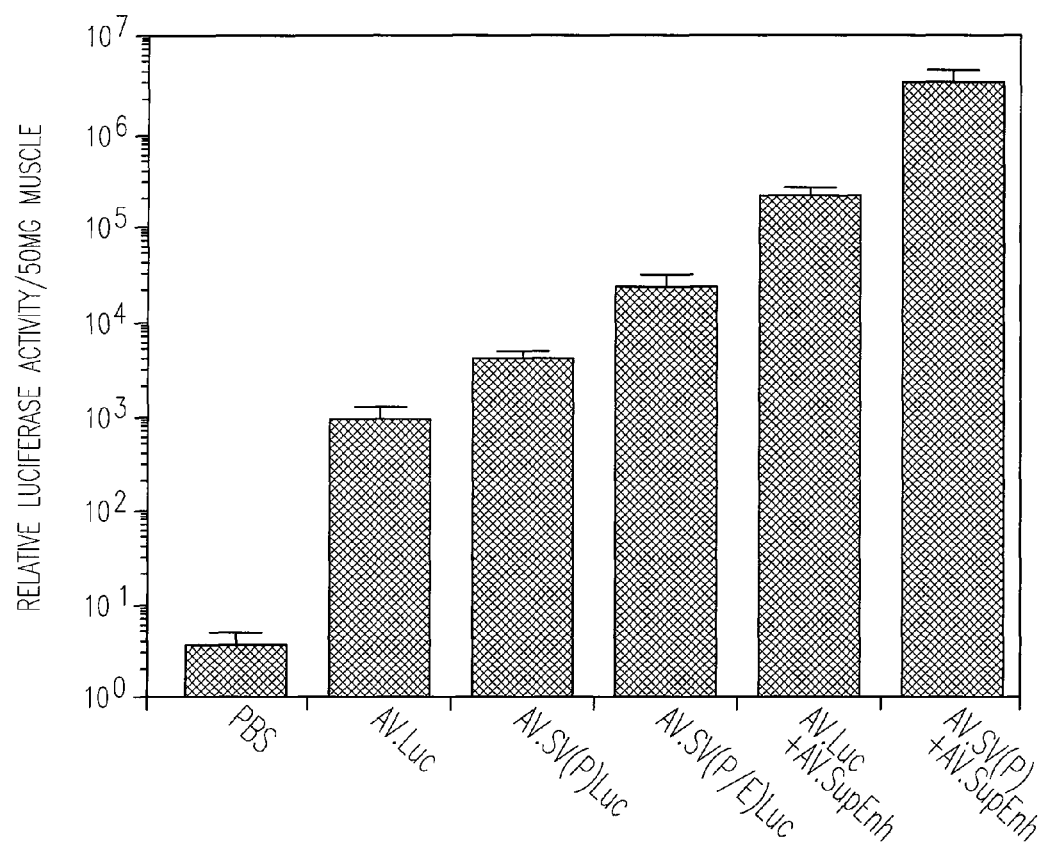

Intermolecular Cis-Activation Enhances AAV Mediated Luciferase Expression in Muscle Tissue In Vivo To confirm whether the in vitro findings could also be applied to increase rAAV mediated gene expression in vivo, $2 \times 10^{10}$ particles of AV.Luc or AV.SV(P)Luc were injected into the tibialis anterior muscle of C57BL/6 mice, either individually or in combination with AV.SupEnh ($2 \times 10^{10}$ particles). The infected muscles were harvested at 30 and 90 days post-infection. Intermolecular recombination of circular rAAV genomes increased from about 5% at the 30 day time point to 25% by 90 days post-infection. Importantly, co-administration of AV.SupEnh vector with either AV.Luc or AV.SV(P)Luc (FIG. 4A) led to a functional enhancement of transgene gene expression, with a 30-fold increase observed at 30 days post-infection. By 90 days post-infection, greater than 200-fold [AV.Luc] and 600-fold [AV.SV(P)Luc] increases in transgene expression were observed when AV.SupEnh was co-administered.

Consistent with in vitro experiments in fibroblasts, the bacterially rescued concatamers containing both the luciferase transgene and AV.SupEnh also demonstrated greater than a 100-fold higher luciferase activity than the original proviral luciferase plasmid (pcisAV.Luc) alone. Interestingly, 90 day muscles infected with $2 \times 10^{10}$ particles of the control AV.SV(P/E)Luc vector (which contains both the SV40 enhancer and promoter) produced luciferase levels that were 10- and 100-fold less than the levels seen following co-infection with AV.SupEnh/AV.Luc and AV.SupEnh/AV.SV (P)Luc, respectively. These findings underscore the potential of using large multi-enhancer segments to increase AAV mediated gene delivery through intermolecular cis-activation. Such applications will likely have broad implications for in vivo AAV mediated gene delivery to organs for which concatamerization of the AAV genome is an inherent process of its latent life cycle.

Both in vitro and in vivo results described herein demonstrated effective augmentation of transgene expression following intermolecular concatamerization between two independent AAV vectors carrying a transgene or enhancer sequences. A surprising finding was the strong induction of transgene expression from an AAV vector lacking an endogenous promoter (AV.Luc). Previous studies have implied weak promoter activity in the AAV TPS sequences (Flotte et al., 1993). Hence, it is possible that, in combination with enhancer sequences supplied by another AAV vector, a therapeutic level of transgene expression could be achieved for disease genes approaching the maximum packaging capacity for AAV. One notable example would be in applications of AAV for cystic fibrosis. Additionally, a particular interesting extension of this work will be to use large cell-specific enhancer regions for targeted expression.

EXAMPLE 2

Trans-Splicing Vectors with Intravector Heterologous TPSs

Engineering dual vector sets with a preferred recombinational bias to form tail-to-head heterodimers is one possible way to overcome the limitation of random recombination that reduces trans-splicing efficiency. Fundamental to such a strategy is a clear delineation of TPS involvement in the recombination process. To approach these questions, two of the most divergent (less than 50% conserved) TPS sequences, i.e., those derived from AAV-2 and AAV-5, were employed to generate a novel intravector heterologous TPS vector genome (AV2:5). This intravector heterologous TPS viral vector contained one AAV-2 TPS and one AAV-5 TPS at either end of the viral genome and functionally transduced a single encoded transgene at a similar efficiency to native rAAV-2 or rAAV-5 vectors, i.e., those with homologous TPSs on both ends. Intravector heterologous AV2:5 TPS viruses were employed to study the involvement of TPS sequences in genome circularization and concatamerization of viral DNA resulting from intra- and inter-molecular recombination. Intravector heterologous TPS vectors demonstrated a reduced efficiency to form monomer circular intermediates and an increased efficiency for directional tail-to-head intermolecular recombination of linear genomes capable of expressing a dual vector encoded trans-spliced gene product. These results suggest that TPS-mediated recombination events are important for AAV genome circularization and concatamerization. Altering TPS sequences to facilitate directional intermolecular recombination between independent vector genomes is therefore a useful approach to enhance dual vector gene delivery.

Materials and Methods

AAV-5 TPS Cloning

A 167 bp AAV-5 TPS linked to a D-sequence, with EcoRI and XhoI sites flanking the 5' A-sequence and a BamHI site at the 3' end of the D-sequence, was synthesized by IDT Inc. (Coralville, Iowa) according to the previously published AAV-5 sequence (Chiorini et al., 1999). The synthetic fragment was cloned in to the BamHI/EcoRI sites of pUC19 to give the plasmid intermediate pUC.AV5TPS. A second intermediate cloning vector was pTPS.5R/2L that contained both the AAV-2 and AAV-5 TPS separated by a portion of the luciferase cDNA. Using BamHI and XhoI double digestion, pTPS.5R:2L was generated from an AAV-2 proviral plasmid pCis.AV2.amp/ori by replacing one AAV-2 TPS with the AAV-5 TPS from pUC.AV5TPS. The AAV-5 TPS sequence in pUC.AV5TPS and pTPS.5R:2L was confirmed by a dideoxy thermocycling sequencing procedure conducted through the DNA facility at the University of Iowa. In order to eliminate the secondary structure of the TPS and allow for complete sequence reading, AAV-5 TPS containing plasmids were digested by EaeI, located at the junction of the A-sequence and the B-C loop prior to sequencing. The integrity of the AAV-5 TPS in subsequent cloning processes was confirmed by enzymatic digestion using the EaeI diagnostic assay and other restriction enzymes flanking the TPS (such as BamHI, XhoI and the like).

Figure 5:
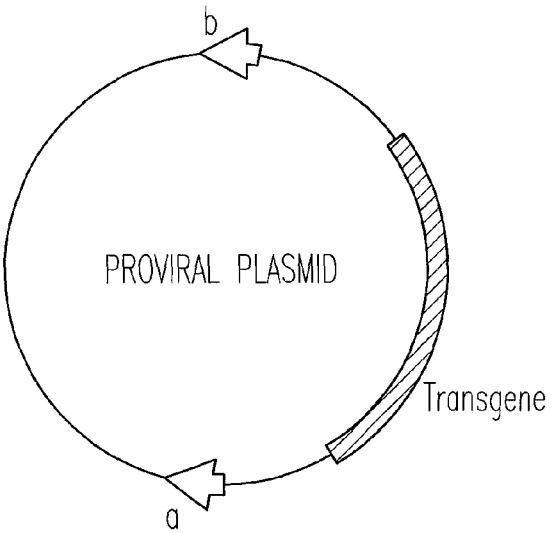
FIG. 5. Virus nomenclature. In total, nine viral vectors with various combinations of AAV-2 and/or AAV-5 TPSs and capsids were evaluated. pAVa:bTransgene denotes the proviral plasmids used to generate virus where "a" and "b" represent the two TPSs of either AAV-2 or AAV-5 origin. AVa:bTransgene refers to the viral DNA packaged into the viral capsid. AVa:b/cTransgene refers to the intact recombinant virus where "c" indicated the capsid serotype. In all cases the "a" and "b" TPSs are 5' and 3' to the reading frame of the encoded transgene, respectively.

Construction of rAAV-5 Proviral Plasmid and an Intravector Heterologous AV2:5 TPS Proviral Plasmid The nomenclature for various proviral plasmids and viruses is included in FIG. 5 and Table 1. A 1.4 kb AflIII/MXbaI (blunted) fragment containing an AAV-5 TPS and a portion of the stuffer sequence from pTPS.5R:2L was inserted into pUC.AV5TPS to form the AAV-5 proviral plasmid pAV5:5 amp/ori. An eGFP expression cassette from pAV2:2eGFP (previously described as pCisAV.GFP.3ori(5)) was then inserted into a PstI site to generate the pAV5:5eGFP. The intravector heterologous TPS proviral plasmid, pAV2:5eGFP, features an eGFP expression cassette flanked by an AAV-2 and AAV-5 TPS at both ends. It was generated by inserting the BglII/SalI (blunted) fragment from pAV2:2eGFP, which contains one AAV-2 TPS and the eGFP cassette, into the BglII/AflIII (blunted) sites of pAV5:5 amp/ori. BglII/AflIII digestion of pAV5:5 amp/ori removes one AAV-5 TPS. Both pAV5:5eGFP and pAV2:5eGFP harbor an ampicillin resistant gene and E. coli replicon in the proviral genome and, with the exception of TPS sequences such as pAV2:2eGFP, have identical genomic organization. pAV2:2eGFP was previously used to generate the rAAV-2 shuttle virus (AV2:2/2eGFP) capable of isolating circular viral genomes from Hirt DNA by bacteria transformation (Duan et al., 1998; Yang et al., 1999).

TABLE 1

Virus nomenclature of this study

| Proviral plasmid | 5'-TPS | 3'-TPS | Packaged with AAV-2 capsid | Packaged with AAV-5 capsid |
|---|---|---|---|---|
| pAV2:2eGFP[1] | AAV-2 | AAV-2 | AV2:2/2eGFP | AV2:2/5eGFP |
| pAV5:5eGFP | AAV-5 | AAV-5 | AV5:5/2eGFP | AV5:5/5eGFP |
| pAV2:5eGFP | AAV-2 | AAV-5 | AV2:5/2eGFP | AV2:5/5eGFP |
| pAV2:2LacZdonor[2] | AAV-2 | AAV-2 | AV2:2/2LacZdonor | NA |
| pAV2:2LacZacceptor[3] | AAV-2 | AAV-2 | AV2:2/2LacZacceptor | NA |
| pAV5:5LacZdonor | AAV-5 | AAV-5 | NA[4] | AV5:5/5LacZdonor |
| pAV5:5LacZacceptor | AAV-5 | AAV-5 | NA | AV5:5/5LacZacceptor |
| pAV5:2LacZdonor | AAV-5 | AAV-2 | AV5:2/2LacZdonor | NA |
| pAV2:5LacZacceptor | AAV-2 | AAV-5 | AV2:5/2LacZacceptor | NA |

[1] Previously described as pCisAV.GFP3ori (Duan et al., 1998)
[2] Previously described as pCisRSVLacZDonor (Duan et al., 2001)
[3] Previously described as pCisRSVLacZAcceptor (Duan et al., 2001)
[4] Not applicable to this study β-Galactosidase Trans-Splicing Vectors Three rAAV-2 β-galactosidase trans-splicing dual vector sets were generated with homologous AAV-2 TPSs, homologous AAV-5 TPSs, and intravector heterologous AV2:5 TPSs to evaluate TPS-mediated intermolecular recombination (Table 1). Type-2 TPS-based vectors were generated from two proviral plasmids: pAV2:2 LacZdonor and pAV2:2 LacZacceptor (previously described as the pCisLacZDonor and pCisLacZAcceptor, Duan et al., 2001). These two plasmids were used to generate AAV-2 TPS-based trans-splicing viruses, AV2:2 LacZdonor and AV2:2 LacZacceptor. In brief, these vectors each contain half of a RSV enhancer/promoter driven a β-galactosidase expression cassette. The promoter and 5' half of the lacZ gene followed by a splicing donor consensus sequence were cloned in the donor proviral plasmid (pAV2:2 LacZdonor). The backbone of the donor plasmid was from pSub201 (Samulski et al., 1987). The acceptor vector was obtained by replacing the eGFP cassette in pAV2:2eGFP with a splice acceptor sequence, the remainder of the 3' end of the lacZ gene, and a SV40 polyA signal. Through a series of subcloning steps and without altering the transgene cassettes, the AAV-2 TPS in pAV2:2 LacZdonor and pAV2:2 LacZacceptor was replaced by the AAV-5 TPS, thus generating the two AAV-5 based trans-splicing proviral plasmids, pAV5:5 LacZdonor and pAV5:5 LacZacceptor. These proviral plasmids were used to generate rAAV-5 trans-splicing viruses termed AV5:5 LacZdonor and AV5:5 LacZacceptor. The intravector heterologous AV2:5 TPS vector set was generated from the donor plasmid, pAV5:2 LacZdonor, and the acceptor plasmid from pAV2:5 LacZacceptor.

To construct pAV5:2 LacZdonor, both pAV2:2 LacZdonor and pAV5:5 LacZdonor were digested with XmnI and SphI. The 2.5 kb fragment from pAV5:5 LacZdonor containing the AAV-5 TPS and a portion of the RSV promoter was then cloned into the XmnI/SphI digested backbone of pAV2:2 LacZdonor to generate pAV5:2 LacZdonor. This proviral plasmid contained the AAV-5 and AAV-2 TPSs on the 5' and 3' ends of the transgene cassette, respectively (the 5' end is denoted as the TPS most proximal to the 5' end of the inserted reading frame). The pAV2:5 LacZacceptor proviral vector was cloned by a fragment exchange between pAV2:2 LacZacceptor and pAV5:5 LacZacceptor. The 2.3 kb NotI/Bgl II (blunted) fragment from pAV5:5 LacZacceptor containing the partial stuffer sequence and AAV-5 TPS linked to the splicing acceptor was replaced by the 2.6 kb NotI/XbaI (blunted) fragment derived from pAV2:2 LacZacceptor containing the AAV-2 TPS to generate pAV2:5 LacZacceptor.
Recombinant AAV Vector Production and Purification Since the present study sought to compare both Type-2 and Type-5 capsid viruses, the standard method of purification chosen was double-banded CsCl isopycnic centrifugation. A routine calcium phosphate co-transfection protocol was used to produce rAAV from 293 cells (Yan et al., 2002) with the exception that an adenovirus helper plasmid pAd4.1 from Targeted Genetics was used in the co-transfection cocktail. To produce rAAV-2 or rAAV-5 virus, the co-transfection protocol included the rAAV-2 proviral plasmid, pAV2RepCap and pAd4.1, or AAV-5 proviral plasmid, pAV5RepCap and pAd4.1 at a ratio of 1:3:3. Protocols similar to those previously described were used to pseudotype rAAV-2 genomes into AAV-5 capsids or rAAV-5 genomes into AAV-2 capsids (Yan et al., 2002), and were also used to package the intravector heterologous TPS vectors. The intravector heterologous TPS virus was packaged with AAV-2 capsid by transfecting the pAV2:5 TPS or pAV5:2 TPS proviral constructs into 293 cells together with pRep5, pAV2RepCap and pAd4.1 at a ratio of 1:1:3:3. Intravector heterologous TPS viruses using the AAV-5 capsid were generated by co-transfection of pAV2:5 TPS or pAV5:2 TPS proviral plasmids with pRep2, pAV5RepCap and pAd4.1 at a ratio of 1:1:3:3. Cells were harvested 70 hours after transfection and virus particles were released by freeze thawing, DNase I digestion, and deoxycholate treatment as previously described (Yan et al., 2002). All viral stocks were purified using the same CsCl ultracentrifugation procedure. Following 2 rounds of CsCl banding, about 1.36 to about 1.42 g/cm$^3$ fractions were collected. After dialysis against HEPES-buffered saline at 4° C. to remove the CsCl, the viral stocks were quantified by slot blot.
Virus Infection and Evaluation of Transgene Expression HeLa cells or ferret fetal primary fibroblasts were cultured as monolayers in Dulbecco's Modified Eagle Medium (DMEM) supplemented with 10% fetal bovine serum (Hy-Clone Laboratories, Inc), 100 U/ml penicillin, and 100 µg/ml streptomycin, and maintained in a 37° C. incubator at 5% $CO_2$-Cells were seeded at the density of $5\times10^5$ cell per 6-well plates or $2\times10^5$ cells per 12-well plates one day before infection. Immediately prior to infection, cells were washed once with 0% serum DMEM. The virus was then mixed with serum-free DMEM and directly applied to cells. At one hour post-infection, an equal amount of DMEM/20% FBS was added to each culture, bringing the final serum content to 10%. For evaluation of eGFP-expressing vectors, AV2:2/2eGFP, AV5:5/5eGFP, AV2:5/2eGFP, and AV2:5/5eGFP were used to infect HeLa cells cultured in 6-well plates at a multiplicity of infection (MOI) of 500 DRP (DNase Resistant Particle) per cell. At 24 hours post-infection, eGFP expression was analyzed by indirect fluorescence microscopy. Cells were collected for extraction of low-molecular weight DNA by a modified Hirt method as previously described in Yan et al. (2002).

Evaluation of LacZ trans-splicing expression of β-galactosidase was performed on HeLa cells or primary fetal fibroblasts seeded at $5\times10^5$ cells per 6-well plates or $2\times10^5$ cells per 12-well plates. 6-well cultures were used for X-gal histochemical staining and Hirt DNA extraction, while 12-well cultures were used for enzymatic histochemical assays. Viral infections were performed on 70% confluent HeLa cells or 90% confluent fibroblast cultures as described above using an MOI of $2.5\times10^3$ DRP per cell for each virus. Transgene expression assays were performed at 72 hours post-infection. The β-galactosidase expression from trans-splicing vector infection cells was evaluated by both in situ X-gal staining and/or an enzymatic assay using a Galacto-Light Plus system (Applied Biosystems, Bedford, Mass.) as previously described in Duan et al. (2001). For the enzymatic assay, the cell lysate supernatant was heated at 48° C. for 1 hour to inactivate the endogenous β-galactosidase activity.
Rescue of Circular Viral Genomes from AAV Transduced Cells Low molecular weight DNA was extracted from AAV-infected cells (Yan et al., 2002; Yan et al., 2000). The final DNA pellet from one well of the 6-well plate culture was dissolved in 50 µl $H_2O$, and one-tenth of the total volume (5 µl) was used to transform *E. coli* Sure Cells {(e14$^-$ (McrA$^-$) Δ(mcrCB-hsdSMR-mrr) 171 end A1 supE44 thi-1 gyrA96 rela/lac recB recJ sbcC umuC::Tn5 (Kan$^r$) uvrC [F'proAB lacI$^q$ZΔ (M15 Tn10 (Tet$^r$)])} by electroporation. The resultant total of ampicillin-resistant colonies was quantified and portion of the rescued plasmids were purified for molecular analysis by restriction enzymes, Southern blotting, and sequencing.
Results
rAAV-5 Forms Circular Intermediates and Heterodimers in HeLa Cells and Fetal Fibroblasts Despite the wide body of knowledge elucidating the transduction biology of rAAV-2 vectors, relatively little is known about similarities and differences in viral processing events between rAAV-2 and other vector serotypes. Among all the cloned AAV genomes, AAV-5 is the most distinct member of the AAV family in terms of viral genome sequence and tropism.

Detailed sequence comparisons between AAV-2 and AAV-5 genomes indicate a large diversity in the sequence of capsid and Rep proteins as well as TPS structure. Despite a lower than 50% homology in nucleotide sequence between AAV-2 and AAV-5 TPSs, both share a similar hairpin second structure. However, AAV-5 and AAV-2 Rep proteins cannot cleave the terminal resolution site at the AAV-2 and AAV-5

Figure 6A:
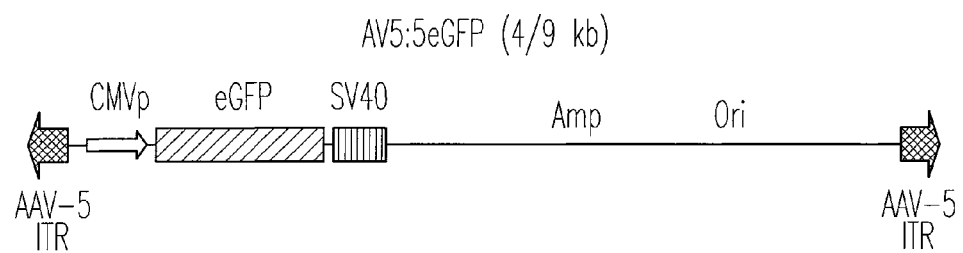
FIG. 6. Circularization and heterodimerization of AV5:5/5 vectors. To establish the ability of AV5:5/5 virus to form circular intermediates and heterodimers, circular intermediate formation was evaluated using an EGFP shuttle vector and dual vector heterodimerization using LacZ trans-splicing vector sets. Circular intermediate formation was quantified by rescue of replication competent plasmids in bacteria from Hirt DNA of AV5:5/5eGFP infected HeLa cells (500 particles/cell). To assess intermolecular recombination of rAAV-5 genomes, ferret fetal fibroblasts were infected with donor and/or accepter LacZ trans-splicing vector (2500 particles/cell). (A) Schematic diagram of the AV5:5eGFP viral genome. (B) The predominant form of rescued circular rAAV-5 intermediates is shown in the left panel, representative of a double-D circular monomer. The right panel is a Southern blot analysis of typical double-D TPS circular genomes isolated from AV5:5/5eGFP infected HeLa cells. BamHI digestion releases the double-D TPS junction as a 220 bp fragment that hybridizes to the AAV-5 TPS. PstI digestion gives rise to a larger 3.0 kb TPS hybridizing fragment and a smaller 2.0 kb EGFP hybridizing fragment. 76% (23 of 30) rescued plasmids analyzed had this defined structure with an intact double-D TPS. (C) Schematic representation of the rAAV-5-based LacZ trans-splicing vectors used to assess heterodimerization. Only heterodimerization of these two vectors in a tail-to-head (T-H) orientation is capable of reconstituting a functional LacZ gene product. 5'-LacZ, first half of LacZ genome; 3'-LacZ, second half of LacZ genome; SD, Splice donor; SA, Splice acceptor; RSV, promoter/enhancer; SV40, poly adenylation sequences; Amp, ampicillin resistance gene; Ori, Bacterial replication origin. (D) Ferret fetal fibroblasts were co-infected with AV5:5/5LacZdonor and/or AV5:5/5LacZacceptor viruses at an MOI=2500 particles/cell and functionally evaluated for β-galactosidase expression by histochemical X-gal staining at 7 days post-infection.

TPS, respectively, and hence cannot cross-complement during AAV replication. Since AAV TPSs contain all the necessary cis-functions required for virus replication, it is possible that the mechanisms of DNA strand conversion may be distinct for these AAV serotypes. Conversion productions of rAAV-2 viral genomes that involve the formation of episomal circular monomer or concatamer genomes have been described (Duan et al., 1998; Musatov et al., 2000; Schnepp et al., 2003; Song et al., 2001). However, it was unclear if rAAV-5 undergoes similar molecular processes of genome conversion during latent phase infection. To address this question, a rAAV-5 shuttle virus (AV5:5/5eGFP) was constructed to test whether the rAAV-5 genomes also form circular transduction intermediates. This AV5:5/5eGFP vector contained the eGFP reporter and an E. coli replicon/Ampicillin-resistant gene between the D sequence of two AAV-5 TPS strands (FIG. 6A). The ampicillin-resistant gene and E. coli replicon facilitated the rescue and amplification of circular transduction intermediates by transformation of Hirt DNA harvested from infected cells into bacteria.

Studies using this rescue assay in AV5:5/5eGFP-infected HeLa cells, demonstrated that 320+/−28 (n=4) colony forming units (CFU) could be rescued on agar plates containing ampicillin. Although the total number of rescued circular intermediates was approximately 11-fold lower than that obtained from AV2:2/2eGFP infection (3488+/−208 CFU), this is to be expected since rAAV-5 capsid-mediated transduction in HeLa cells is approximately 5-fold less efficient than transduction mediated by the rAAV-2 capsid (Yan et al., 2002).

Figure 6B:
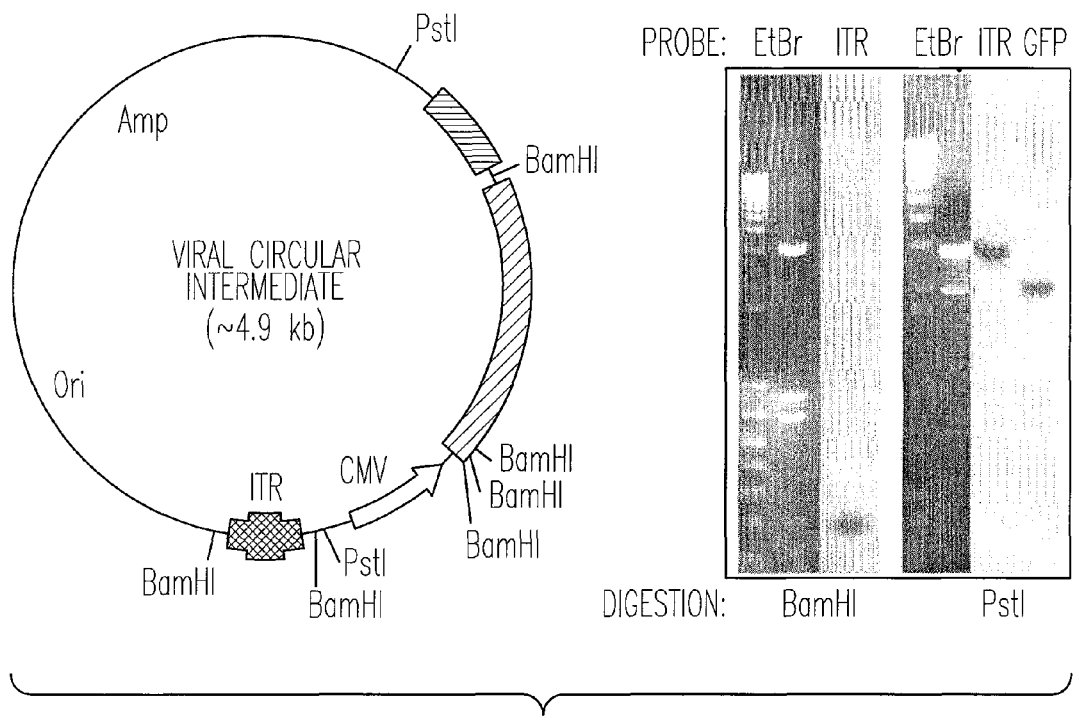

To evaluate the structure of rAAV-5 circular intermediates, 31 plasmids from AV5:5/5eGFP rescued colonies were evaluated by restriction enzyme analysis followed by Southern blotting with eGFP and AAV-5 TPS probes. FIG. 6B depicts the expected structure of an AAV-5 circular monomer genome and the restriction enzyme diagnostic analyses of a representative rescued AAV-5 circular intermediate. PstI digestion cleaved the monomer double-D circular intermediate into two fragments, a 2.0 kb small fragment with the eGFP and a 3.0 kb fragment which contains the TPS. 30 of the 31 rescued plasmids screened (94%) positively hybridized to both EGFP and AAV-5 TPS probes.

To characterize the T-H double-D ITR junction characteristic of circular AAV genomes, a diagnostic about 300 bp TPS hybridizing fragment is expected to be released by BamHI digestion. 23 of the 30 rescued intermediates (76%) released an TPS hybridizing junctional double-D BamHI fragment as previously described for AAV-2-based vectors (Duan et al., 1998; Yan et al., 2000; Yang et al., 1999). These results demonstrate that most of the rescued plasmids (94%) were circular monomer viral genomes derived from the head-to-tail self-circularization of AV5:5eGFP viral DNA with minor recombination events flanking the TPS that effected BamHI excision. This variability in the integrity of the TPS junction sequences of double-D circular intermediates has been previously described for AAV-2 (Duan et al., 1999, Yang et al., 1999).

Figure 6C:
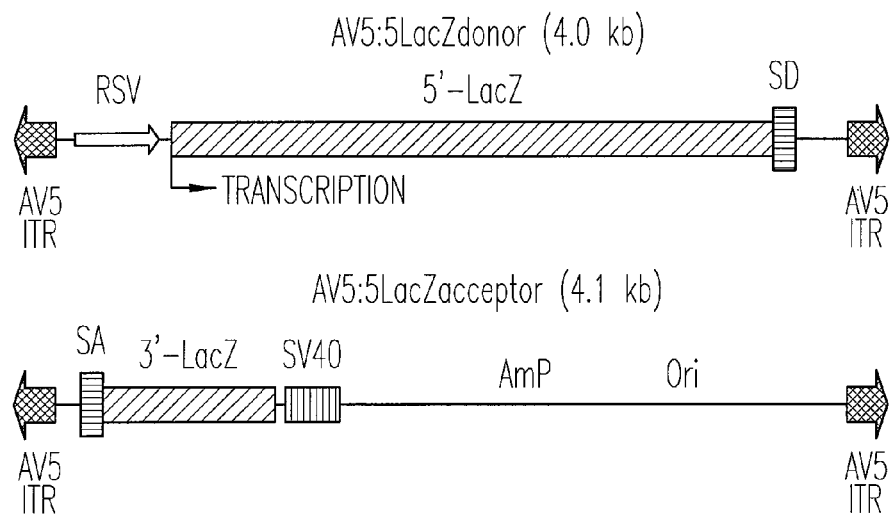
Figure 6D:
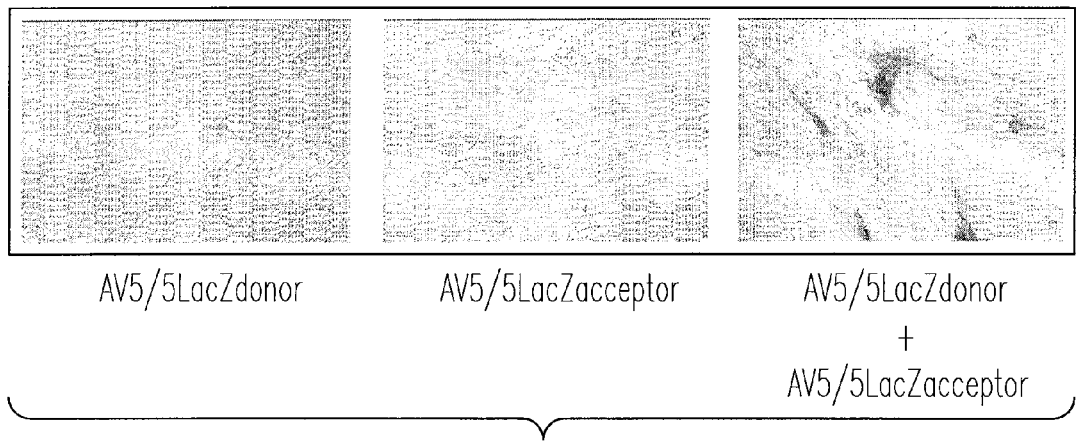

To evaluate the extent to which rAAV-5 genomes undergo intermolecular recombination, a dual vector heterodimerization approach that reconstitutes β-galactosidase expression by trans-splicing between two independent vector genomes, each harboring an exon of the LacZ mini-gene, was used. To this end, two LacZ trans-splicing vectors (AV5:5/5LacZdonor and AV5:5/5LacZacceptor, FIG. 6C) each harboring the AAV-5 TPS at both ends of the viral genome, were constructed. As previously observed for rAAV-2 trans-splicing vectors (Yan et al., 2000), reconstitution of β-galactosidase expression was seen only in fetal fibroblast co-infected with AV5:5/5LacZdonor and AV5:5/5LacZacceptor (FIG. 6D), but not with each vector alone. These findings demonstrated that rAAV-5 genomes are capable of forming heterodimers through intermolecular recombination. The level of reconstituted β-galactosidase expression was low in these studies because the level of AAV-5 capsid transduction in primary fibroblasts approximately 10-fold lower than that for AAV-2 capsid vectors.

Intravector Heterologous AV2:5 TPS Vector Genomes can Efficiently Package into Either AAV-2 or AAV-5 Capsids to Assemble Infectious Virions Molecular analyses of episomal rAAV intermediates revealed that a head-to-tail double-D TPS structure is the most common type of circular intermediate rescued following both rAAV-2:2 and rAAV-5:5 transduction. However, sequence analysis of double-D intermediates has demonstrated that approximately 15% of isolated circular intermediates contain more than one, but less than two, head-to-tail ITRs (Duan et al., 1999). Two potential explanations may account for heterogeneity in the ITR junctions of circular intermediates.

First, circularization may occur through nonspecific intramolecular end-end ligation followed by recombination events in bacteria that reduce the TPS to a more stable double-D structure. In support of this hypothesis, end-end joining of viral genomes had been proposed by others to be responsible for the formation of intramolecular linear concatamers (Nakai et al., 2003; Nakai et al., 2000). Second, intramolecular circularization of viral genomes might occur through TPS-mediated homologous recombination. If this process of homologous recombination is not exact, as might be expected since flip and flop hairpin loops exist in equal proportions in the viral genome, this could also explain the heterogeneity in ITR junctional sequence found in circular AAV genomes.

To distinguish between these two possibilities, intravector heterologous TPS vectors harboring an AAV-2 and AAV-5 TPS at either end of the viral genome were generated. Since AAV-2 and AAV-5 TPS share less than 50% homology in their sequence (FIG. 7A), it was hypothesized that if homologous recombination were the predominant mechanisms of rAAV genome circularization, such intravector heterologous TPS vectors would be impaired in this process. However, for such experiments to be informative, it was first necessary to confirm that intravector heterologous TPS AAV genomes could effectively produce infectious virus. To this end, methods for packaging pAV2:5eGFP genomes (FIG. 7B) into both AAV-2 and AAV-5 capsid were developed to generate progeny viruses AV2:5/2eGFP or AV2:5/5eGFP, respectively.

Figures 7C, 7D:
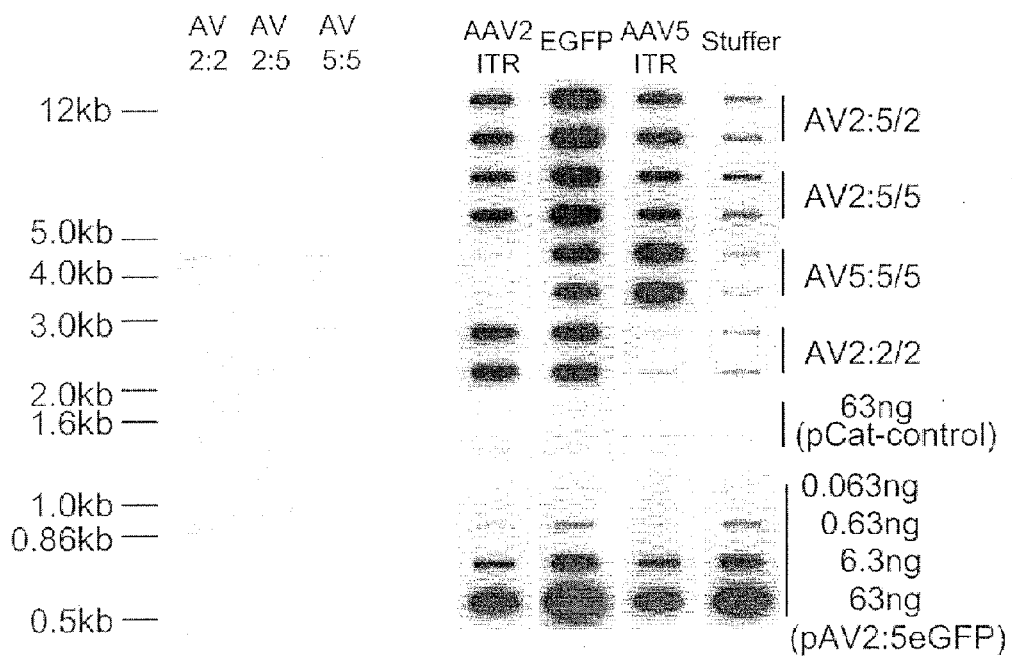
FIG. 7. Intravector heterologous TPS viral genomes produce infectious virus with similar efficiency to genomes with homologous TPS structures. (A) Homology alignment of AAV-2 and AAV-5 TPSs (SEQ ID NO: 1 and SEQ ID NO:2, respectively) generated by the Higgins' arithmetic using DNASIS software. The identical nucleotides in both sequences are indicated by shading. The terminal resolution site motif (trs) is underlined and the site of cleavage in each is indicated with vertical arrows. (B) Schematic structure of the intravector heterologous TPS proviral plasmid (pAV2: 5eGFP) and AV2:5eGFP viral genome. The intravector heterologous TPS AAV vector was packaged into either AAV-2 or AAV-5 capsid to assemble AV2:5/2eGFP or AV2:5/5eGFP infectious viruses, respectively. Similar vectors with homologous AAV-2 or AAV-5 TPSs on either end of the genome were used to generate AV2:2/2eGFP and AV5:5/5eGFP viruses, respectively (not diagrammed). (C) Alkaline Southern blot analysis of viral DNA from purified AV2:5/2eGFP virus was compared to viral DNAs from AV2:2/2eGFP and AV5:5eGFP viruses. A uniform band from each vector was visualized using a $P^{32}$-labeled EGFP probe in this Southern blot and confirms packaging of intact viral genomes. (D) Slot blot analysis evaluating DNA from purified viruses with different probes against the AAV-2 TPS, AAV-5 TPS, the EGFP transgene, or stuffer sequences in the backbone of proviral plasmids. pCat is a control plasmid with no sequence homology to any of the probes. pAV2:5eGFP was a control proviral plasmid used to compare hybridization signals for all probes used. Results demonstrate equivalent packaging of both AAV-2 and AAV-5 TPSs in the intravector heterologous TPS AAV vectors and nearly equivalent packaging of suffer sequences (about 10%) in all vectors. (E) The infectious titer of intravector heterologous TPS viruses (AV2:5/2eGFP and AV2:5/5eGFP) was compared to that achieved with native AV2:2/2eGFP and AV5:5/5eGFP virus following infection in HeLa cells. HeLa cells were infected with 500 particles/cell of AV2:2/2eGFP, AV5:5/5eGFP, AV2:5/2eGFP, or AV2:5/5eGFP, and EGFP fluorescent photomicrographs were taken at 48 hours post-infection. Intravector heterologous TPS viruses demonstrated similar levels of transduction as the native vectors for each serotype. Note the transduction with AAV-5 capsid virus is approximately 5-fold lower than that achieved with AAV-2 capsid vectors in HeLa cells.

Similar to pseudotyping of AAV-5 genomes with AAV-2 capsid, both Rep5 and Rep2 were required for package pAV2:5eGFP genome into either AAV-2 or AAV-5 capsids. The yield of the intravector heterologous TPS virus AV2:5/2eGFP and AV2:5/5eGFP was typically only 1 to 2 fold lower than that seen with AV2:2/2eGFP and AV5:5/5eGFP vectors containing homologous AAV-2 or AAV-5 TPSs. To confirm the packaging of the intact intravector heterologous TPS viral genome, $1\times10^9$ particles of AV2:2/2eGFP, AV2:5/2eGFP and AV5:5/5eGFP were digested with proteinase K and viral DNAs were subsequently resolved in a 1% NaOH alkaline agarose gel followed by Southern blotting against a $P^{32}$-eGFP probe. FIG. 7C demonstrated that viral genomes from AV2:2/2eGFP, AV2:5/2eGFP, or AV5:5/5eGFP virus all produced a uniform 4.6, 4.4 and 4.7 kb viral genome respectively.

These results confirmed that effective viral replication was initiated from the intravector heterologous TPS proviral plasmid and that intact intravector heterologous TPS genomes could be efficiently replicated and packaged into viral particles. The packaging of intact vector genomes was further confirmed by a series of slot blot hybridization experiments with viral DNA from purified AV2:5/2eGFP, AV2:5/5eGFP, AV2:2/2eGFP and AV5:5/5eGFP viruses (FIG. 7D). Probes used for this analysis included DNA sequences complementary to the flanking sequences outside the AAV-2 or AAV-5 TPS (i.e., in the proviral backbone stuffer sequence), and specific probes against the AAV-2 TPS, AAV-5 TPS and eGFP gene. Hybridization of viral DNA with stuffer sequence probes demonstrated approximately 10% of the viral genomes contained such sequences when compared to an eGFP probe. This was similar for both rAAV-2 or rAAV-5 packaged virions regardless of their TPS structure. This type of stuffer sequence packaging is also typical for rAAV vectors. Importantly, the ratio of TPS to EGFP hybridization demonstrated that both AAV-2 and AAV-5 TPSs were efficiently packaged into AV2:5/5 and AV2/5:2 virions. These results demonstrate that intravector heterologous TPS based vector genomes can efficiently package into viral capsids of AAV-2 or AAV-5 serotype with similar efficiency and fidelity to homologous TPS containing vectors.

Figure 7E:
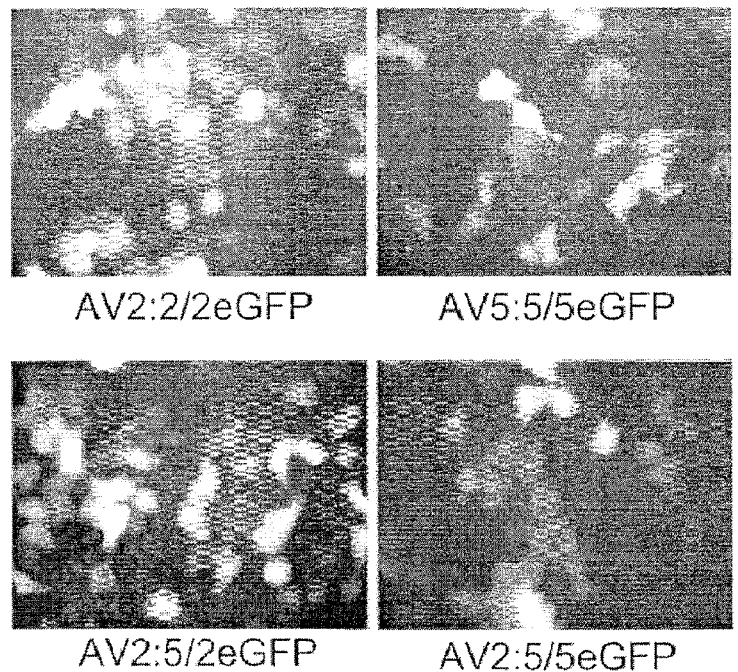

To establish that intravector heterologous viruses AV2:5/2eGFP and AV2:5/5eGFP had similar infectivity as homologous TPS containing vectors AV2:2/2eGFP and AV5:5/5eGFP, the ability of these four vectors to express their encoded eGFP transgene in HeLa cells was compared. Following infection of HeLa cells with an equivalent number of DNAse resistant particle (DRP) for each virus, the expression of EGFP was compared by fluorescence microscopy. Results from this comparison are shown in FIG. 7E and demonstrate indistinguishable levels of EGFP expression between the intravector heterologous TPS viruses (AV2:5/2eGFP and AV2:5/5eGFP) and their homologous TPS counterparts (AV2:2/2eGFP and AV5:5/5eGFP). These results demonstrated that intravector heterologous AV2:5 TPS genomes can be packaged with similar infectious efficiency to homologous TPS containing genomes. The lower EGFP expression in the group of AAV-5 encapsidated viruses, AV2:5/5eGFP and AV5:5/5eGFP, as compared to AAV-2 capsid was consist with the previously reported lower infectivity (about 5-fold) of rAAV-5 in HeLa cells (Yan et al., 2002). In summary, these studies evaluate transgene expression from intravector heterologous TPS vectors demonstrate that TPS homology on either end of the AAV genome is not necessary for functional expression of an encoded transgene.

Intravector Heterologous AV2:5 TPS Virus Less Efficiently Forms Circular Genomes than AV2:2 or AV5:5 TPS Viruses Using the above characterized intravector heterologous TPS vector, AV2:5/2eGFP, the hypothesis that TPS homology on either end of the AAV genome was needed for efficient formation of viral circular intermediates was tested. If indeed circular intermediates were reduced in AV2: 5/2eGFP infected HeLa cells, as compared to AV2:2/2eGFP and AV5:5/2eGFP, it would suggest that TPS homology potentially mediates intramolecular homologous recombination in the formation monomer circular viral genomes. Although similar eGFP expression was seen 2 day post-infection in the HeLa cells transduced with these three AAV-2 capsid packaged viruses (data not shown), the number of ampicillin resistant colonies rescued from the Hirt DNA extracted from the AV2:5/2eGFP infected cells was significantly reduced (8-fold) when compared to AV2:2/2eGFP and AV5:5/2eGFP viruses with homologous TPSs.

Molecular characterization of rescued plasmids by restriction enzyme analysis and Southern blotting against eGFP and TPS probes also demonstrated a considerable higher level of variability in the structure of the rescued clones derived from AV2:5/2eGFP as compared to AV2:2/2eGFP and AV5:5/2eGFP viruses. Molecular analysis of rescued clones using Southern blot hybridization against AAV-2 TPS, AAV-5 TPS, and eGFP probes and restriction digestion was used compare the integrity of double-D TPS junctions in circular intermediates obtained following infection with AV2:5/2eGFP, AV2:2/2eGFP, and AV5:5/2eGFP viruses (Table 2). Together with CFU counts, this molecular analysis demonstrated that the frequency for which AV2:5/2eGFP virus generated double-D circular intermediates was 60-fold less than that for viruses with homologous TPSs on either end of the genome. These results strongly suggest that TPS homology on either end of the viral genomes plays a key role in circularization of the AAV genome. The lower efficiency of intravector heterologous TPS vectors to form circular genomes is likely due to the less than 50% homology between AAV-2 and AAV-5 TPSs which restricts self-circularization of AV2:5eGFP genomes through the TPS mediated intramolecular recombination.

TABLE 2

Comparison of the circular intermediates rescued in bacteria

| virus | Amp resistant colonies[a] | Positive to EGFP probe (PstI)[b] | Positive to AAV-2 TPS probe (SphI)[b] | Positive to AAV-5 TPS probe (BamHI)[b] |
|---|---|---|---|---|
| AV2:2/2eGFP | 243 +/− 8.8 | 19/19 | 18/19 | ND |
| AV5:5/2eGFP | 239 +/− 6.2 | 19/19 | ND | 17/19 |
| AV2:5/2eGFP | 34 + 1.8 | 6/19 | 2/19[3] | 3/19[c] |

[a]1/10 of the Hirt DNA extracted from virus infected HeLa cells was used to transform *E. coli* Sure cell. The number represent the mean +/− S.E.M. (N = 3) Ampicillin resistant colonies from a 15 mm plate of cells.
[b]Nineteen Amp[R] colonies from each vector were randomly chosen for analysis of plasmid DNA. The plasmids were digested with PstI, SphI (cut AV2:2eGFP) or BamHI (cut AV2:5eGFP) and run on a 1% agarose gel followed by Southern blotting against eGFP, AAV-2 TPS, or AAV-5 TPS probes as indicated. ND: not determined.
[c]2/19 plasmid hybridized positive for both AAV-2 and AAV-5 TPS probes.

Circular head-to-head (H—H) and tail-to-tail (T-T) dimers and concatamers are not replication competent in bacteria due to opposing origins of replication and as such cannot be rescued in the bacterial system. However, head-to-head (H—H) and tail-to-tail (T-T) dimers can form through intermolecular recombination using a two-vector system (only one of which contains an Ori and Amp gene) (Yan et al., 2000; Yang et al., 1999). Hence, although it was concluded that intravector heterologous TPS vectors do not efficiently form a double-D circular monomer, the extent of intermolecular recombination which might occur in the formation of circular H—H and T-T dimers could not be determined.

Figure 8A:
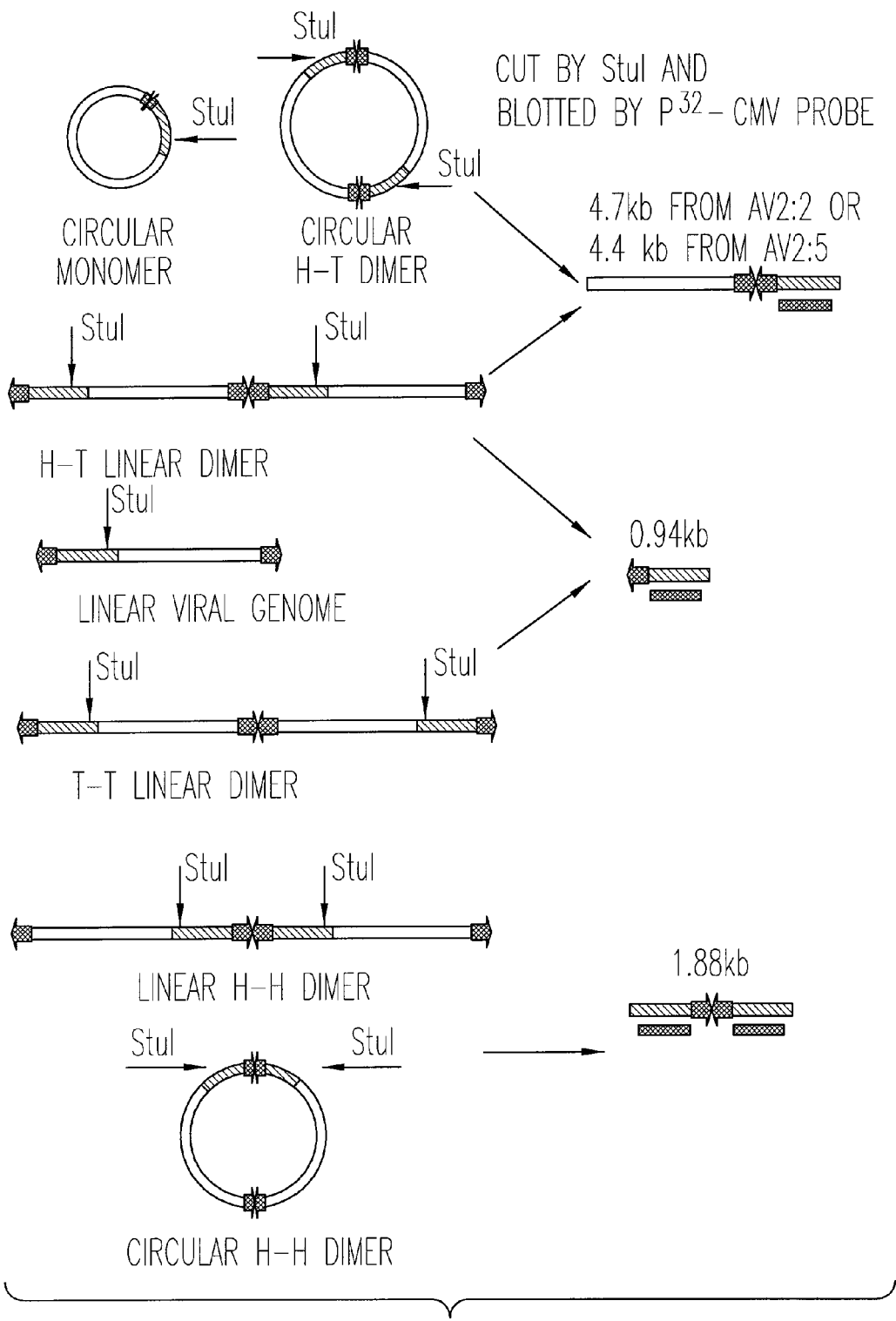
FIG. 8. Southern blot analysis of Hirt DNA extracted from AV2:5/2eGFP and AV2:2/2eGFP infected HeLa cells. HeLa cells were infected with AV2:2/2eGFP and AV2:5/2eGFP at the MOI of 500 particles/cell, and Hirt DNAs were extracted 2 days following infection. ¼ of the Hirt DNA from each sample was digested by StuI. Southern blotting of viral DNA was performed using a $P^{32}$-labeled probe against the CMV promoter. (A) Schematic representation of the predicted StuI digestion products from possible double stranded transduction intermediates. (B) CMV probed Southern blot results. The open arrows point to a 0.94 kb band diagnostic for the existence of linear viral genomes. Filled arrows point to bands diagnostic for monomer supercoiled circular intermediates in the uncut sample (2.8 kb) and linear full-length genomes in the StuI digested sample (4.7 kb). The migration of single stranded viral DNA (ssDNA) is also marked. U, undigested; C, StuI digested. (C) Time course comparison of Hirt DNA from AV2:2/2eGFP and AV2:5/2eGFP. Samples were obtained 6 hours, 1 day, 2 days, 3 days and 5 days after infection. More signal was observed for AV2:5/2eGFP, likely indicating that the intravector heterologous TPS AAV vector was more stable in HeLa cells. About the same signal was observed for both vectors at 6 hours, however, the AV2:2/2eGFP signal was significantly reduced at 2 days and almost absent at 5 days after infection. In addition, circular intermediates for AV2:2/2eGFP decreased during the time course.

To gain further insight into the molecular differences of genome conversion between intravector heterologous and homologous TPS vectors, the molecular forms of AAV genomes in Hirt DNA from AV2:2/2eGFP and AV2:5/2eGFP infected cells were analyzed. The goal of this assay was to directly distinguish the abundance of linear and circular monomer or dimer molecules by Southern blot. In this assay StuI was chosen as a diagnostic restriction site to distinguish the various molecular forms. StuI cuts once at the end of the CMV promoter and would only digest double stranded viral genomes. As shown in FIG. 8A, StuI digestion following by Southern blotting with a CMV probe would produce a 940 bp fragment from linear monomer, H-T, and T-T dimer viral genomes. H-T linear dimer genomes, as well as H-T circular genomes, would also produce a 4.7 or 4.4 kb linear fragment dependent on the vector type. In contrast, H-H linear and H-H/T-T circular dimers would produced a unique 1.88 kb fragment for both vector types.

Figure 8B:
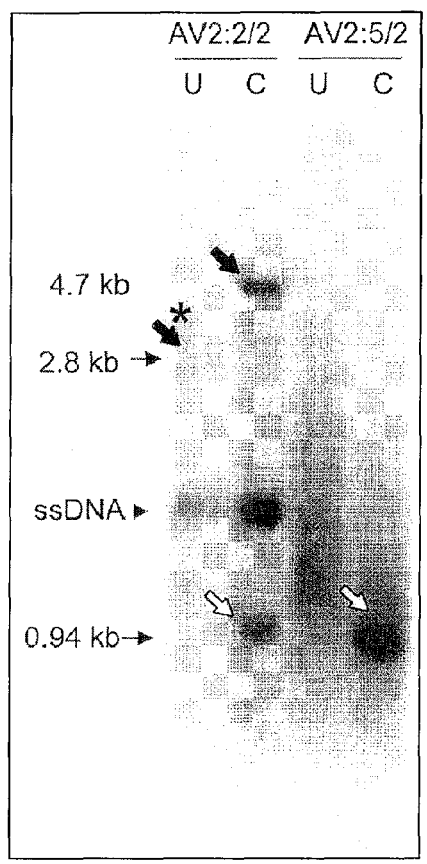
Figure 8C:
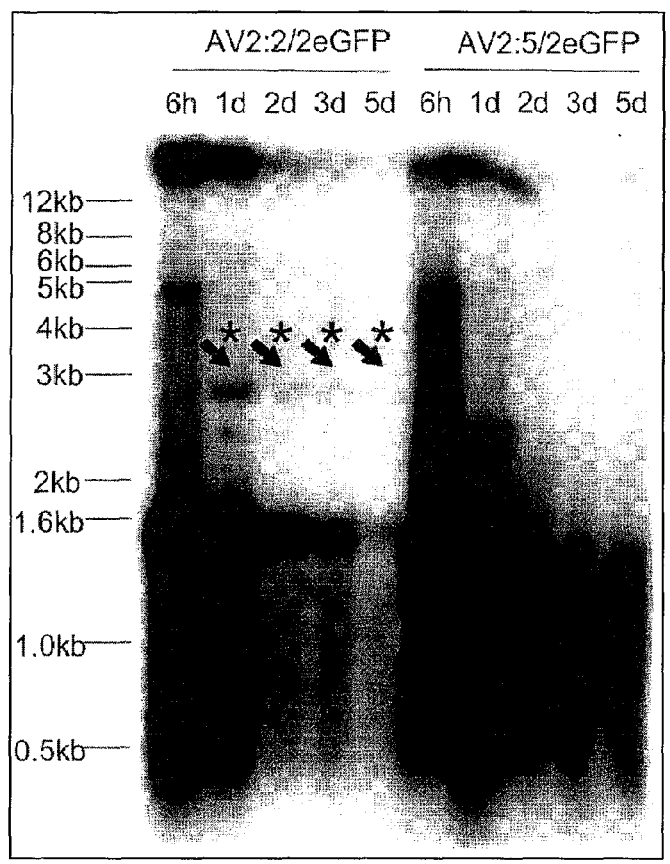
Figure 9A:
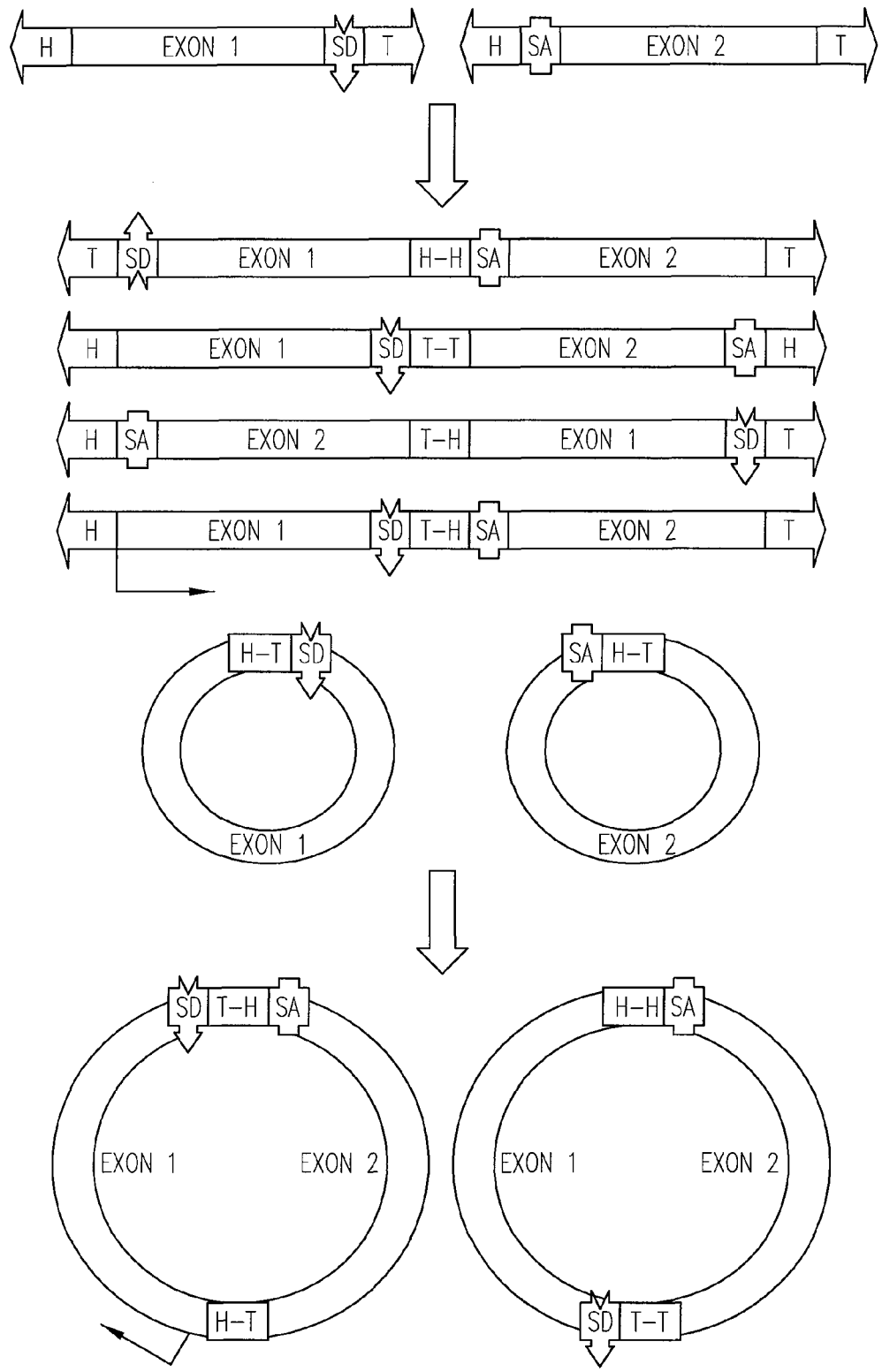
FIG. 9. Schematic of trans-splicing vectors and products of intermolecular recombination for (A) intravector homologous TPS AAV vectors and (B) intravector heterologous TPS AAV vectors.
Figure 9B:
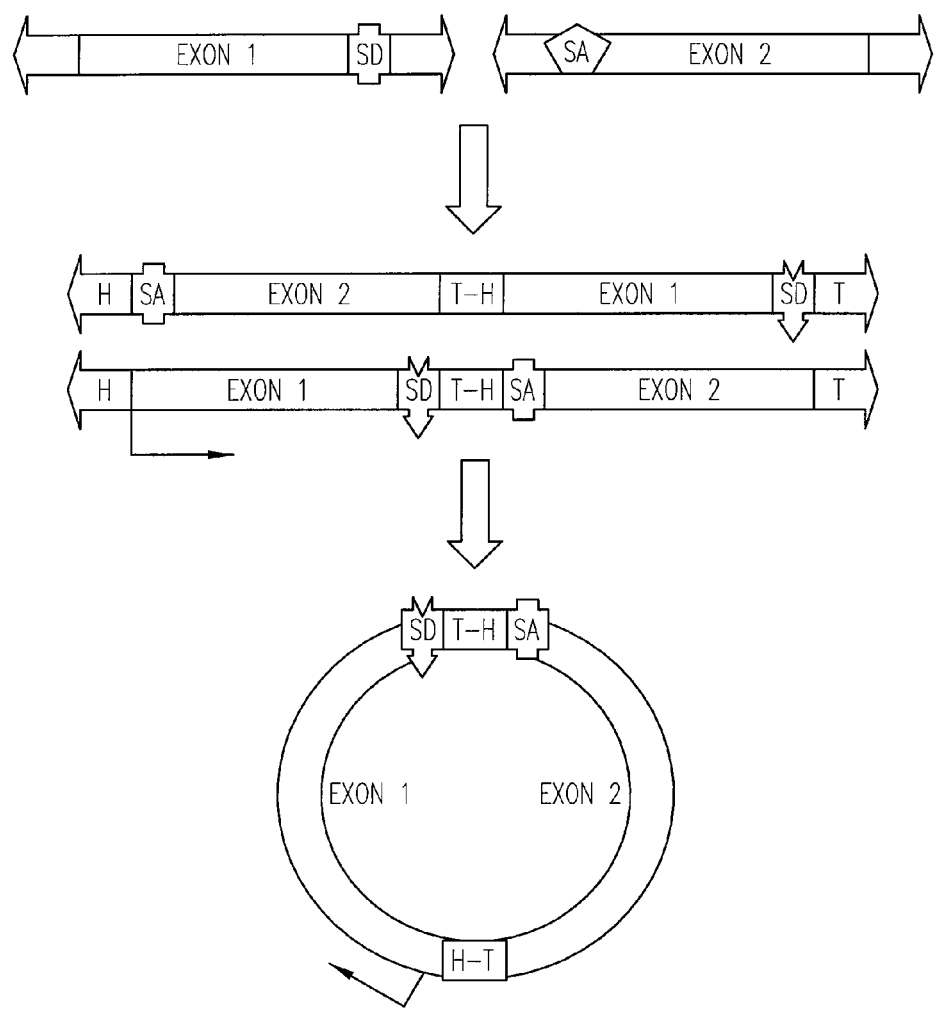

Results of Southern blot analysis (FIG. 8B) for AV2: 2eGFP demonstrated StuI digested CMV hybridizing bands of 940 bp and 4.7 kb, consistent with both linear and circular H-T intermediates. Furthermore, undigested DNA samples gave rise to a previously described supercoiled monomer circular intermediates (Duan et al., 1998; Sanlioglu et al., 2000) that migrate at 2.8 kb and shift in molecular weight to linear 4.7 kb fragments following digestion with a single cutter. In stark contrast to AV2:2eGFP, AV2:5eGFP Hirt DNA demonstrated a significantly increased abundance of the StuI 940 bp end fragment and a lack of circular viral genome in the undigested sample. These findings are most consistent with increased abundance of linear monomer genomes with intravector heterologous TPS vectors. Such differences between the abundance of linear and circular genomes for AV2:2eGFP and AV2:5eGFP vectors are also consistent with the Hirt DNA bacterial rescue experiment.

One additional difference observed between Hirt DNA from AV2:2eGFP and AV2:5eGFP infected cells was the apparent greater stability of intravector heterologous TPS viral genomes. Although only a 48 hour time point was evaluated, these findings suggest that linear intermediates formed by intravector heterologous TPS vector genomes may have increased stability over other intermediates formed by homologous TPS vectors. The mechanism behind this finding is unclear, but may reflect a more uniform genome conversion product for intravector heterologous TPS vectors. For example, although linear double stranded genomes certainly exist in homologous TPS vectors (as indicated by the 940 bp CMV hybridizing end fragment following StuI digestion), their precursor form is not clearly visible in the undigested DNA. Hence, one must assume that molecular linear forms are quite diverse in second structure. It is possible that such molecular intermediates are more susceptible to DNase digestion.

Intravector Heterologous AV2:5 TPS Genomes Facilitate Directional Intermolecular Recombination and Enhance the Efficiency of Dual Vector Trans-Splicing Approaches The results from Hirt DNA Southern bolt analysis and bacteria rescue experiment have suggested that the TPS homology on either end of the rAAV genome plays a key role in rAAV genome circularization. These findings provide direct evidence that intramolecular circularization of AAV genomes is an TPS sequence-dependent recombination process. The generation of intravector heterologous TPS vectors with reduced capacity to form monomer circular intermediates also afforded the opportunity to address the involvement of these structures as precursors to intermolecular heterodimers. The formation of intermolecular heterodimers permits dual vector technologies to increase the functional capacity of rAAV to delivery large transgenes that cannot be packaged into a single vector genome. To this end, intravector heterologous TPS vectors were used to investigate the underlying mechanisms responsible for generating heterodimers as a basis for potentially improving the efficiency of dual vector approaches for gene therapy.

Figure 10A:
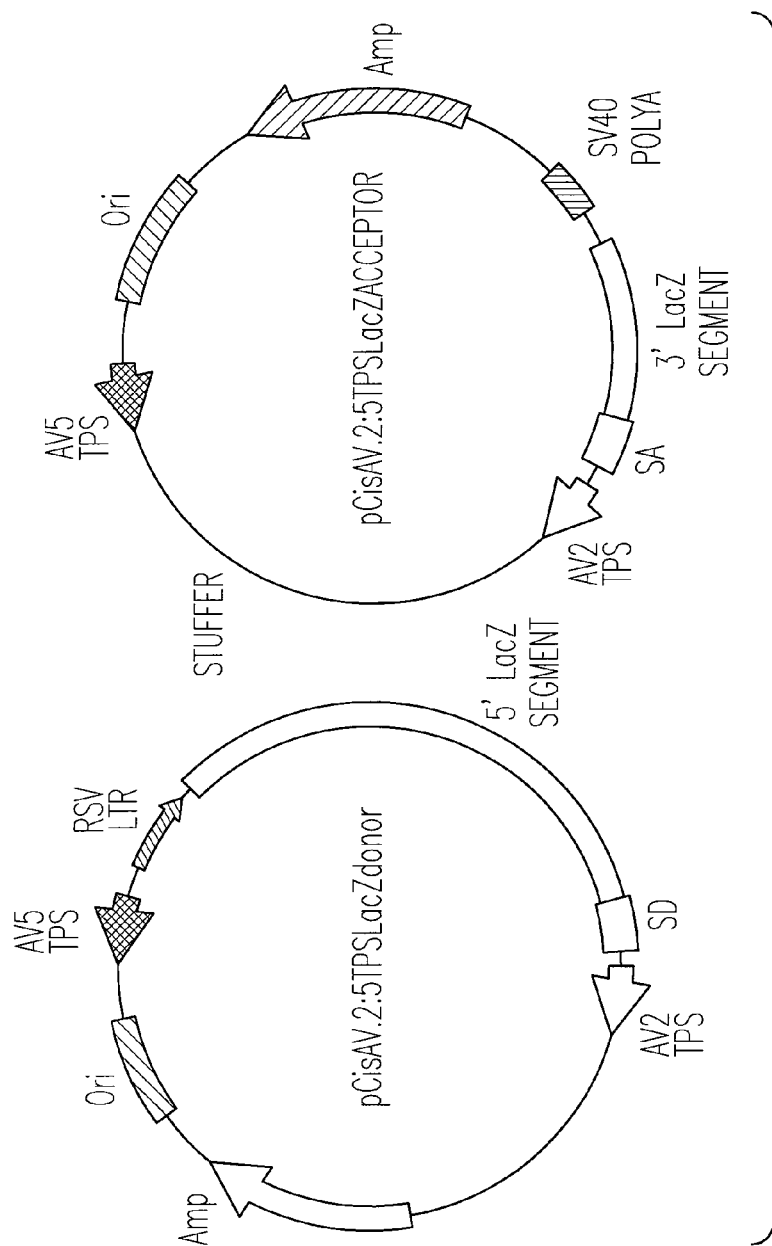
FIG. 10. Dual intravector heterologous TPS rAAV vectors and anticipated heterodimer structure. The split LacZ minigene is an example for any large minigene over a single rAAV packaging limit. (A) The proviral plasmids used to generate the intravector heterologous AV 2:5 TPS LacZ trans-splicing dual vector set. (B) Viral structure of the intravector heterologous AV 2:5 TPS vectors. (C) Homologous recombination between AAV-2 TPSs and AAV-5 TPSs results in formation of tail-to-head heterodimers functionally competent for LacZ gene expression. (D) Head-to-head heterodimer formation is predicted to be reduced by the low sequence homology of the AAV-2 and AAV-5 TPS.
Figure 10B:
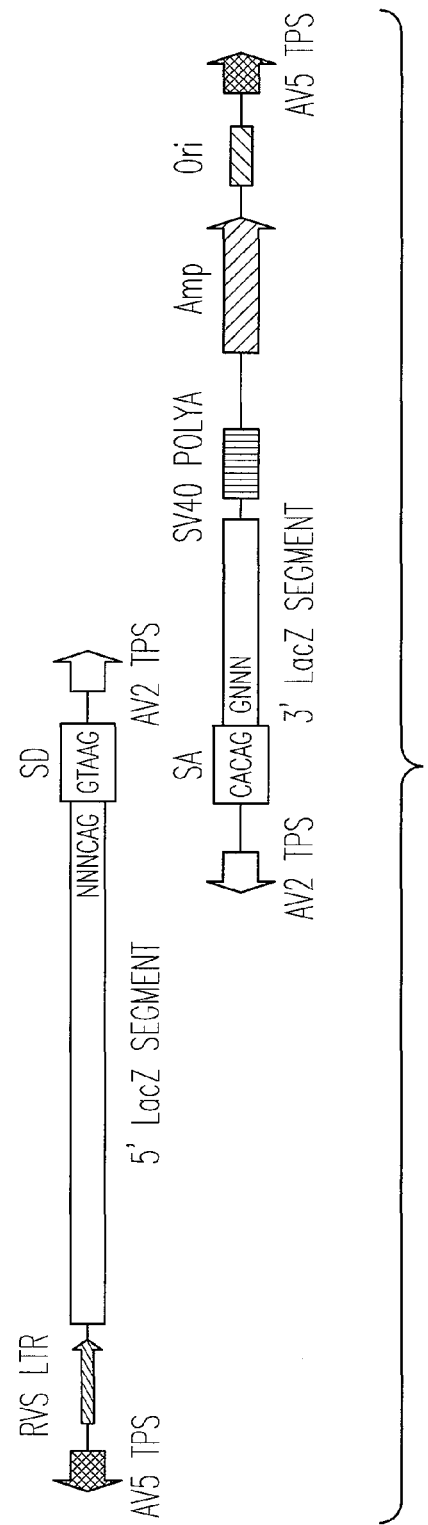
Figure 10D:
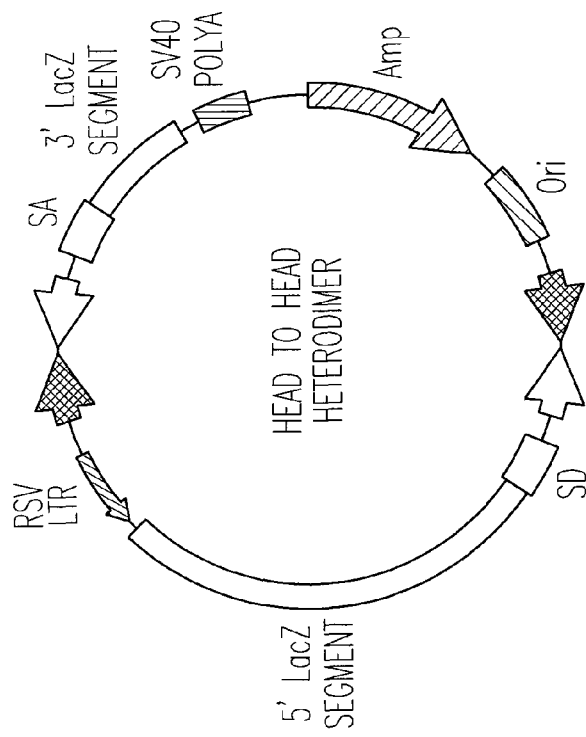
Figure 10C:
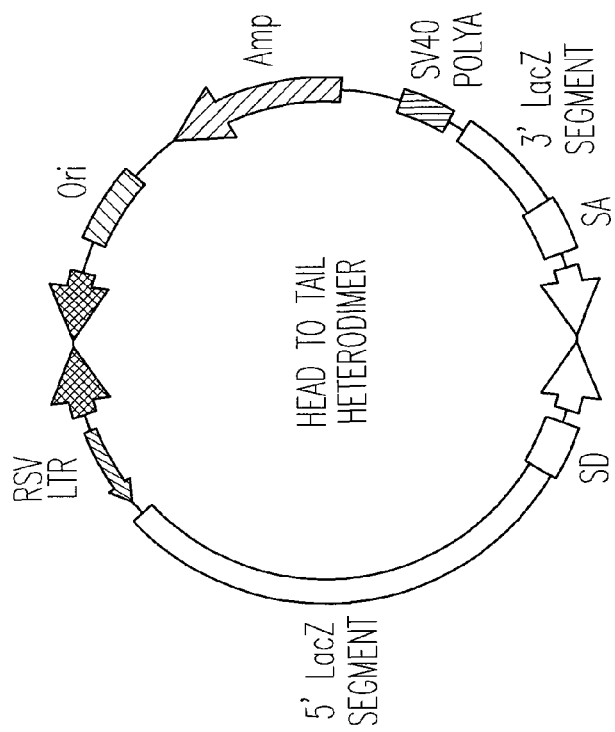

A dual vector trans-splicing approach was used to assess the extent of intermolecular recombination by reconstituting a LacZ transgene product from two LacZ mini-gene exons independently delivered with two vectors. In this context, reconstitution of β-galactosidase is a direct measure of directional H-T intermolecular recombination events between two independent viral genomes. To this end, an intravector heterologous AV2:5 TPS vector set (AV5:2 LacZdonor and AV2:5 LacZacceptor) was constructed as showed in FIG. 10A and the efficiency for intermolecular recombination of the set was compared against a homologous TPS vector set (AV2:2 LacZdonor and AV2:2 LacZacceptor). Both donor and acceptor viral genomes were packaged into AAV-2 and AAV-5 capsid virions for analysis in HeLa cells. The infectious titer of all eight viruses was compared individually by infecting HeLa cells with equivalent physical titers ($2.5 \times 10^3$ DRP/cell) and assessing DNA uptake into cells at 16 hours post-infection. This method was used since an appropriate cell line was not available for mobilization assays for intravector heterologous TPS vectors (i.e., requiring both type 2 and 5 Rep proteins). These studies confirmed that all 8 viral stocks (AV2:2 LacZdonor, AV2:2 LacZacceptor, AV5:2 LacZdonor and AV2: 5lacZdonor in either AAV-2 or AAV-5 capsids) delivered similar levels of viral DNA into cells for each of the capsid serotypes (data not shown). These data support functional analyses demonstrating a similar ability of intravector heterologous TPS vectors to homologous TPS vectors to express a GFP encoded transgene in HeLa cells (FIG. 7E).

Figure 11A:
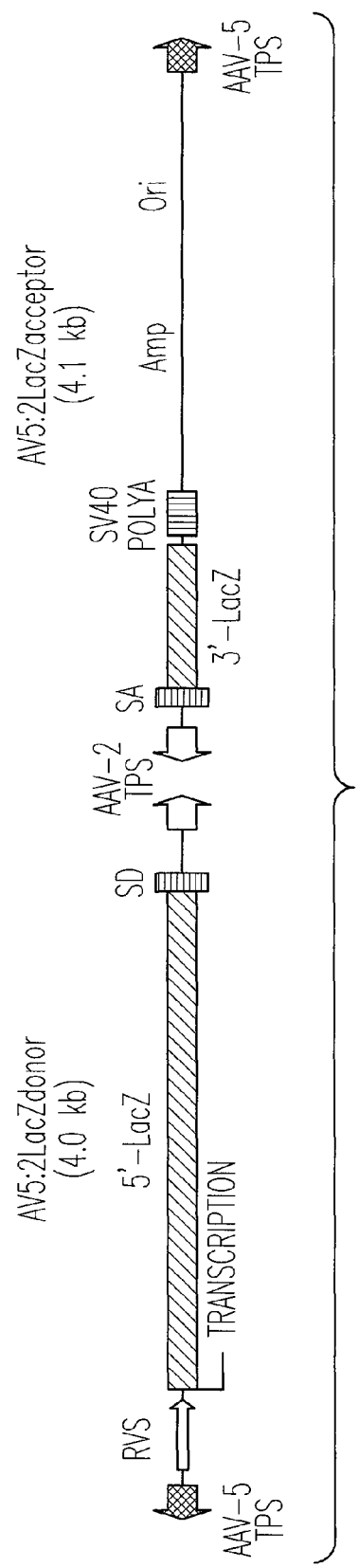
FIG. 11. Comparison of dual vector heterodimerization between intravector heterologous TPS vectors and homologous TPS vectors. Dual vector reconstitution of a LacZ-minigene was used to evaluate the extent of tail-to-head intermolecular recombination with intravector heterologous TPS vectors and homologous TPS vectors. (A) Schematic representation of the intravector heterologous TPS trans-splicing viral genomes, AV5:2 LacZdonor and AV2:5 LacZacceptor, used to generate AAV-2 serotype viruses (AV5:2/2LacZdonor and AV2:5/2LacZacceptor) or AAV-5 serotype viruses (AV5: 2/5LacZdonor and AV2:5/5LacZacceptor). AV2:2/2LacZdonor and AV2:2/2LacZacceptor viruses (not shown) had similar structure but contained AAV-2 TPSs on both ends of the genome. (B-D) HeLa cells were infected at an MOI of 2500 particles/cell with each virus alone or in combination as indicated. β-galactosidase activity was quantified at 3 days post-infection. The analysis was performed with both (B) AAV-2 encapsidated virus and (C) AAV-5 encapsidated virus. (D) Mixing experiments using combinations of intravector heterologous TPS, and intravector homologous TPS donor and acceptor vectors were also performed to assess sequence specificity in TPS recombination. Vector combinations are schematically shown on the graph with open and closed arrowheads indicating AAV-2 and AAV-5 TPSs, respectively. Data represent the mean (+/−S.E.M) of 7 independent infections.
Figure 11B:
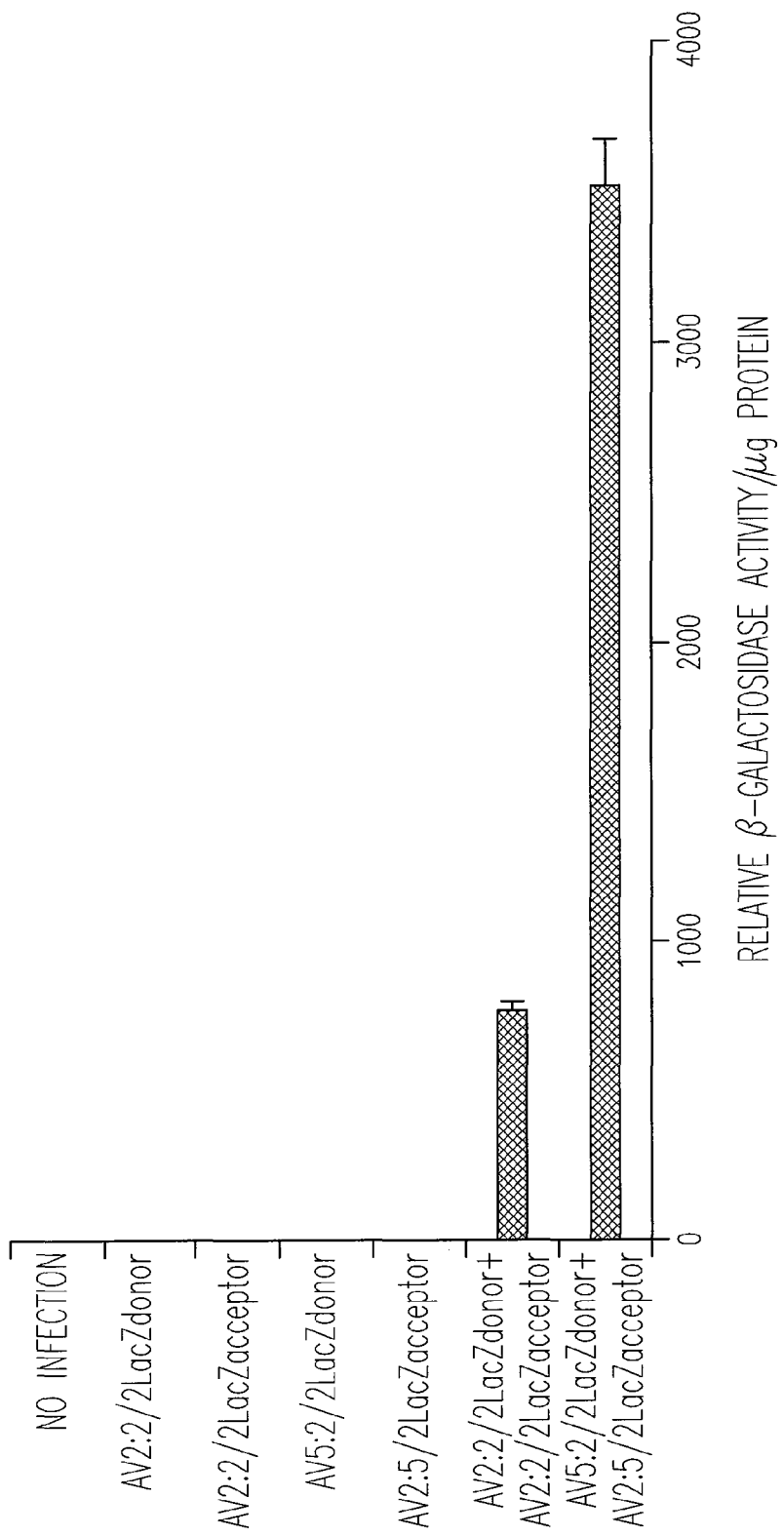
Figure 11C:
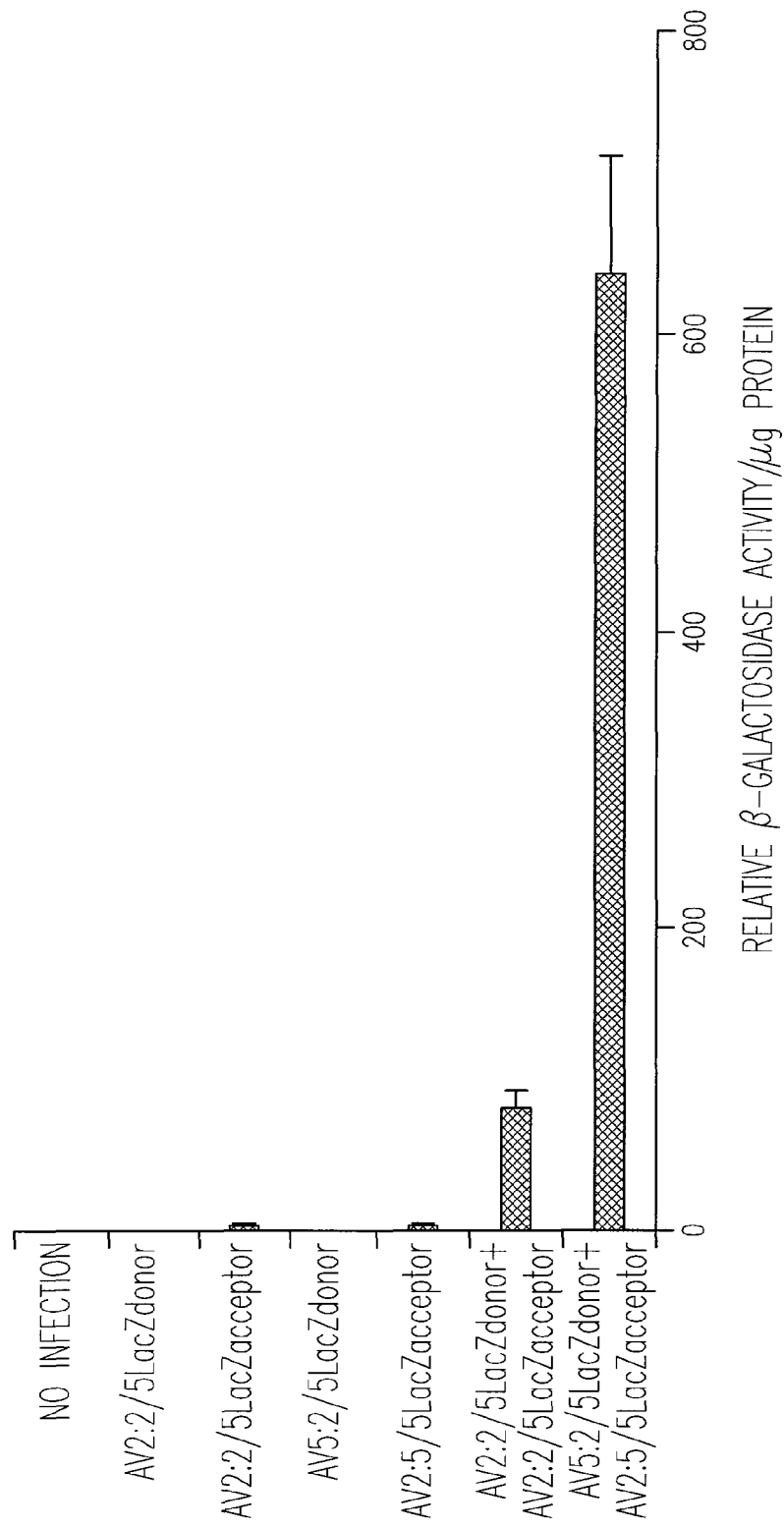

Functional studies evaluating the efficiency of intermolecular concatamerization were similarly performed in HeLa cells co-infected with donor and acceptor vectors for each serotype and TPS configuration (FIGS. 11B and C). Relative α-galactosidase activities from each infection were assayed 3 days post-infection. Results from these experiments demonstrated that intravector heterologous TPS dual vector sets were 6-fold (FIG. 11B) or 10-fold (FIG. 11C) more effective at reconstituting a functional LacZ gene product than homologous TPS vectors with AAV-2 or AAV-5 capsids, respectively. Given the findings that intravector heterologous TPS vectors preferentially increase the abundance of linear form genomes (FIG. 11B), these findings suggest that linear concatamerization of AAV genomes can occur through TPS homologous recombination in a sequence-specific fashion. In this context, sequence homology of the two type of TPSs in intravector heterologous TPS vectors would be expected to preferentially drive the formation of functional heterodimers.

Figure 11D:
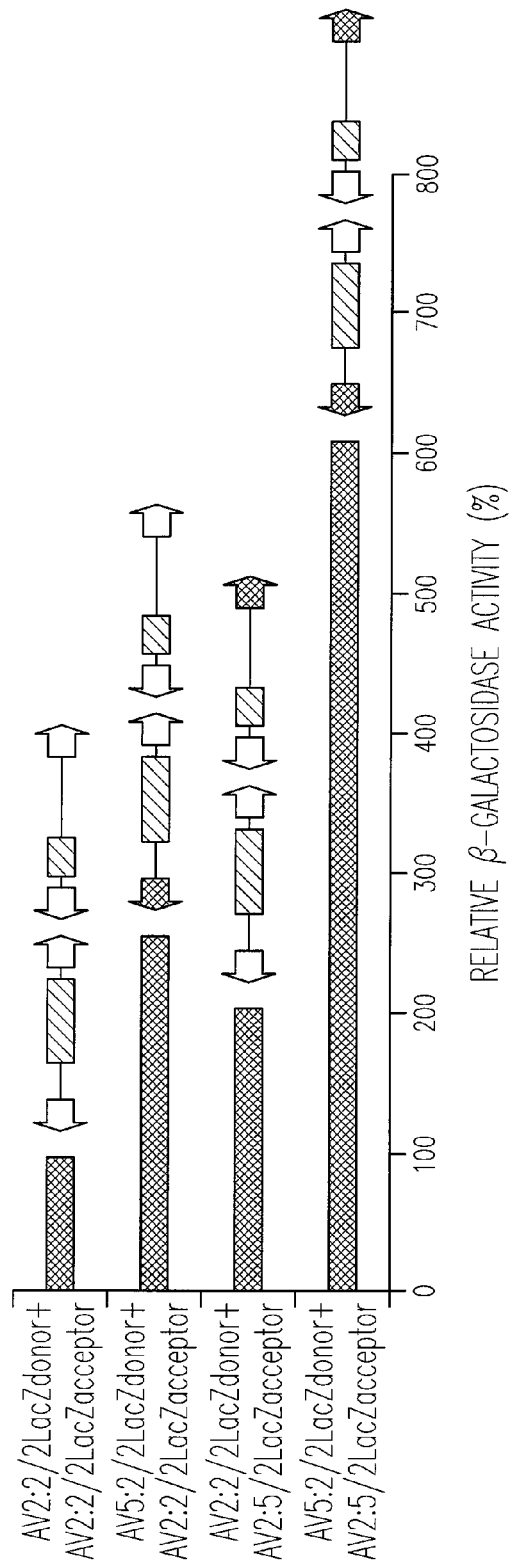
Figure 12A:
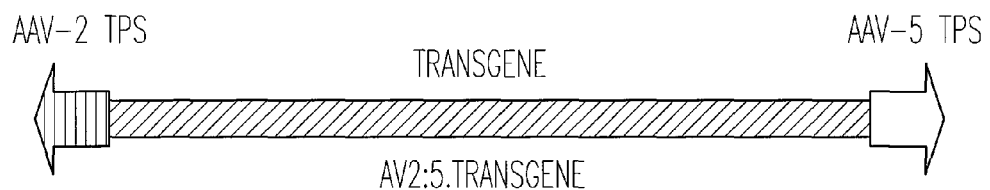
FIG. 12. Schematic representation of intravector heterologous TPS rAAV vectors. Panel (A) shows an intravector heterologous TPS rAAV with TPSs from different AAV serotypes (rAV2:5 transgene). Panel (B) shows a pseudo TPS rAAV vector. "2" and "5" represent the two TPSs of either AAV-2 or AAV-5 origin and "P" represents a pseudo TPS. Panel (C) shows the corresponding plasmid vector.
Figure 12B:
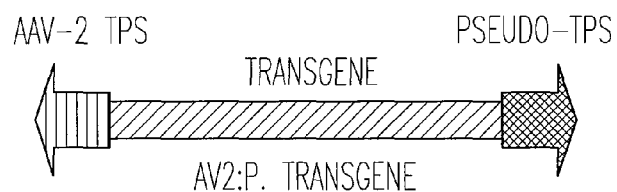
Figure 12B:
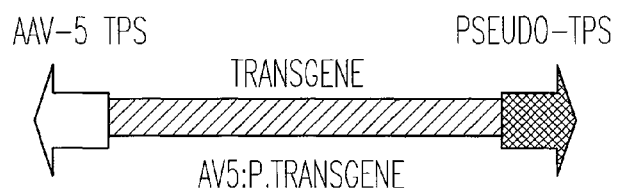
Figure 12C:
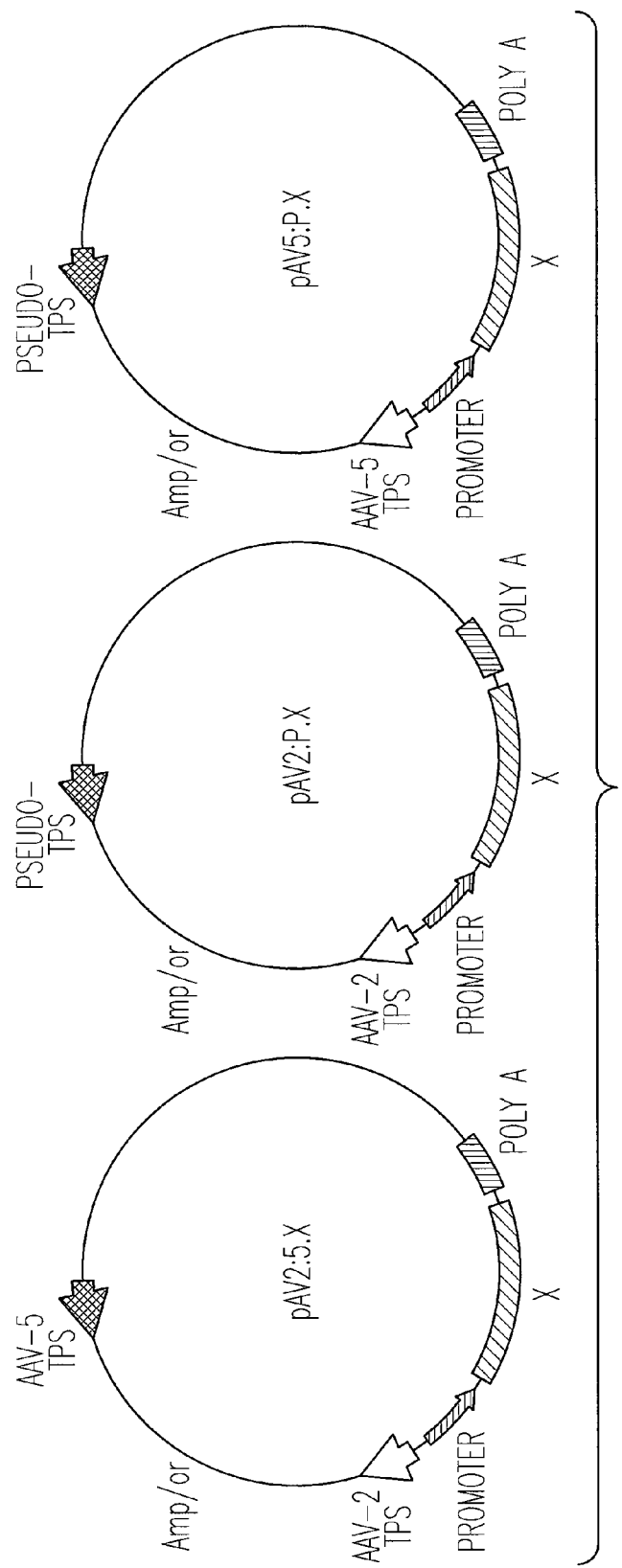

To provide further evidence for sequence restricted TPS recombination in the formation of heterodimers, the efficiency of trans-splicing between various combinations of a homologous TPS and intravector heterologous TPS vector sets was compared. As expected, results from these experiments demonstrated that AV5:2/2lacZdonor and AV2:2/2lacZacceptor or AV2:2/2lacZdonor and AV2:5/2lacZacceptor vector combination gave an intermediate level of transgene reconstitution to homologous and intravector heterologous TPS vector sets (FIG. 11D). These results provide further evidence for the importance of TPS sequences in heterodimer formation.

Pseudo TPSs

Figure 13A:
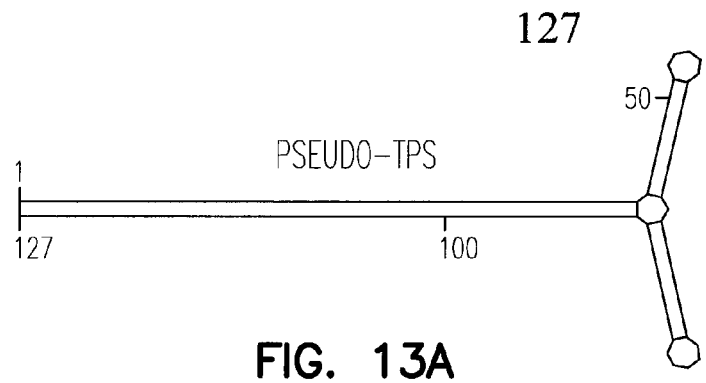
FIG. 13. (A) Sequence and structure of an exemplary pseudo TPS having SEQ ID NO:3. The primary structure of a pseudo PS is palindromic, as is an AAV-2 or AAV-5 TPS, but the pseudo PS shares little or no homology with AAV TPS sequences. (B) Sequence and structure of an AAV-2 TPS (SEQ ID NO: 1) within AAV-2 5' ITR. (C) Homology alignment of a pseudo PS (SEQ ID NO:3) and an AAV-2 TPS (SEQ ID NO: 1) generated by the Higgins arithmetic method (Higgins et al., 1989). The cleavage site in the terminal resolution site (trs) of the AAV-2 ITR is indicated with a vertical arrow and the D-sequence is presented by bold letters. Underlined letters in both sequences indicate sequences for forming a loop structure (B-C sequences for AAV-2 TPS). The predicted second structure of the pseudo PS (panel D) and an AAV-2 TPS (panel E) is a similar stem-loop hairpin conformation. There is little sequence homology between a pseudo PS and an AAV-2 TPS (sequence identity calculated by a manual comparison shows about 31% identity in the A region, about 28% identity and about 56% identity in the B and C regions, and about 39% identity overall, while homology calculated using the Higgins arithmetic method shows about 9.7% homology in the A region, about 36.3% homology in the B region and 0% homology in the C region, and about 8.6% homology overall) but both share the same stable stem-loop hairpin conformation.
Figure 13B:
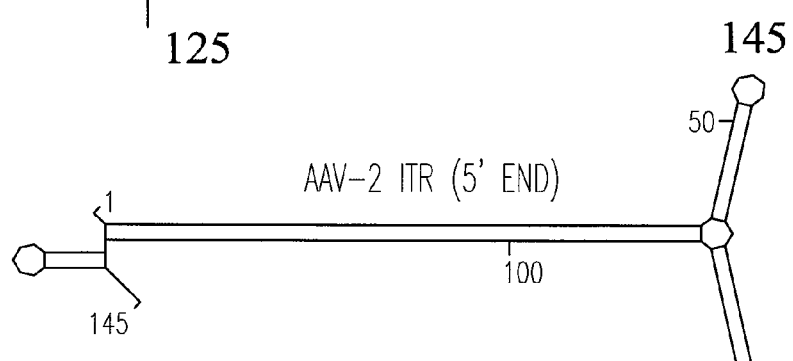
Figures 14A, 14B:
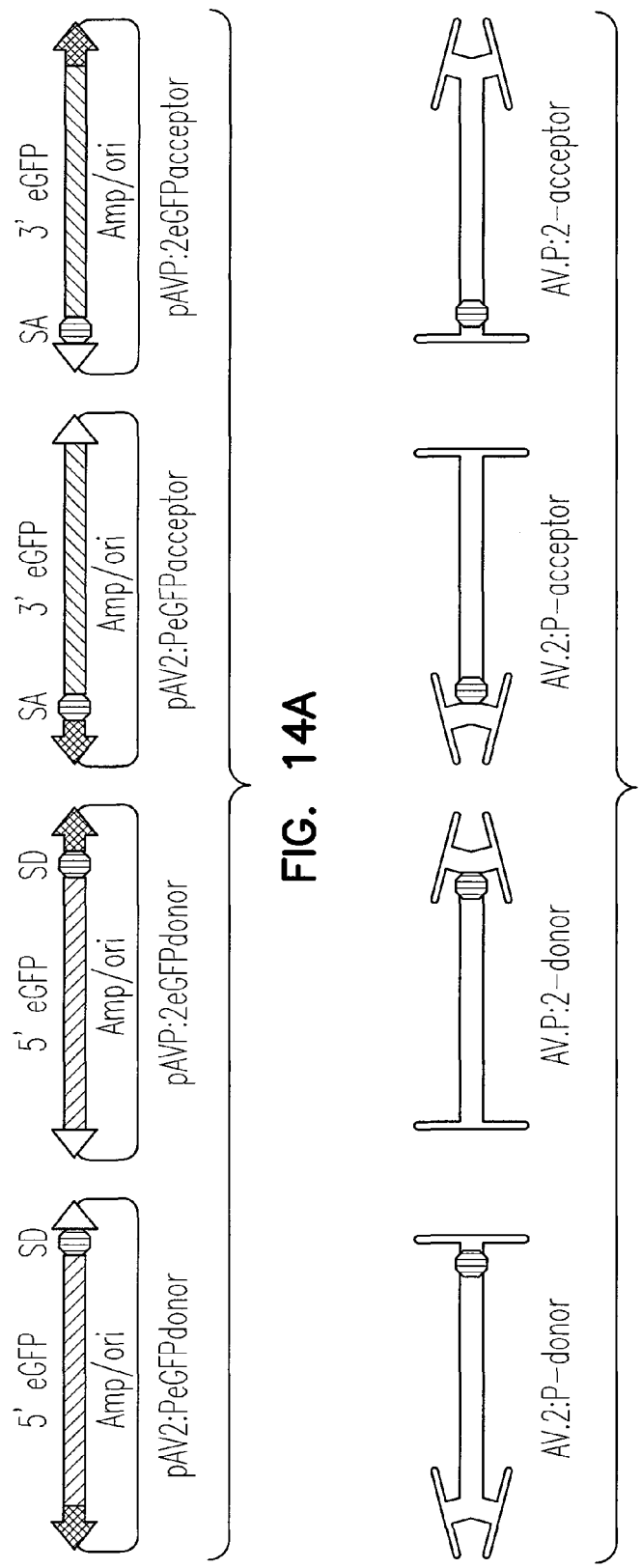
FIG. 14. Intravector heterologous TPS AAV with a pseudo TPS for trans-splicing. (A) Proviral plasmids used to generate intravector heterologous TPS rAAV vectors containing a pseudo TPS. The filled arrow represents a wild type AAV-2 TPS, the open arrow is for a pseudo TPS. SD: trans-splicing donor signal sequence; SA: trans-splicing acceptor signal sequence. (B) Schematic representation of intravector heterologous TPS rAAV vectors with a AAV-2 TPS and a pseudo TPS at either end. The lack of a terminal resolution site in viral genomes with the pseudo TPS may result in those genomes being packaged as a self-complementary double stranded genome with a closed end at the pseudo TPS and an open end at the AAV-2 TPS. (C) A Southern blot assay of the pseudo TPS rAAV. Viral DNA extracted from AV.2:P-donor (lane 1), AV.P:2-donor (lane 2), AV.2:P-acpt (lane 3) and AV.P:2-acpt (lane 4) was resolved in an agarose gel and visualized by a $^{32}$P labeled eGFP probe. (D) The reconstitution of the split eGFP mini gene delivered by pseudo TPS rAAV trans-splicing dual vector sets.
Figure 14C:
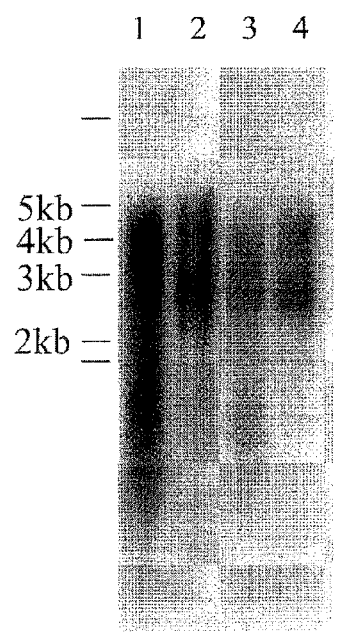
Figure 14D:
Figure 14D:
Figure 14D:
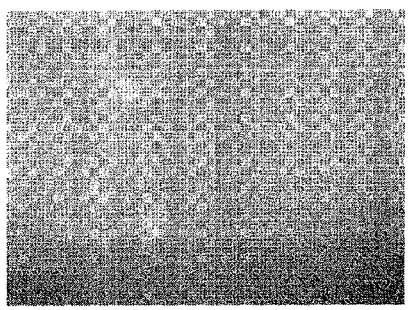
Figure 14D:
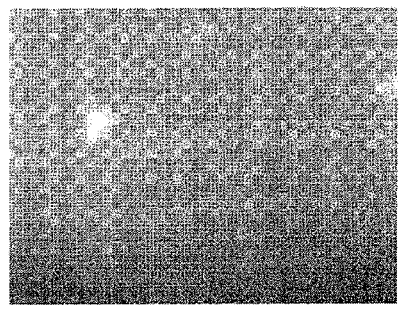
Figure 15A:
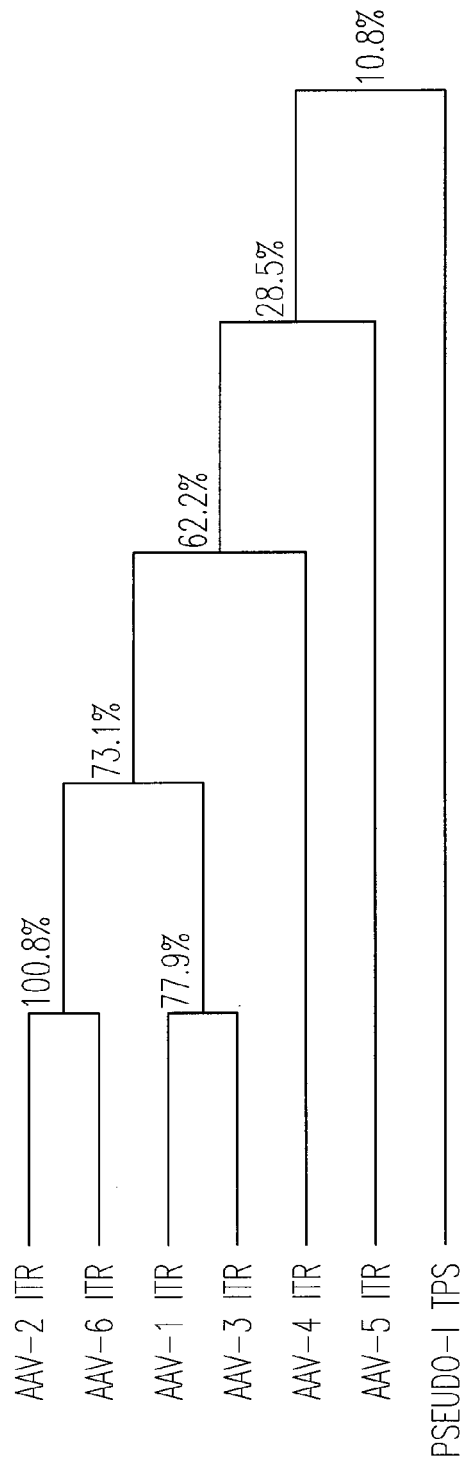
FIG. 15. (A) Homology between various TPSs. (B) Sequence alignment of various TPSs. The homology analysis and alignment were generated by DNAsis v3.7 software with the Higgins arithmetic method. Pseudo TPS (SEQ ID NO:3); AAV-1 TPS (SEQ ID NO:4); AAV-2 TPS (SEQ ID NO: 1); AAV-3 TPS (SEQ ID NO:5); AAV-4 TPS (SEQ ID NO:6); AAV-5 TPS (SEQ ID NO:2); and AAV-6 TPS (SEQ ID NO: 11).
Figure 16A:
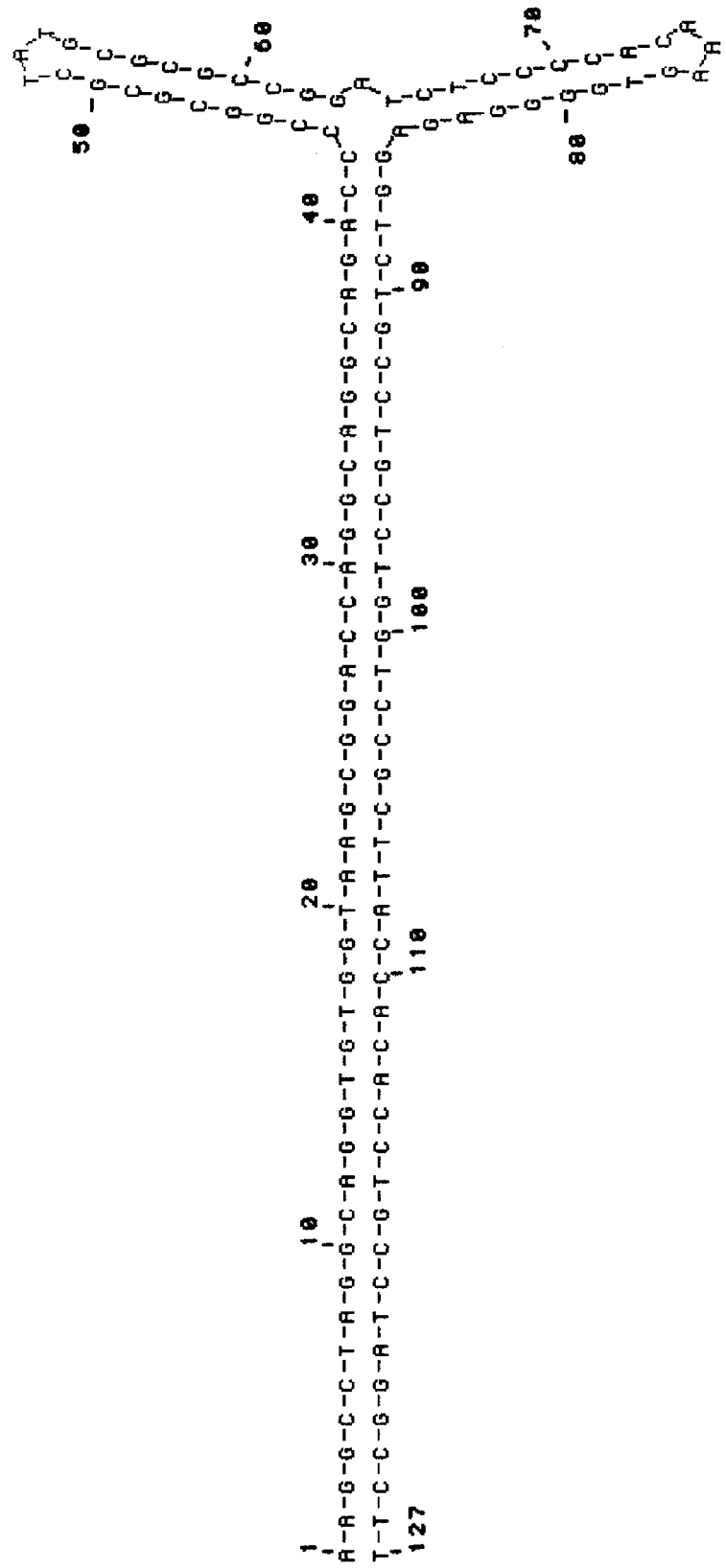
FIG. 16. Secondary structures for Pseudo TPS P1 (SEQ ID NO:3) (A), AAV-5 TPS (SEQ ID NO:2) (B), Pseudo TPS P3 (SEQ ID NO:8)(C), AAV-2 TPS (SEQ ID NO:1)(D), Pseudo TPS P2 (SEQ ID NO:7)(E), comparison of P1, AAV-2 TPS and AAV-5 TPS (F), and comparison of Pseudo P1, P2, P3, AAV-2 TPS and AAV-5 TPS (G).
Figure 16B:
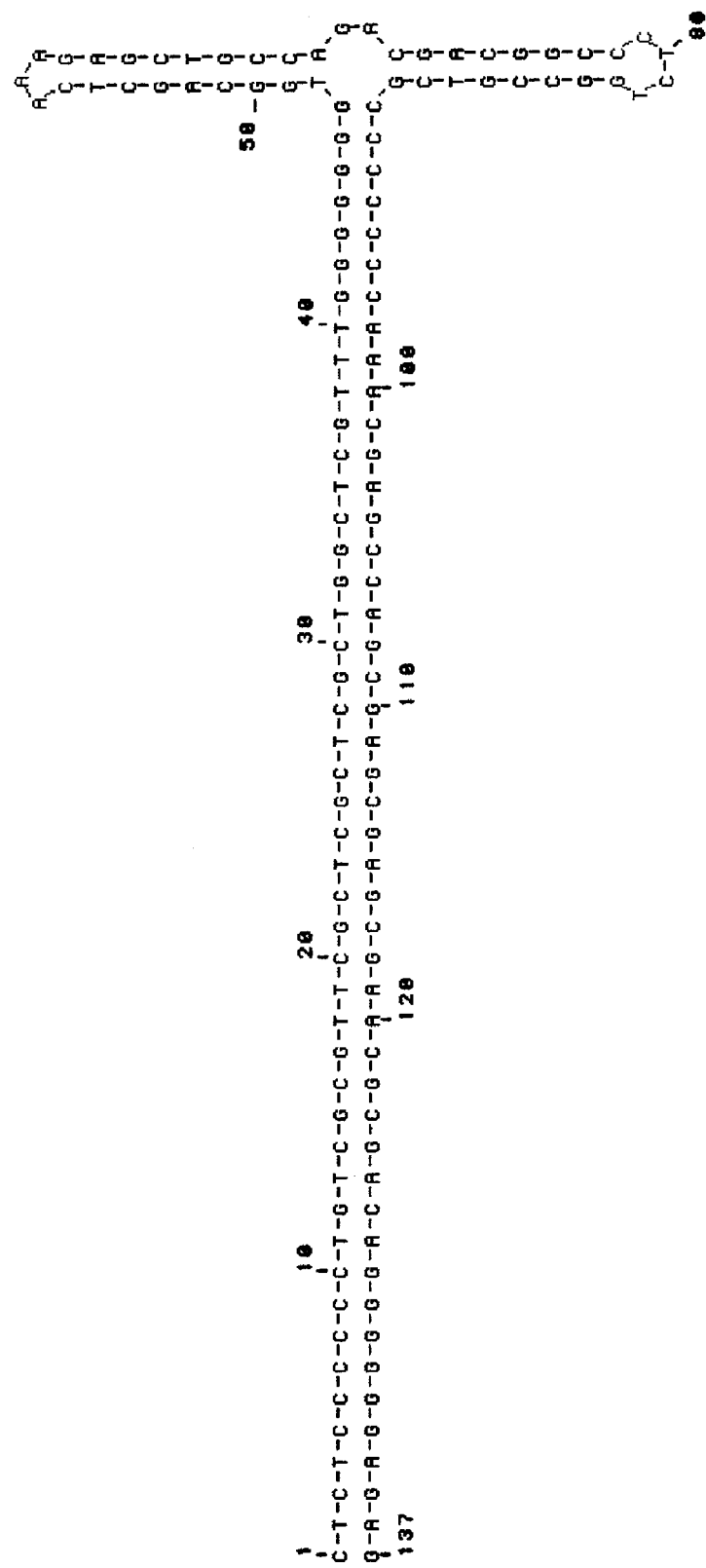
Figure 16C:
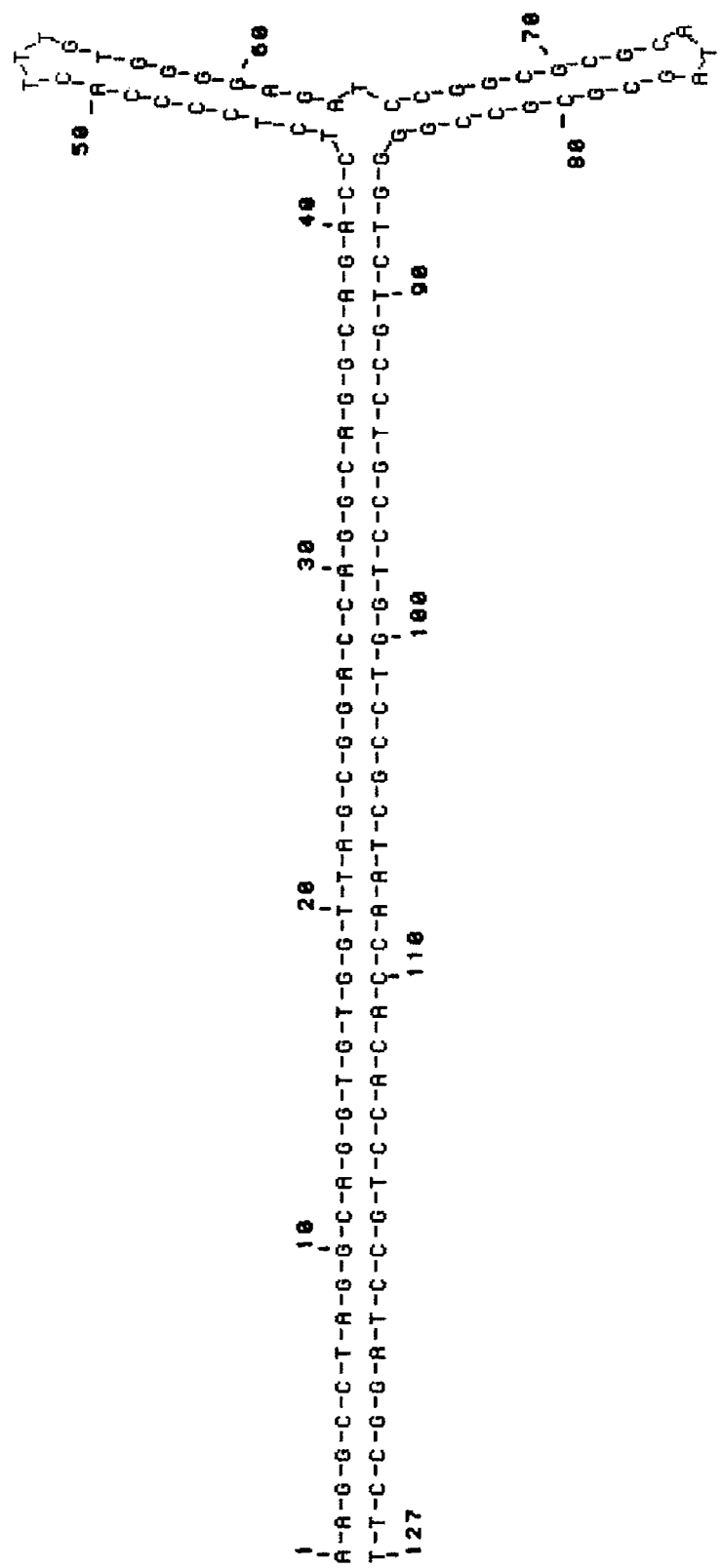
Figure 16D:
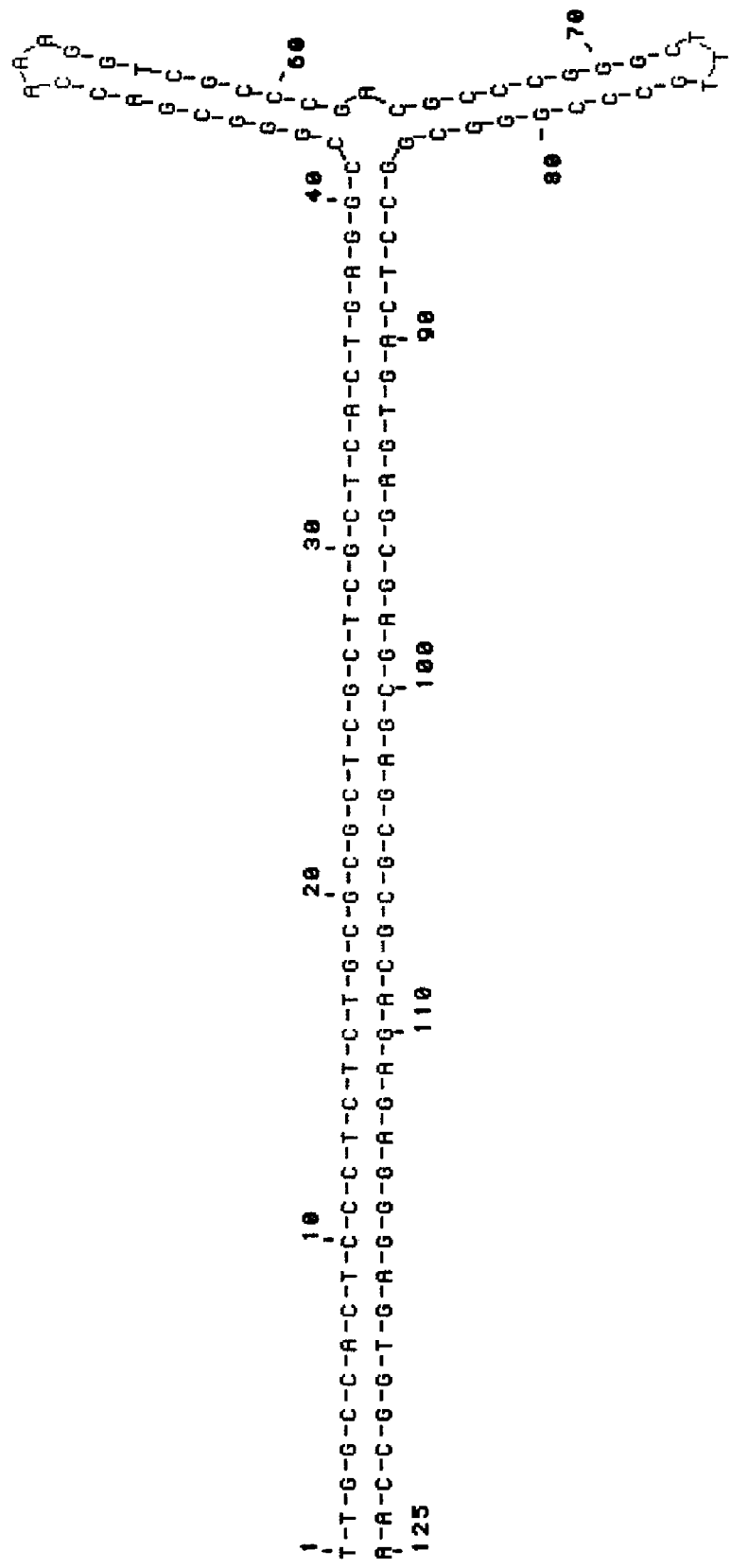
Figure 16E:
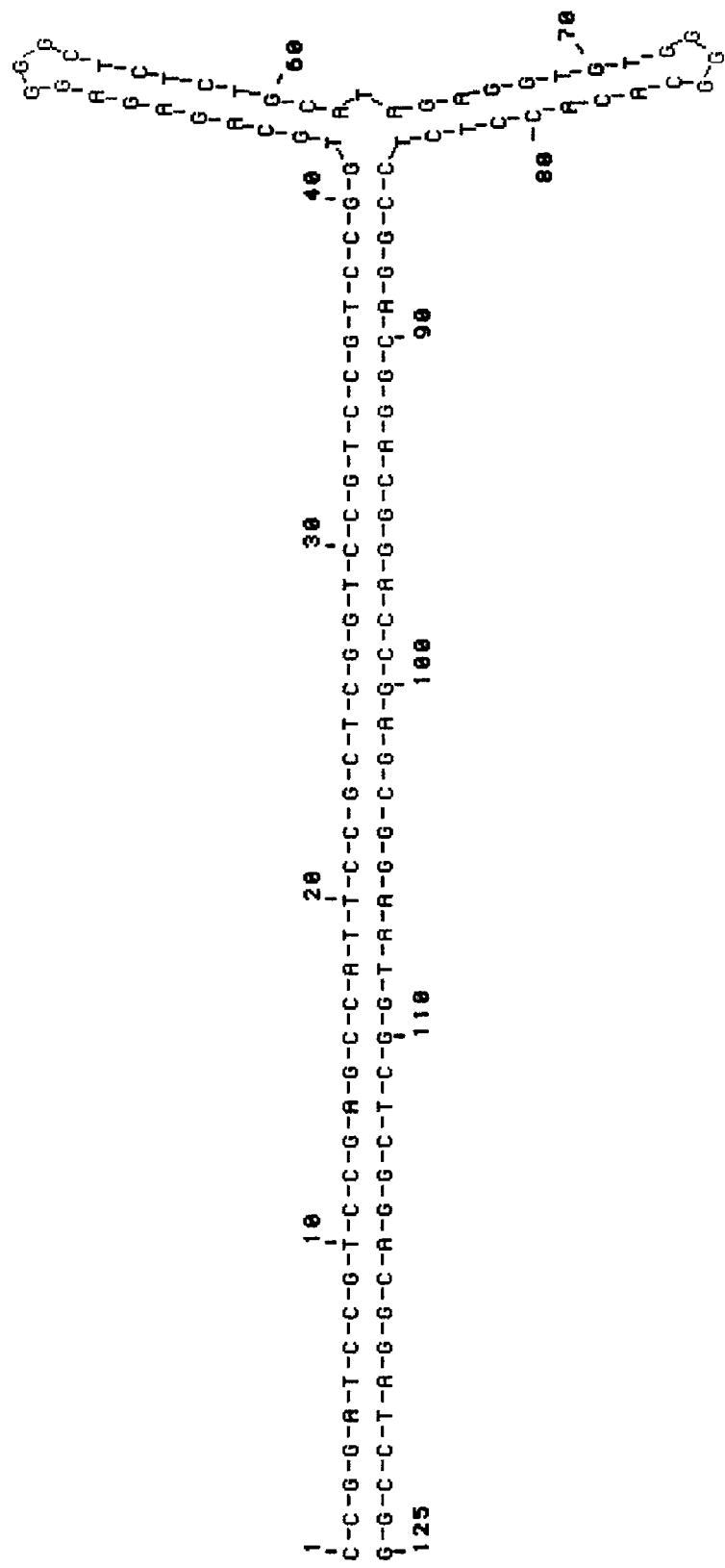
Figure 16F:
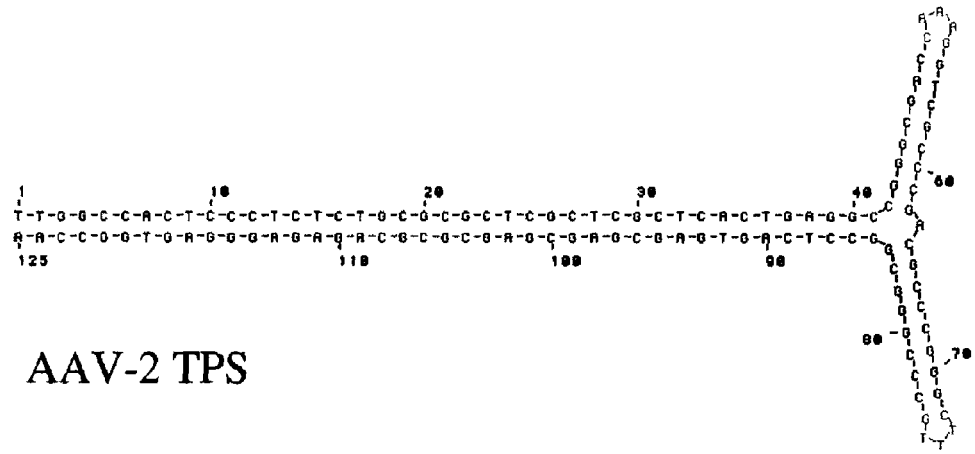
Figure 16F:
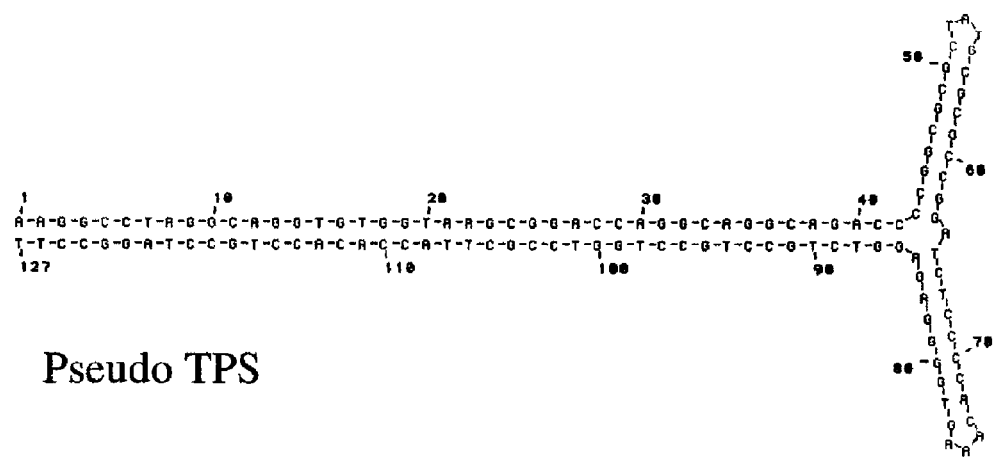
Figure 16F:
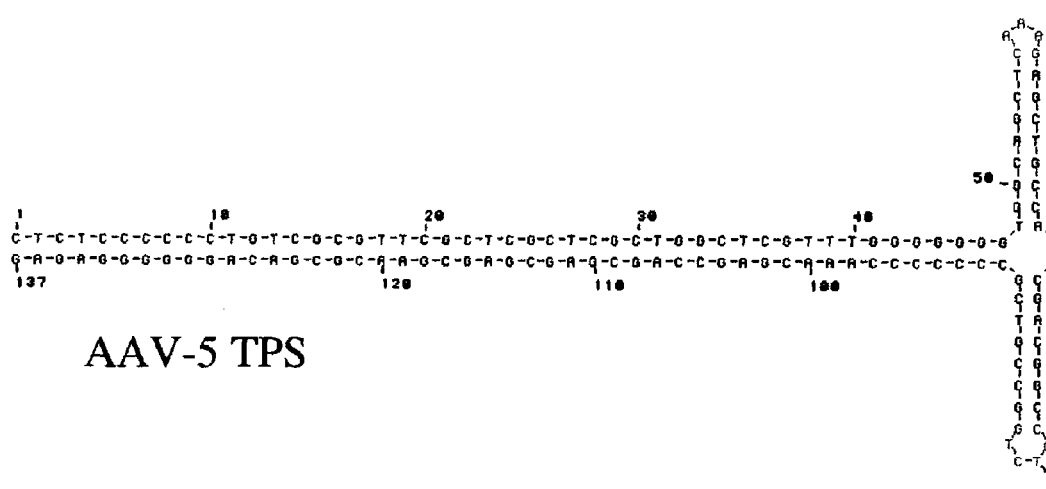

As described above, rAAV with intravector heterologous TPSs is useful for directional intermolecular recombination of two or more rAAV in cells. The divergence of the two TPSs in an intravector heterologous rAAV vector may be the result of TPSs from different AAV serotypes, of a TPS from one serotype of AAV and a pseudo TPS, i.e., a synthetic DNA fragment with a palindromic structure and a stem or stem-loop secondary structure, e.g., one with little or no sequence homology to a TPS from one or more AAV serotypes (FIGS. 12 and 13), or two different pseudo TPSs. In intravector heterologous TPS rAAV vectors with a native AAV TPS followed by a D-sequence and a pseudo TPS which lacks a D-sequence, the proviral genome length of the intravector heterologous TPS virus is only 2 to 2.5 kb, half that of the wild type AAV genome. Such intravector heterologous TPS viruses contain self-complementary or double stranded genomes inside the viral capsid.

A rAAV vector containing a pseudo TPS and an intact minigene expression cassette (i.e., promoter, transgene and polyA signal) or partial exons of the minigene with a splicing signal, was cloned as a proviral genome in an E. coli plasmid with a pUC19 backbone and propagated in bacteria. The pseudo PS was generated by systematically changing in a native AAV TPS, e.g., one or more G residues to A, C or T residues, one or more A residues to G, C or T residues, one or more C residues to T, G or A residues, one or more T residues to C, G or A residues, or any combination thereof, so that the resulting sequence is capable of forming a stem loop structure, has a free energy (e.g., determined as described in Table 3) similar to that of a native AAV PS, e.g., within 25 kcal/mol, and has a $T_m$ (e.g., determined as described in Table 3) similar to that of a wild type AAV TPS, e.g., within 8° C. In one embodiment, a native AAV PS is divided into 4 segments, i.e., A, B-B', C-C' and A'. When a nucleotide in the A segment is changed, a corresponding change is made at the matching position in the A' sequence. The G-C percent of the whole sequence is greater than 40%, e.g., 55%, 65%, or more, which would bring the $T_m$ to greater than 70° C., e.g., about 81° C. to 94° C., including about 85° C. to about 89° C. (89° C. is the $T_m$ of the native AAV-2 TPS). When changing "hinge nucleotides" at the joint junction of A-B, B-B', B'-C', C'-C, and C-A', secondary structure predictions are employed for the resulting sequence to verify conservation of the secondary structure. In addition, generally the number of unpaired nucleotides at the junctions is not altered. For instance, in one embodiment, 3 unpaired nucleotides are at the B-B' or C-C junction, and in another embodiment, 1 unpaired nucleotide is at the B-C junction. In one embodiment, the nucleotides at the RBE (Rep protein binding element) and trs (terminal resolution site) are altered so as to inhibit Rep binding and cleavage at the trs, respectively. Optionally, such motif(s) are not introduced or present in the final to the sequence.

One exemplary pseudo PS has SEQ ID NO:3 (P1). The insertions in P1 may increase the stability of the secondary structure. Additional examples of a pseudo TPS include P2 (SEQ ID NO:7; CCGGATCCGTCCGAGCCATTC-CGCTCGGTCCGTCCGTCCGGTGCAGA GAGGGGCTCTCTGCATAGAGGT-GTGGGGCACACCTCTCCGGACGGAC GGAC-CGAGCGGAATGGCTCGGACGGATCCGG; $T_m$ 88° C.; secondary structure energy −146 kcal/mol) and P3 (SEQ ID NO:8; AAGGCCTAGGCAGGTGTGGTAAGCGGAC-CAGGCAGGCAGACCTCTC CCCACTTTGTGGG-GAGATCCGGCGCGCATAGCGCGCCGGGGTCTGCC TGCCTGGTCCGCTTACCACACCTGCCTAGGCCTT; $T_m$ 87° C.; secondary structure energy −162 kcal/mol). P3 is has the same A-stem as pseudo TPS P1, but the B-C loop is changed. Both P2 and P3 share the same stem-loop secondary structure as AAV-2 but have low homology to the AAV-2 TPS sequence (FIG. 16). To generate homology alignments, the Higgins arithmetic method was used. Sequences were aligned using a gap penalty of 5, a K-Tuple of 4 (for DNA and RNA), a fixed gap penalty of 10, and a floating gap penalty of 10.

Another pseudo PS, N1, has the following sequence: tactatcagcgcataaaatcactgactagtatcttgcctaCCGGGCGACCA AAGGTCGCCCGACGCCCGGGCTTTGC-CCGGGCGGtaggcaagatactagtcagtgattttatccctgatagta (SEQ ID NO:9). The 80 nucleotide palindrome sequence in N1 for the A-A' stem (in lower case) was generated by randomly changing the nucleotides, however, the B-B'-C'-C loop (in upper case and underlining for the hinge) between A and A' is from AAV-2. N², has the same A-A' stem as N1 (random), but the B-C loop was randomly generated to yield: tactatcagcgcataaaatcactgac-tagtatcttgcctaCGGCTAGTGCATAGCACTAGCCAG GATGGAGCTATGCTCCATCCGtaggcaa-gatactagtcagtgattttatgcgctgatagta (SEQ ID NO: 10) (upper case for the B-C loop, underlining for the hinge, and lower case for the A-A' stem). Although the G-C percentage and the $T_m$ value are lower, the N1 and N2 TPSs also have the same stem-loop secondary structure as the AAV-2 TPS. Nevertheless, as the $T_m$ is lower, the secondary conformation of N1 and N2 might be not as stable as P1-P3 (FIG. 17). Preferably, the GC % in a pseudo TPS is at least 65%.

TABLE 3

| TPS[a] | Tm[b] | Secondary Structure Energy (kcal/mol)[c] |
|---|---|---|
| AAV-1 | 89° C. | −156 |
| AAV-2 | 89° C. | −161 |
| AAV-3 | 87° C. | −152 |
| AAV-4 | 87° C. | −152 |
| AAV-5 | 89° C. | −176 |
| AAV-6 | 89° C. | −161 |
| Pseudo (SEQ ID NO:3) | 87° C. | −162 |

[a]calculations for AAV-1-4 and 6 were based on 125 bp stem-loop
[b]based on URL available at mbcf.dfci.harvard.edu/docs/oligocalc.html
[c]based on URL available at www.basic.nwu.edu/biotools/oligocalc.html When the intravector heterologous TPS rAAV vector is transfected into human 293 cells, the intravector heterologous TPS viral genome can be excised from the proviral plasmid and packaged with any type AAV capsid protein to assemble infectious virions if all necessary viral proteins are provided in trans. For example, 293 cells transfected with the intravector heterologous TPS proviral plasmid pAV2:P.transgene, adenovirus helper plasmid pAd4.1, AAV-2 helper pAV.Trans2 and AAV-5 Rep protein expression plasmid pRepS, yields an intravector heterologous TPS virus, AV2:P/2.transgene (about $1\times10^{11}$ to $1\times10^{12}$ DRP/ml), which is encapsidated with AAV-2 capsid; while 293 cells transfected with pAd4.1, pAV2:P.transgene, AAV-5 helper pAV.Trans5 and AAV-2 Rep expression plasmid pRep2, yields an intravector heterologous TPS virus, AV2:P/5.transgene (about $1\times10^{12}$ DRP/ml), which is encapsidated with AAV-5 capsid.

HeLa cells were infected with each virus at the MOI of 1000 DRP/cell, and eGFP fluorescent photomicrographs were taken at 48 hours post-infection. Results demonstrated that AAV dimerization is a sequence dependent process (FIG. 14). AV2/AV2 TPS hybridization can result in high efficient recombination and reconstitution of EGFP expression (the co-infection of AV.P:2-donor pluc AV.2:P-acpt). Similarly, Pseudo/Pseudo TPS (without a D sequence) hybridization reconstituted EGFP expression at the same efficiency as the AV2/AV2 (the co-infection of AV.2:P-donor plus AV.P:2-acpt). A very low efficiency of eGFP expression reconstitution was observed after infection with AV.2:P-donor plus AV.2:P-acpt or AV.P:2-donor plus AV.P:2-acpt. The efficiency was about 60-fold lower compared to vectors with homologous TPSs.

The molecular basis of the dual vector trans-splicing approach is TPS mediated intermolecular recombination. After the directional homologous intravector hybridization of two homologous TPSs, e.g., two pseudo TPSs, in different vectors each having a portion of a gene, the functional reconstitution of the gene is facilitated due to an increased level of head to tail heterodimers. As the intravector heterologous TPS rAAV has a significantly reduced capacity to form circular intermediate monomers through intramolecular TPS recombination, intermolecular recombination from the linear genomes predominates, leading to enhanced formation of heterodimers.

Discussion

Since circularization of rAAV genomes had only thus far been studied in the context of AAV-2 TPS containing genomes, a clearer understanding of this process for other divergent AAV serotypes may help understand the overall importance of circular genomes in the latent AAV life cycle. To this end, circular intermediate formation from AAV-5 TPS containing vectors was evaluated, since they are the least conserved in primary sequence to AAV-2. Using an AV5:5/5eGFP shuttle vector, 94% rescued circular intermediates had identical head-to-tail double-D TPS structure to that observed with the AV2:2/2eGFP vector. Although differences in the abundance of double-D TPS circular intermediates were observed with these cap5 and cap2 based vectors, due to differences in tropism for infection of HeLa cells, subsequent analysis comparing AV2:2/2eGFP and AV5:5/2eGFP viruses demonstrated indistinguishable abundance of circular double-D TPS genomes following infection. These results conclusively demonstrate that AAV-5 based vectors have similar efficiencies of circular intermediate formation as AAV-2 genomes, despite altered sequence homology of the TPSs. They also suggest that circularization is likely a common pathway for all serotypes of rAAV.

To more clearly understand what role the TPS plays in circular intermediate formation and subsequent concatamerization processes of rAAV viral genomes, a novel intravector heterologous AV2:5 TPS virus was prepared. Studies evaluating intravector heterologous TPS vectors (AV2:5/2eGFP and AV2:5/5eGFP) demonstrated that they were as functional as homologous TPS containing vectors (AV2:2/2eGFP and AV5:5/5eGFP) in expressing an encoded eGFP transgene. These findings demonstrated that homologous TPSs on both end of the viral genome are not necessary for efficient second strand synthesis. Interestingly, AV2:5/2eGFP virus had a substantially reduced ability to form circular intermediates as compared to AV2:2/2eGFP and AV5:5/2eGFP viruses. Furthermore, the circular intermediates that were recovered from intravector heterologous TPS virus were much more heterogeneous in structure and maintained deletion of both the TPSs and eGFP transgene. The abundance of double-D TPS intact circular genomes (containing eGFP and TPSs) was 60-fold less for AV2:5/2eGFP as compared to AV2:2/2eGFP and AV5:5/2eGFP viruses. These findings suggested that TPS-mediated homology at both ends of the viral genome is important for directing intramolecular circularization of the rAAV genome. However, this circularization process is not necessary for expression of encoded gene products. Hence, both the double stranded linear or circular transduction intermediates are competent for transgene expression.

Although studies using intravector heterologous TPS EGFP encoding vectors provided evidence for the importance of TPS sequences in self-circularization, similar requirement for the TPS in intermolecular recombination of viral genomes could not be directly assessed in these studies. Several precursors viral genome forms could conceivably be involved in the formation of intermolecular heterodimers and concatamers including: single stranded linear, double stranded linear, single stranded circular, or double stranded circular genomes. Recently, studies evaluating sequentially infected mouse tibialis muscles with LacZ trans-splicing vectors has suggested that recombination between double stranded viral genomes is the predominant pathway for concatamerization (Duan et al., 2003). These studies also suggested that the majority of internalized rAAV genomes remained as single stranded DNA, while only a small fraction is converted to functional double stranded transduction intermediates responsible for circularization and concatamerization. In muscle, circular monomer intermediates have been thought to play an important role as precursors to intermolecular recombination at double-D TPSs (Duan et al., 1998; Duan et al., 1999). However, direct evidence proving this hypothesis has been indirect and predominantly based on the types of intermolecular concatamers formed over time. In this context, both T-H and H—H/T-T intermolecular circular concatamers could be rescued from muscle Hirt DNA following co-infection with two independent vectors (Yan et al., 2000; Yang et al., 1999). These findings support the hypothesis that the process of recombination between circular intermediates is bi-direction and facilitated by double-D TPSs. Although these studies demonstrate the existing of circular concatamers with various genome orientations, they were not directly capable of evaluating the extent to which functional linear heterodimers were formed.

The finding in the present study demonstrating that intravector heterologous TPS vectors have a 60-fold reduced capacity to form double-D circular genomes provided the opportunity to directly evaluate the involvement of these structures in heterodimer formation using functional gene expression assays. Contrary to original hypotheses, intravector heterologous TPS vectors demonstrated increased directional heterodimer formation. These findings, together with homologous TPS vector and intravector heterologous TPS vector mixing experiments, support the involvement of sequence-specific TPS recombination between linear viral genomes. These findings are in stark contrast to previous data by others suggesting that linear concatamerization of AAV genomes in the liver occurs through an TPS-independent process (Nakai et al., 2003; Nakai et al., 2000). The discrepancy between these earlier findings in liver and the present studies are currently unknown, but could represent cell types specific differences.

Given the documented involvement of circular concatamers as AAV genome intermediates, the present study favors an interpretation that both linear and circular genomes can participate in concatamerization processes (FIG. 14). In the context of intravector heterologous TPS vectors, the equilibrium appears to have been shifted to favor linear concatamerization. These findings are reminiscent of findings in SCID mice for which increased linear concatamers are formed in the absence of DNA-Pkcs (Song et al., 2001). However, unlike previous analyses in muscle of SCID mice that did not demonstrate increased dual vector trans-splicing (Duan et al., 2003), the present studies with intravector heterologous TPS vectors favored a directional linear intermolecular recombination event (FIG. 14). Unlike a homologous TPS vector in which recombination between TPSs leads to random orientation of genome concatamers, intravector heterologous TPS vectors allow for directionally dependent concatamerization, which increases the number of functional genomes using dual vector trans-splicing approaches. Furthermore, the ability to alter concatamerization, and the ratio of circular to linear genomes, by altering TPS sequences may prove useful in other aspects of rAAV-mediated gene therapy such as extent of integration and/or stability of expression.

REFERENCES

Afione et al., *J. Virol.,* 70:3235 (1996).
Altschul et al., *J. Mol. Biol.* 215:403 (1990).
Altschul et al., *Nucleic Acids Res.* 25:3389 (1997).
Berns et al., Springer, Berlin; New York (1996).

Bett, A. J. et al., *Proc. Natl. Acad. Sci. USA*, 91:8802 (1994).
Blacklow, pp. 165-174 of Parvoviruses and Human Disease, J. R. Pattison, ed. (1988).
Carter et al., *Current Opinion in Biotechnology*, 3:533 (1992).
Carter et al., In "Handbook of Parvoviruses" Vol I (P.Tjissen, ed) CRC Press, Boca Raton, pp 255-282, 1989.)
Carter et al., *Int. J. Mol. Med.*, 6:17 (2000).
Carter et al., "Handbook of Parvoviruses" Vol I (P.Tjissen, ed. Vol) CRC Press, Boca Raton, 1989, pp 169-226.).
Chao et al., *Mol. Ther.*, 2:619 (2000).
Chiorini et al., *J. Virol.*, 73:1309 (1999).
Chiorini et al., *J. Virol.*, 73:4293 (1999).
Corpet et al., *Nucleic Acids Res.* 16:10881 (1988).
Duan et al. *J. Virol.*, 72:8568 (1998b).
Duan et al., *Human Gene Therapy*, 9:2761 (1998a).
Duan et al., *J. Clin. Invest.*, 105:1573 (2000b).
Duan et al., *J. Virol.*, 73:161 (1999).
Duan et al., *J. Virol.*, 77:4751 (2003).
Duan et al., *J. Virol.*, 8568 (1998).
Duan et al., *Mol. Ther.*, 4:383 (2001).
Duan et al., *Nat. Med.*, 6:595 (2000a).
Duan et al., *Virology*, 261:8 (1999).
Duan et al., *Virus Res.*, 48:41 (1997).
Fisher et al., *Nature Medicine*, 3:306 (1997).
Flotte et al., *Gene Therapy*, 2:357 (1995).
Flotte et al., *Hum. Gene Therapy*, 7: 1145 (1996).
Flotte et al., *J. Biol. Chem.*, 268:3781 (1993).
Flotte et al., *Proc. Natl. Acad. Sci. USA*, 93:10163 (1993).
Grimm et al., *Curr. Gene Ther.*, 3:281 (2003).
Hagstrom et al., *Blood*, 95:2536 (2000).
Hallek et al., *Curr. Res. Molec. Therapeut.*, 1:417 (1998).
Herzog et al., *Proc. Natl. Acad. Sci. USA*, 94:5804 (1997).
Higgins et al., *CABIOS*, 5:151 (1989).
Higgins et al., *Gene* 73:237 (1988).
Kaplitt et al., *Nature Genetics*, 8:148 (1994).
Karlin and Altschul, *Proc. Natl. Acad. Sci. USA* 872264 (1990).
Karlin and Altschul, *Proc. Natl. Acad. Sci. USA* 90:5873 (1993).
Kay et al., *Nat. Genet.*, 24:257 (2000).
Kessler et al., *Proc. Natl. Acad. Sci. USA*, 93:14082 (1996).
King et al., *EMBO J.*, 20:3282 (2001).
Koerberl et al., *Proc. Natl. Acad. Sci. USA*, 94:1426 (1997).
Lewin, *Genes VI*, xviii, 1260 (Oxford University Press, Oxford England; New York, 1997).
McKeon et al., *Human Gene Therapy.* 7:1615 (1996).
Miao et al., *Nature Genetics*, 19:13 (1998).
Musatov et al., *Virology*, 275:411 (2000).
Muzyczka, *Current Topics in Microbiology and Immunology*, 158:97 (1992).
Myers et al., *Virology*, 102:71 (1980).
Myers and Miller, *CABIOS* 4:11 (1988).
Nakai et al., *J. Virol.*, 74:9451 (2000).
Nakai et al., *J. Virol.*, 75:6969 (2001).
Nakai et al., *Mol. Ther.*, 7:101 (2003).
Nakai et al., *Nat. Biotechnol.*, 18:527 (2000).
Needleman and Wunsch, *J. Mol. Biol.* 48:443 (1970).
Pearson et al., *Meth. Mol. Biol.* 24:307 (1994).
Pearson and Lipman, *Proc. Natl. Acad. Sci.* 85:2444 (1988).
Ponnazhagan et al., *Gene*, 190:203 (1997).
Redemann et al., *J. Virol.*, 63:873 (1998).
Reich et al., *Hum. Gene Ther.*, 14:37 (2003).
Rose, *Comprehensive Virology*, 3:1, (1974).
Samulski et al., *J. Virol.*, 61:3096 (1987).
Sanlioglu et al., *Virology*, 268:68 (2000).
Schnepp et al., *J. Virol.*, 77:3495 (2003).
Schnepp et al., *J. Virol.*, 77:3495 (2003).
Smith et al., *Adv. Appl. Math.* 2:482 (1981).
Smuda et al., *Virology*, 84:310 (1991).
Snyder et al., *Human Gene Therapy*, 8:1891 (1997).
Song et al., *Proc. Natl. Acad. Sci. USA*, 98:4084 (2001).
Srivastava et al., *J. Virol.*, 45:555 (1983).
Sun et al., *Nat. Med.*, 6:599 (2000).
Vincent-Lacaze et al., *J. Virol.*, 73:1949 (1999).
Wagner et al., *Hum. Gene Ther.*, 9:889 (1998).
Wagner et al., *Laryngoscope*, 109:266 (1999).
Xiao et al., *J. Virol.*, 70:8098 (1996).
Yan et al., *J. Virol.*, 76:2043 (2002).
Yan et al., *Methods Enzymol.*, 346:334 (2002).
Yan et al., *Proc. Natl. Acad. Sci. USA*, 97:6716 (2000).
Yang et al., *J. Virol.*, 73:9468 (1999).
Zadori et al., *Developmental Cell*, 1:291 (2001).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A vector set comprising at least two recombinant adeno-associated virus (rAAV) vectors, wherein a first rAAV vector has two inverted terminal repeats (ITRs) that are heterologous, and a second rAAV vector has two ITRs, at least one of which is homologous to and is in the same orientation as one of the ITRs in the first rAAV vector, wherein after introduction of the first rAAV vector and the second rAAV vector to a host or a host cell, a chimeric DNA molecule comprising nucleic acid sequences from the first rAAV vector and the second rAAV vector is formed at an increased efficiency relative to a control rAAV vector set comprising two rAAV vectors with four homologous ITRs, the two ITRs of the second rAAV vector may be homologous or heterologous, and wherein the heterologous ITRs are from different AAV serotypes.

2. The set of claim 1 wherein the first rAAV vector or the second rAAV vector has a portion of an open reading frame for a gene product, optionally linked to at least one heterologous transcriptional regulatory element, and a splice donor site 3' to the portion of the open reading frame, wherein the second rAAV vector or the first rAAV vector comprises the remainder of the open reading frame with a splice acceptor site 5' to the remainder of the open reading frame.

3. The set of claim 2 wherein the at least one heterologous transcriptional regulatory element is a promoter.

4. The set of claim 2 wherein the at least one heterologous transcriptional regulatory element comprises a promoter and an enhancer.

5. The set of claim 1 wherein the first rAAV vector or the second rAAV vector comprises an enhancer.

6. The set of claim 5 wherein the second rAAV vector or the first rAAV vector comprises an open reading frame for a gene product.

7. The set of claim 6 wherein the second rAAV vector or the first rAAV vector further comprises a promoter operably linked to the open reading frame for the gene product.

8. The set of claim 2 or 6 wherein the gene product is a therapeutic gene product.

9. The set of claim 2 or 6 wherein the gene product is a catalytic RNA.

10. The set of claim 2 or 6 wherein the gene product is a prophylactic gene product.

11. The set of claim 2 or 6 wherein the gene product is a polypeptide or peptide.

12. The set of claim 1 wherein the first rAAV vector or the second rAAV vector comprises a first promoter.

13. The set of claim 12 wherein the second rAAV vector or the first rAAV vector comprises an open reading frame for a gene product.

14. The set of claim 13 wherein the second rAAV vector or the first rAAV vector further comprises a second promoter operably linked to the open reading frame for the gene product.

15. The set of claim 1, wherein the first rAAV vector comprises an open reading frame for a first gene product and the second rAAV vector comprises an open reading frame for a second gene product, wherein the first and the second gene products are different and the open reading frames are each individually operably linked to an expression control sequence.

16. The set of claim 1 wherein the 3' ITR in the first rAAV vector or the second rAAV vector is an AAV-1, AAV-2, AAV-3, AAV-4, AAV-5, AAV-6, AAV-7 or AAV-8 ITR.

17. The set of claim 1 wherein the 5' ITR in the first rAAV vector is homologous to the 3' ITR in the second rAAV vector.

18. The set of claim 1 wherein the 5' ITR in the first rAAV vector is heterologous to the 3' ITR in the second rAAV vector.

19. The set of claim 1 wherein the 5' ITR in the first rAAV vector or the second rAAV vector is an AAV-1, AAV-2, AAV-3, AAV-4, AAV-5, AAV-6, AAV-7 or AAV-8 ITR.

20. The vector set of claim 1 wherein the ITRs of the second rAAV vector are homologous.

21. The set of claim 1 wherein the ITRs of the second rAAV vector are heterologous.

22. A composition comprising at least two rAAV, the composition comprising:
a first rAAV having two ITRs that are heterologous, and a second rAAV having two ITRs, at least one of which is homologous to and is in the same orientation as one of the ITRs in the first rAAV, wherein after introduction of the first rAAV and the second rAAV to a host or a host cell, a chimeric DNA molecule comprising nucleic acid sequences from the first rAAV and the second rAAV is formed at an increased efficiency relative to two control AAVs comprising four homologous ITRs, wherein the two ITRs of the second rAAV may be homologous or heterologous, and wherein the heterologous ITRs are from different serotypes.

23. The composition of claim 22 further comprising a delivery vehicle.

24. The composition of claim 23 where the vehicle is a pharmaceutically acceptable carrier.

25. An isolated host cell contacted with a composition comprising a first rAAV vector having two ITRs that are heterologous, and a second rAAV vector having two ITRs, at least one of which is homologous to and is in the same orientation as one of the ITRs in the first rAAV vector, wherein after introduction of the composition to the host cell, a chimeric DNA molecule comprising nucleic acid sequences from the first rAAV vector and the second rAAV vector is formed at an increased efficiency relative to a control rAAV vector set having two rAAV vectors with four homologous ITRs, and wherein the two ITRs of the second rAAV vector may be homologous or heterologous, wherein the heterologous ITRs are from different serotypes.

26. The isolated host cell of claim 25 which is a mammalian host cell.

27. An isolated host cell contacted with a first rAAV vector having two ITRs that are heterologous, and a second rAAV vector having two ITRs at least one of is homologous to and is in the same orientation as one of the ITRs in the first rAAV vector, wherein after introduction of the first rAAV vector and the second rAAV vector to a host or a host cell, a chimeric DNA molecule comprising nucleic acid sequences from the first rAAV vector and the second rAAV vector is formed at an increased efficiency relative to a control rAAV vector set having two rAAV vectors with four homologous ITRs, wherein the two ITRs of the second rAAV vector may be homologous or heterologous, and wherein the heterologous ITRs are from different serotypes.

28. The isolated host cell of claim 27 which is a mammalian host cell.

29. A vector set comprising at least two rAAV vectors, wherein a first rAAV vector has two ITRs that are heterologous, and a second rAAV vector has two ITRs one of which is homologous to and is in the same orientation as one of the ITRs in the first rAAV vector, wherein after introduction of the first rAAV vector and the second rAAV vector to a host or a host cell, a chimeric DNA molecule comprising nucleic acid sequences from the first rAAV vector and the rAAV vector is formed at an increased efficiency relative to two control rAAV vectors with four homologous ITRs, wherein one ITR in the first rAAV vector or the second rAAV vector is a pseudo ITR having a palindromic DNA sequence with one of SEQ ID Nos. 3, 7, 8, 9, or 10.

30. A vector set comprising at least two rAAVs, wherein the set comprises:
a) a first rAAV comprising a first recombinant DNA molecule comprising operably linked:
i) a first DNA segment comprising a first 5' ITR;
ii) a second DNA segment comprising a non-AAV DNA sequence; and
iii) a third DNA segment comprising a first 3' ITR, wherein the first 5' ITR is heterologous to the first 3' ITR; and
b) a second rAAV comprising a second recombinant DNA molecule comprising operably linked:
i) a first DNA segment comprising a second 5' ITR;
ii) a second DNA segment comprising a non-AAV DNA sequence which is different than the sequence in the second DNA segment of the first recombinant DNA molecule; and iii) a third DNA segment comprising a second 3' ITR, wherein the second 5' ITR is optionally heterologous to the second 3' ITR, wherein the first 3' ITR is homologous to the second 5' ITR, wherein at least one of the second DNA segments comprises an open reading frame encoding a functional gene product or the two second DNA segments together comprise an open reading frame encoding a functional gene product, which homologous ITRs, after infection of a cell with the vector set, are capable of directional intermolecular recombination yielding a chimeric DNA molecule at an increased efficiency relative to control rAAVs having two rAAVs with four homologous ITRs, wherein the chimeric DNA molecule comprises an expression control sequence so that the open reading frame is capable of being transcribed to yield a RNA molecule that encodes the gene product, wherein one ITR in the first rAAV vector or the second rAAV vector is a pseudo ITR having a palindromic DNA sequence with f one of SEQ ID Nos. 3, 7, 8, 9 or 10.

31. The vector set of claim 29 or 30 wherein the pseudo ITR has an imperfect palindomic DNA sequence.

32. The vector set of claim 29 or 30 wherein the pseudo ITR has SEQ ID NO:3, SEQ ID NO:7 or SEQ ID NO:8.

33. A method to transfer DNAs into a host cell, comprising: contacting the host cell with a first rAAV vector having two ITRs that are heterologous, and a second rAAV vector having two ITRs one of which is homologous to and is in the same orientation as one of the ITRs in the first rAAV vector, wherein after introduction of the first rAAV vector and the second rAAV vector to a host or a host cell, a chimeric DNA molecule comprising nucleic acid sequences from the first rAAV vector and the second rAAV vector is formed at an increased efficiency relative to a control rAAV vector set having two rAAV vectors with four homologous ITRs, wherein the heterologous ITRs are from different AAV serotypes.

34. The method of claim 33 wherein the host cell is a mammalian host cell.

35. The method of claim 33 wherein the first rAAV vector or the second rAAV vector has a portion of an open reading frame for a gene product, optionally linked to at least one heterologous transcriptional regulatory element, and a splice donor site 3' to the portion of the open reading frame, wherein the second rAAV vector or the first rAAV vector comprises the remainder of the open reading frame with a splice acceptor site 5' to the remainder of the open reading frame.

36. The method of claim 35 wherein the at least one heterologous transcriptional regulatory element is a promoter.

37. The method of claim 35 wherein the at least one heterologous transcriptional regulatory element comprises a promoter and an enhancer.

38. The method of claim 33 wherein the first rAAV vector or the second rAAV vector comprises an enhancer.

39. The method of claim 38 wherein the second rAAV vector or the first rAAV vector comprises an open reading frame for a gene product.

40. The method of claim 39 wherein the second rAAV vector or the first rAAV vector further comprises a promoter operably linked to the open reading frame for the gene product.

41. The method of claim 35 or 39 wherein the gene product is a therapeutic gene product.

42. The method of claim 35 or 39 wherein the gene product is a catalytic RNA.

43. The method of claim 35 or 39 wherein the gene product is a prophylactic gene product.

44. The method of claim 35 or 39 wherein the gene product is a polypeptide or a peptide.

45. The method of claim 33 wherein the first rAAV vector or the second rAAV vector comprises a first promoter.

46. The method of claim 30 or 31 wherein the first 5' TPS or second 3' TPS is a native TPS.

47. The method of claim 46 wherein the second rAAV vector or the first rAAV vector further comprises a second promoter operably linked to the open reading frame for the gene product.

48. The method of claim 33 wherein the first rAAV vector comprises an open reading frame for a first gene product and the second rAAV vector comprises an open reading frame for a second gene product, wherein the first and second gene products are different.

49. The method of claim 33 wherein the 3' ITR in the first rAAV vector or the second rAAV vector is an AAV-1, AAV-2, AAV-3, AAV-4, AAV-5, AAV-6, AAV-7 or AAV-8 ITR.

50. The method of claim 33 wherein the 5' ITR in the first rAAV vector is homologous to the 3' ITR in the second rAAV vector.

51. The method of claim 33 wherein the 5' ITR in the first rAAV vector is heterologous to the 3' ITR in the second rAAV vector.

52. The method of claim 33 wherein the 5' ITR in the first rAAV vector or the second rAAV vector is an AAV-1, AAV-2, AAV-3, AAV-4, AAV-5, AAV-6, AAV-7 or AAV-8 ITR.

53. A method to transfer and express a functional gene product in a host cell, the method comprising providing a composition comprising a first rAAV having two ITRs that are heterologous, and a second rAAV having two ITRs, at least one of which is homologous to and is in the same orientation as one of the ITRs in the first rAAV, wherein after introduction of the first rAAV and the second rAAV to a host cell, a chimeric DNA molecule comprising nucleic acid sequences from the first rAAV and the second rAAV is formed at an increased efficiency relative to two control rAAVs with four homologous ITRs, the chimeric DNA molecule comprises an expression control sequence operably linked to an open reading frame encoding a functional gene product, wherein the two ITRs of the second rAAV may be homologous or heterologous, wherein the heterologous ITRs are from different serotypes; and contacting the host cell with the composition so that the host cell expresses the functional gene product.

54. The method of claim 53, wherein the ITRs of the second rAAV vector are homologous.

55. The method of claim 53 wherein the ITRs of the second rAAV vector are heterologous.

56. A method to transfer DNAs into a host cell, comprising: contacting the host cell with a first rAAV vector has two ITRs that are heterologous, and a second rAAV vector has two ITRs one of which is homologous to and is in the same orientation as one of the ITRs in the first rAAV vector, wherein after introduction of the first rAAV vector and the second rAAV vector to a host or a host cell, a chimeric DNA molecule comprising nucleic acid sequences from the first rAAV vector and the second rAAV vector is formed at an increased efficiency relative to control rAAV vectors having two rAAVs with four homologous ITRs, wherein one ITR in the first rAAV vector or the second rAAV vector is a pseudo ITR having a palindromic DNA sequence with one of SEQ ID Nos. 3,7,8,9 or 10.

57. The method of claim 56 wherein the pseudo ITR has an imperfect palindomic DNA sequence.

58. The method of claim 56 wherein the pseudo ITR has SEQ ID NO:3, SEQ ID NO:7 or SEQ ID NO:8.

* * * * *

UNITED STATES PATENT AND TRADEMARK OFFICE
CERTIFICATE OF CORRECTION

PATENT NO. : 8,241,622 B2
APPLICATION NO. : 10/837029
DATED : August 14, 2012
INVENTOR(S) : Engelhardt et al.

It is certified that error appears in the above-identified patent and that said Letters Patent is hereby corrected as shown below:

On the Title page, in column 1, (12) Kind of the patent, line 2, and in column 1, (75) Inventors, line 1, delete "Englehardt" and insert --Engelhardt--, therefor In the Specifications In column 1, line 17, delete "This invention was made, at least in part, with a grant from the Government of the United States of America (grants HL58340 and DK54759 from the National Institutes of Health). The Government may have certain rights in the invention." and insert --This invention was made with government support under grant number HL58340 and DK54759 awarded by National Institutes of Health. The Government has certain rights in the invention.--, therefor In column 2, line 20, delete "68" and insert --Rep68--, therefor In column 2, line 21, delete "Muzyczka;" and insert --Muzyczka,--, therefor In column 2, line 23, delete "p5" and insert --$p_5$--, therefor In column 2, line 24, delete "p40" and insert --$p_{40}$--, therefor In column 2, line 28, delete "p5" and insert --$p_5$--, therefor In column 2, line 43, delete "concatemers" and insert --concatamers--, therefor In column 9, line 9, delete "AAV" and insert --rAAV--, therefor In column 12, line 54, delete "5 '" and insert --5'--, therefor In column 17, line 62, delete "NO: 1" and insert --NO:1--, therefor Signed and Sealed this
Twenty-eighth Day of May, 2013

Teresa Stanek Rea
*Acting Director of the United States Patent and Trademark Office*

CERTIFICATE OF CORRECTION (continued)  Page 2 of 4
U.S. Pat. No. 8,241,622 B2

In column 18, line 1, delete "(SEQ ID NO:8)(C), AAV-2 TPS (SEQ ID NO:1)(D)" and insert --(SEQ ID NO:8) (C), AAV-2 TPS (SEQ ID NO:1) (D)--, therefor In column 18, line 2, delete "(SEQ ID NO:7)(E)" and insert --(SEQ ID NO:7) (E)--, therefor In column 18, line 31, delete "encapsidatiuon" and insert --encapsidation--, therefor In column 18, line 32, delete "1,2,3," and insert --1, 2, 3,--, therefor In column 19, line 3, delete "AAV." and insert --AAV--, therefor In column 23, line 2, delete "maker.A" and insert --maker. A--, therefor In column 26, line 8, delete "(1993)" and insert --(1993))--, therefor In column 29, line 30, delete "p5" and insert --$p_5$--, therefor In column 29, line 34, delete "p5" and insert --$p_5$--, therefor In column 29, line 48, delete "p5" and insert --$p_5$--, therefor In column 37, line 61, delete "AAV" and insert --rAAV--, therefor In column 40, line 60, delete "pAV2:2 LacZdonor" and insert --pAV2:2LacZdonor--, therefor In column 40, line 60-61, delete "pAV2:2 LacZacceptor" and insert --pAV2:2LacZacceptor--, therefor In column 40, line 64, delete "AV2:2 LacZdonor" and insert --AV2:2LacZdonor--, therefor In column 40, line 64, delete "AV2:2 LacZacceptor" and insert --AV2:2LacZacceptor--, therefor In column 41, line 2, delete "pAV2:2 LacZdonor" and insert --pAV2:2LacZdonor--, therefor In column 41, line 8, delete "pAV2:2 LacZdonor" and insert --pAV2:2LacZdonor--, therefor In column 41, line 8-9, delete "pAV2:2 LacZacceptor" and insert --pAV2:2LacZacceptor--, therefor In column 41, line 11, delete "pAV5:5 LacZdonor" and insert --pAV5:5LacZdonor--, therefor In column 41, line 11, delete "pAV5:5 LacZacceptor" and insert --pAV5:5LacZacceptor--, therefor In column 41, line 13, delete "AV5:5 LacZdonor" and insert --AV5:5LacZdonor--, therefor In column 41, line 13, delete "AV5:5 LacZacceptor" and insert --AV5:5LacZacceptor--, therefor CERTIFICATE OF CORRECTION (continued)
U.S. Pat. No. 8,241,622 B2

In column 41, line 15, delete "pAV5:2 LacZdonor" and insert --pAV5:2LacZdonor--, therefor In column 41, line 16, delete "pAV2:5 LacZacceptor" and insert --pAV2:5LacZacceptor--, therefor In column 41, line 17, delete "pAV5:2 LacZdonor" and insert --pAV5:2LacZdonor--, therefor In column 41, line 17, delete "pAV2:2 LacZdonor" and insert --pAV2:2LacZdonor--, therefor In column 41, line 18, delete "pAV5:5 LacZdonor" and insert --pAV5:5LacZdonor--, therefor In column 41, line 19, delete "pAV5:5 LacZdonor" and insert --pAV5:5LacZdonor--, therefor In column 41, line 21-22, delete "pAV2:2 LacZdonor" and insert --pAV2:2LacZdonor--, therefor In column 41, line 22, delete "pAV5:2 LacZdonor" and insert --pAV5:2LacZdonor--, therefor In column 41, line 26, delete "pAV2:5 LacZacceptor" and insert --pAV2:5LacZacceptor--, therefor In column 41, line 28, delete "pAV5:5 LacZacceptor" and insert --pAV5:5LacZacceptor--, therefor In column 41, line 29, delete "pAV5:5 LacZacceptor" and insert --pAV5:5LacZacceptor--, therefor In column 41, line 32, delete "pAV2:2 LacZacceptor" and insert --pAV2:2LacZacceptor--, therefor In column 41, line 48-49, delete "theintravector" and insert --the intravector--, therefor In column 42, line 2, delete "Inc" and insert --Inc.--, therefor In column 42, line 9, delete "(Tet$^r$)])}" and insert --(Tet$^r$))])}--, therefor In column 45, line 19, delete "AV2/5:2" and insert --AV2:5/2--, therefor In column 45, line 54, delete "AV2: 5/2eGFP" and insert --AV2:5/2eGFP--, therefor In column 46, line 21, delete "intramolecular" and insert --intermolecular--, therefor In column 46, line 59, delete "StuI" and insert --StuI--, therefor In column 47, line 36, delete "DNase" and insert --DNAse--, therefor In column 47, line 66, delete "AV2:5 LacZdonor" and insert --AV2:5LacZdonor--, therefor In column 47, line 66-67, delete "AV2:5 LacZacceptor" and insert --AV2:5LacZacceptor--, therefor In column 48, line 2-3, delete "AV2:2 LacZdonor" and insert --AV2:2LacZdonor--, therefor In column 48, line 3, delete "AV2:2 LacZacceptor" and insert --AV2:2LacZdonor--, therefor In column 48, line 12-13, delete "AV2:2 LacZdonor" and insert --AV2:2LacZdonor--, therefor In column 48, line 13, delete "AV2:2 LacZacceptor" and insert --AV2:2LacZdonor--, therefor In column 48, line 13, delete "AV5:2 LacZdonor" and insert --AV5:2LacZdonor--, therefor In column 50, line 4, delete "NO: 10" and insert --NO:10--, therefor In column 53, line 5, delete "Vol" and insert --Vol.--, therefor In column 53, line 6, delete "pp" and insert --pp.--, therefor In column 53, line 8, delete "Vol" and insert --Vol.--, therefor In column 53, line 9, delete "Vol" and insert --Vol.--, therefor In column 53, line 9, delete "pp" and insert --pp.--, therefor In column 53, line 13, after "Res.", insert --,--, therefor In column 53, line 34, after "Gene", insert --,--, therefor In column 53, line 36, after "USA", insert --,--, therefor In column 53, line 38, after "USA", insert --,--, therefor In column 54, line 1, delete "Therapy." and insert --Therapy,--, therefor In column 54, line 7, after "CABIOS", insert --,--, therefor In column 54, line 12, after "Biol.", insert --,--, therefor In column 54, line 13, after "Biol.", insert --,--, therefor In column 54, line 23, after "Math.", insert --,--, therefor In the Claims In column 61, line 19, in Claim 30, after "with", delete "f", therefor In column 62, line 59, in Claim 56, delete "7,8,9" and insert --7, 8, 9--, therefor

SEQUENCE LISTING

<160> NUMBER OF SEQ ID NOS: 11

<210> SEQ ID NO 1
<211> LENGTH: 145
<212> TYPE: DNA
<213> ORGANISM: Adeno-associated virus

<400> SEQUENCE: 1
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145

<210> SEQ ID NO 2
<211> LENGTH: 169
<212> TYPE: DNA

<213> ORGANISM: Adeno-associated virus

<400> SEQUENCE: 2

```
ctctcccccc tgtcgcgttc gctcgctcgc tggctcgttt ggggggggtgg cagctcaaag    60
agctgccaga cgacggcccct ctggccgtcg ccccccaaa cgagccagcg agcgagcgaa   120
cgcgacaggg gggagagtgc cacactctca agcaaggggg ttttgtaag               169
```

<210> SEQ ID NO 3
<211> LENGTH: 139
<212> TYPE: DNA
<213> ORGANISM: Artificial Sequence
<220> FEATURE:
<223> OTHER INFORMATION: A synthetic construct.

<400> SEQUENCE: 3

```
tctagaaagg cctaggcagg tgtggtaagc ggaccaggca ggcagacccc ggcgcgctat    60
gcgcgccgga tctccccaca aagtggggag aggtctgcct gcctggtccg cttaccacac   120
ctgcctaggc cttctcgag                                                139
```

<210> SEQ ID NO 4
<211> LENGTH: 145
<212> TYPE: DNA
<213> ORGANISM: Adeno-associated virus

<400> SEQUENCE: 4

```
ttgcccactc cctctctgcg cgctcgctcg ctcggtgggg cctgcggacc aaaggtccgc    60
agacggcaga gctctgctct gccggcccca ccgagcgagc gagcgcgcag agagggagtg   120
ggcaactcca tcactagggg taatc                                         145
```

<210> SEQ ID NO 5
<211> LENGTH: 145
<212> TYPE: DNA
<213> ORGANISM: Adeno-associated virus

<400> SEQUENCE: 5

```
ttggccactc cctctatgcg cactcgctcg ctcggtgggg cctggcgacc aaaggtcgcc    60
agacggacgt gctttgcacg tccggcccca ccgagcgagc gagtgcgcat agagggagtg   120
gccaactcca tcactagagg tatgg                                         145
```

<210> SEQ ID NO 6
<211> LENGTH: 145
<212> TYPE: DNA
<213> ORGANISM: Adeno-associated virus

<400> SEQUENCE: 6

```
ttggccactc cctctatgcg cgctcgctca ctcactcggc cctggagacc aaaggtctcc    60
agactgccgg cctctggccg gcagggccga gtgagtgagc gagcgcgcat agagggagtg   120
gccaactcca tcatctaggt ttgcc                                         145
```

<210> SEQ ID NO 7
<211> LENGTH: 125
<212> TYPE: DNA
<213> ORGANISM: Artificial Sequence
<220> FEATURE:
<223> OTHER INFORMATION: A synthetic construct.

<400> SEQUENCE: 7

```
ccggatccgt ccgagccatt ccgctcggtc cgtccgtccg gtgcagagag gggctctctg    60
```

```
catagaggtg tggggcacac ctctccggac ggacggaccg agcggaatgg ctcggacgga    120
tccgg                                                                125

<210> SEQ ID NO 8
<211> LENGTH: 127
<212> TYPE: DNA
<213> ORGANISM: Artificial Sequence
<220> FEATURE:
<223> OTHER INFORMATION: A synthetic construct.

<400> SEQUENCE: 8
aaggcctagg caggtgtggt aagcggacca ggcaggcaga cctctcccca ctttgtgggg    60
agatccggcg cgcatagcgc gccggggtct gcctgcctgg tccgcttacc acacctgcct   120
aggcctt                                                             127

<210> SEQ ID NO 9
<211> LENGTH: 125
<212> TYPE: DNA
<213> ORGANISM: Artificial Sequence
<220> FEATURE:
<223> OTHER INFORMATION: A synthetic construct.

<400> SEQUENCE: 9
tactatcagc gcataaaatc actgactagt atcttgccta ccgggcgacc aaaggtcgcc    60
cgacgcccgg gctttgcccg ggcggtaggc aagatactag tcagtgattt tatccctga   120 tagta                                                              125

<210> SEQ ID NO 10
<211> LENGTH: 125
<212> TYPE: DNA
<213> ORGANISM: Artificial Sequence
<220> FEATURE:
<223> OTHER INFORMATION: A synthetic construct.

<400> SEQUENCE: 10
tactatcagc gcataaaatc actgactagt atcttgccta cggctagtgc atagcactag    60
ccaggatgga gctatgctcc atccgtaggc aagatactag tcagtgattt tatgcgctga   120
tagta                                                              125

<210> SEQ ID NO 11
<211> LENGTH: 145
<212> TYPE: DNA
<213> ORGANISM: Adeno-associated virus

<400> SEQUENCE: 11
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145
```